US011034775B2

(12) United States Patent
Olsen et al.

(10) Patent No.: US 11,034,775 B2
(45) Date of Patent: Jun. 15, 2021

(54) CYSTEINE-OPTIMIZED STRADOMERS

(71) Applicant: Gliknik Inc., Baltimore, MD (US)

(72) Inventors: Henrik Olsen, Baltimore, MD (US); David S. Block, Baltimore, MD (US)

(73) Assignee: GLIKNIK INC., Baltimore, MD (US)

(*) Notice: Subject to any disclaimer, the term of this patent is extended or adjusted under 35 U.S.C. 154(b) by 0 days.

(21) Appl. No.: 16/302,841

(22) PCT Filed: Jun. 7, 2017

(86) PCT No.: PCT/US2017/036425
§ 371 (c)(1),
(2) Date: Nov. 19, 2018

(87) PCT Pub. No.: WO2017/214321
PCT Pub. Date: Dec. 14, 2017

(65) Prior Publication Data
US 2019/0194357 A1 Jun. 27, 2019

Related U.S. Application Data

(60) Provisional application No. 62/346,994, filed on Jun. 7, 2016, provisional application No. 62/350,534, filed on Jun. 15, 2016.

(51) Int. Cl.
| A61K 9/19 | (2006.01) |
| A61K 38/00 | (2006.01) |
| C07K 16/46 | (2006.01) |
| C07K 16/00 | (2006.01) |
| A61K 9/00 | (2006.01) |

(52) U.S. Cl.
CPC ............ *C07K 16/46* (2013.01); *A61K 9/0019* (2013.01); *C07K 16/00* (2013.01); *A61K 38/00* (2013.01); *C07K 2317/522* (2013.01); *C07K 2317/524* (2013.01); *C07K 2317/526* (2013.01); *C07K 2317/53* (2013.01); *C07K 2317/71* (2013.01); *C07K 2317/92* (2013.01); *C07K 2318/00* (2013.01)

(58) Field of Classification Search
CPC .. A61K 9/0019; A61K 38/00; C07K 2317/53; C07K 2317/52; C07K 2317/526; C07K 2317/524; C07K 2317/71; C07K 2317/92; C07K 2318/00
See application file for complete search history.

(56) References Cited

U.S. PATENT DOCUMENTS

| 5,681,566 | A | 10/1997 | Stevenson |
| 5,877,396 | A | 3/1999 | Ravetch et al. |
| 6,004,781 | A | 12/1999 | Seed |
| 6,660,266 | B1 | 12/2003 | Mosser et al. |
| 7,148,321 | B2 | 12/2006 | Gillies et al. |
| 7,511,121 | B2 | 3/2009 | Arnason et al. |
| 7,524,487 | B2 | 4/2009 | Mosser et al. |
| 7,666,622 | B2 | 2/2010 | Sharma et al. |
| 8,147,835 | B2 | 4/2012 | Ledbetter et al. |
| 8,258,263 | B2 | 9/2012 | Morrison et al. |
| 8,680,237 | B2 | 3/2014 | Strome et al. |
| 9,512,208 | B2 | 12/2016 | Strome et al. |
| 9,512,210 | B2 | 12/2016 | Strome et al. |
| 9,683,044 | B2 | 6/2017 | Block et al. |
| 9,926,362 | B2 | 3/2018 | Strome et al. |
| 10,208,105 | B2 | 2/2019 | Strome et al. |
| 2002/0115157 | A1 | 8/2002 | Davis et al. |
| 2002/0142374 | A1 | 10/2002 | Gallo et al. |
| 2002/0147326 | A1 | 10/2002 | Chaikin et al. |
| 2003/0044423 | A1 | 3/2003 | Gillies et al. |
| 2003/0118592 | A1 | 6/2003 | Ledbetter et al. |
| 2003/0216546 | A1 | 11/2003 | Tykocinski et al. |
| 2003/0235578 | A1 | 12/2003 | Stinson et al. |
| 2004/0062763 | A1 | 4/2004 | Mosser et al. |
| 2004/0110226 | A1 | 6/2004 | Lazar et al. |
| 2004/0147731 | A1 | 7/2004 | Parkos |
| 2004/0151725 | A1 | 8/2004 | Gray et al. |
| 2004/0265321 | A1 | 12/2004 | Johnson et al. |
| 2005/0033029 | A1 | 2/2005 | Lu |
| 2005/0249723 | A1 | 11/2005 | Lazar |
| 2006/0074225 | A1 | 4/2006 | Chamberlain et al. |
| 2006/0263856 | A1 | 11/2006 | Gillies et al. |
| 2006/0275254 | A1 | 12/2006 | Kim et al. |
| 2007/0128111 | A1* | 6/2007 | Reilly ............... C07K 16/2896 424/1.49 |
| 2007/0269369 | A1 | 11/2007 | Gegg et al. |

(Continued)

FOREIGN PATENT DOCUMENTS

| EP | 0553667 A1 | 8/1993 |
| EP | 0439540 B1 | 6/1995 |

(Continued)

OTHER PUBLICATIONS

Lund et al., The Journal of Immunology 157:4963-4969 (Year: 1996).*
Allen et al., Biochemistry 48: 3755-3766 (Year: 2009).*
"Synthetic peptides with high biochemical activity," downloaded on Sep. 7, 2012 from http://www.genosphere-biotech.com/Long-Active-Peptides.html, 1 page.
Abaza, et al., "Effect of amino acid substitutions outside an antigenic site on protein binding to monoclonal antibodies of predetermined specificity obtained by peptide immunization: demonstration with region 94-100 (antigenic site 3) of myoglobin." Journal of Protein Chemistry (1992); 11 (5): 433-444.

(Continued)

*Primary Examiner* — Phuong Huynh
(74) *Attorney, Agent, or Firm* — Cooley LLP

(57) ABSTRACT

The present disclosure involves biologically active proteins termed cysteine-optimized multimerizing stradomers. Thus, the present disclosure provides compositions and methods providing anti-autoimmune and anti-inflammatory activities, useful in the treatment of diseases and conditions including autoimmune diseases, inflammatory diseases, or infectious diseases.

14 Claims, 22 Drawing Sheets
Specification includes a Sequence Listing.

(56) References Cited

U.S. PATENT DOCUMENTS

| | | |
|---|---|---|
| 2008/0242845 A1 | 10/2008 | Lazar et al. |
| 2008/0260738 A1 | 10/2008 | Moore et al. |
| 2008/0267980 A1 | 10/2008 | Tomlinson et al. |
| 2009/0104210 A1 | 4/2009 | Tota et al. |
| 2009/0117133 A1 | 5/2009 | Arnason et al. |
| 2009/0136485 A1 | 5/2009 | Chu et al. |
| 2009/0175867 A1 | 7/2009 | Thompson et al. |
| 2009/0217401 A1 | 8/2009 | Korman et al. |
| 2009/0252729 A1 | 10/2009 | Farrington et al. |
| 2009/0258031 A1 | 10/2009 | Karrer et al. |
| 2009/0304696 A1 | 12/2009 | Lawson et al. |
| 2009/0304715 A1 | 12/2009 | Masuho et al. |
| 2010/0048877 A1 | 2/2010 | Ruker et al. |
| 2010/0093979 A1 | 4/2010 | Lazar |
| 2010/0143353 A1 | 6/2010 | Mosser et al. |
| 2010/0158909 A1 | 6/2010 | Mcdonagh et al. |
| 2010/0227805 A1 | 9/2010 | Karin et al. |
| 2010/0239633 A1 | 9/2010 | Strome et al. |
| 2011/0243966 A1 | 10/2011 | Farrington et al. |
| 2011/0305697 A1 | 12/2011 | Walczak |
| 2012/0100099 A1 | 4/2012 | Wang et al. |
| 2012/0149876 A1 | 6/2012 | Von Kreudenstein et al. |
| 2012/0283417 A1 | 11/2012 | Mosser et al. |
| 2012/0309941 A1 | 12/2012 | Strome et al. |
| 2013/0156765 A1* | 6/2013 | Block ............... A61K 31/573 424/134.1 |
| 2013/0266579 A1 | 10/2013 | Wei et al. |
| 2014/0072582 A1 | 3/2014 | Block et al. |
| 2014/0105913 A1 | 4/2014 | Strome et al. |
| 2014/0120581 A1 | 5/2014 | Niwa et al. |
| 2014/0335075 A1 | 11/2014 | Strome et al. |
| 2014/0370012 A1 | 12/2014 | Block et al. |
| 2015/0056185 A1 | 2/2015 | Strome et al. |
| 2015/0071948 A1 | 3/2015 | Lazar et al. |
| 2015/0166636 A1 | 6/2015 | Igawa et al. |
| 2015/0218236 A1 | 8/2015 | Pleass |
| 2016/0229913 A1 | 8/2016 | Bosques et al. |
| 2016/0280768 A1 | 9/2016 | Strome et al. |
| 2016/0355570 A1 | 12/2016 | Strome et al. |
| 2017/0008951 A1 | 1/2017 | Block et al. |
| 2017/0029505 A1 | 2/2017 | Griffin et al. |
| 2017/0081406 A1 | 3/2017 | Fallah-arani et al. |
| 2017/0088603 A1 | 3/2017 | Fallah-arani et al. |
| 2018/0002388 A1 | 1/2018 | Block et al. |
| 2018/0094061 A1 | 4/2018 | Block et al. |
| 2018/0186862 A1 | 7/2018 | Strome et al. |
| 2018/0244772 A1 | 8/2018 | Block et al. |
| 2019/0218275 A1 | 7/2019 | Strome et al. |
| 2019/0389941 A1 | 12/2019 | Block et al. |

FOREIGN PATENT DOCUMENTS

| | | | |
|---|---|---|---|
| EP | 2006305 A9 | 7/2009 | |
| JP | 2013-543483 A | 12/2013 | |
| WO | WO 1990/004413 A1 | 5/1990 | |
| WO | WO 1994/003191 A1 | 2/1994 | |
| WO | WO 1994/015640 A1 | 7/1994 | |
| WO | WO 2000/009560 A2 | 2/2000 | |
| WO | WO 2002/056910 A1 | 7/2002 | |
| WO | WO 2002/072605 A2 | 9/2002 | |
| WO | WO 2002/072608 A2 | 9/2002 | |
| WO | WO-02072605 A2 * | 9/2002 | ............. C07K 16/30 |
| WO | WO 2003/010202 A1 | 2/2003 | |
| WO | WO 2003/051933 A1 | 6/2003 | |
| WO | WO 2003/074679 A2 | 9/2003 | |
| WO | WO 2003/105898 A1 | 12/2003 | |
| WO | WO 2004/062619 A2 | 7/2004 | |
| WO | WO 2005/000895 A2 | 1/2005 | |
| WO | WO 2005/007809 A2 | 1/2005 | |
| WO | WO 2005/077981 A2 | 8/2005 | |
| WO | WO 2005/089503 A2 | 9/2005 | |
| WO | WO 2006/008739 A2 | 1/2006 | |
| WO | WO 2006/061650 A2 | 6/2006 | |
| WO | WO 2006/071206 A2 | 7/2006 | |
| WO | WO 2006/074199 A1 | 7/2006 | |
| WO | WO 2007/021129 A1 | 2/2007 | |
| WO | WO 2007/100083 A1 | 9/2007 | |
| WO | WO 2008/138131 A1 | 11/2008 | |
| WO | WO 2008/151088 A2 | 12/2008 | |
| WO | WO 2008/157378 A2 | 12/2008 | |
| WO | WO 2009/079242 A2 | 6/2009 | |
| WO | WO 2010/065578 A2 | 6/2010 | |
| WO | WO 2011/060242 A2 | 5/2011 | |
| WO | WO 2011/073692 A1 | 6/2011 | |
| WO | WO 2011/091078 A2 | 7/2011 | |
| WO | WO 2012/001647 A2 | 1/2012 | |
| WO | WO 2012/016073 A2 | 2/2012 | |
| WO | WO 2013/112986 A1 | 8/2013 | |
| WO | WO 2014/006217 A1 | 1/2014 | |
| WO | WO 2014/031646 A2 | 2/2014 | |
| WO | WO 2015/132364 A1 | 9/2015 | |
| WO | WO 2015/158867 A1 | 10/2015 | |
| WO | WO 2016/009232 A1 | 1/2016 | |
| WO | WO 2016/073917 A1 | 5/2016 | |
| WO | WO 2016/139365 A1 | 9/2016 | |
| WO | WO 2017/005767 A1 | 1/2017 | |
| WO | WO 2017/013203 A1 | 1/2017 | |
| WO | WO 2017/019565 A1 | 2/2017 | |
| WO | WO 2017/036905 A1 | 3/2017 | |
| WO | WO 2017/214321 A1 | 12/2017 | |
| WO | WO 2018/018047 A2 | 1/2018 | |

OTHER PUBLICATIONS

Alegre and Fallarino, "Mechanisms of CTLA-4-Ig in tolerane induction." Curr. Pharmaceutical Design (2006); 12 (2): 149-160.

Anderson, C. A. et al., "Cutting Edge: Biasing immune responses by directing antigen to macrophage Fcγ receptors." J. Immunology (2002); 168: 3697-3701.

Andreson, et al., "Product Equivalence Study Comparing the Tolerability, Pharmacokinetics, and Pharmacodynamics of Various Human Immunoglobulin-G Formulations." The Journal of Clinical Pharmacology (2000); 40 (7): 722-730.

Arase, et al., "Association with FcRγ is Essential for Activation Signal through NKR-P1 (CD161) in Natural Killer (NK) Cells and NK1.1+ T Cells." Journal of Experimental Medicine (1997); 186 (12): 1957-1963.

Arduin, et al., "Highly reduced binding to high and low affinity mouse Fc gamma receptors by L234A/L235A and N297A Fc mutations engineered into mouse IgG2a." Molecular Immunology (2015); 63 (2): 456-463.

Asanuma, et al., "Multimerization and collagen binding of vitronectin is modulated by its glycosylation." International Congress Series (2001); vol. 1223, pp. 97-101.

Aslan, et al., "Plasmon light scattering in biology and medicine: new sensing approaches, visions and perspectives." Current Opinion in Chemical Biology (2005); 9 (5): 538-544.

Aubin, et al., "Indirect inhibition of in vivo and in vitro T-cell responses by intravenous immunoglobulins due to impaired antigen presentation." Blood (2010); 115 (9): 1727-1734.

Augeber, et al., "Are aggregates of IgG the effective part of high-dose immunoglobulin therapy in adult idiopathic thrombocytopenic purpura (ITP)?" Blut (1985); 50: 249-252.

Bánki, et al., "Cross-Linking of CD32 Induces Maturation of Human Monocyte-Derived Dendritic Cells Via NF-κB Signaling Pathway." The Journal of Immunology (2003); 170 (8): 3963-3970.

Barrionuevo, et al.,"Immune complex-FcγR interaction modulates monocyte/macrophage molecules involved in inflammation and immune response." Clin. Exp. Immunol. (2013); 133 (2): 200-207.

Bazin, et al., "Tetramolecular immune complexes are more efficient than IVIg to prevent antibody-dependent in vitro and in vivo and in in vivo phagocytosis of blood cells." British J. Haematol. (2004); 127 (1): 90-96.

Blundell, et al., "Engineering the fragment crystallizable (Fc) region of human IgG1 multimers and monomers to fine-tune interactions with sialic acid-dependent receptors." Journal of Biological Chemistry (2017); 292: 12994-113007.

(56) References Cited

OTHER PUBLICATIONS

Boyle, et al., "Human Antibodies Fix Complement to Inhibit Plasmodium falciparum Invasion of Erythrocytes and Are Associated with Protection against Malaria." Immunity (2015); 42 (3): 580-590.
Boyle, J.J., et al., "Solid-Phase Immunoglobulins IgG and IgM Activate Macrophages with Solid-Phase IgM Acting via a Novel Scavenger Receptor A Pathway." The American Journal of Pathology (2012); 181 (1): 347-361.
Braathen, R., et al., "The Carboxyl-terminal Domains of IgA and IgM Direct Isotype-specific Polymerization and Interaction with the Polymeric Immunoglobulin Receptor." The Journal of Biological Chemistry (2002); 277 (45): 42755-42762.
Bruhns, et al., "Specificity and affinity of human Fc receptors and their polymorphic variants for human IgG subclasses." Blood (2009); 113 (16): 3716-3725.
Burton, "Immunoglobulin G: Functional sites." Molecular Immunology (1985); 22 (3): 161-206.
Campbell, A. M., "Monoclonal Antibody Technology," In Laboratory Techniques in Biochemistry and Molecular Biology (1984); vol. 13, Elsevier Science Publishers, pp. 1-32.
Caron, et al., "Engineered Humanized Dimeric Forms of IgG are More Effective Antibodies." J. Exp. Med. (1992); 176: 1191-1195.
Chang, et al., "Intravenous immunoglobulins reverse acute vaso-occlusive crises in sickle cell mice through rapid inhibition of neutrophil adhesion." Blood (2008); 111: 915-923.
Chappel, et al., "Identification of the Fcγ receptor class I binding site in human IgG through the use of recombinant IgG1/IgG2 hybrid and point-mutated antibodies." Proc. Natl. Acad. Sci. USA (1991); 88: 9036-9040.
Chougnet, et al., "Molecular analysis of decreased interleukin-12 production in person infected with human immunodeficiency virus." J. Infectious Diseases (1996); 174: 46-53.
Chu, et al., "Inhibition of B cell receptor-mediated activation of primary human B cells by coengagement of CD19 and FcγRIIb with Fc-engineered antibodies." Molecular Immunology (2008); 45 (15): 3926-3933.
Cohen, P., "Systemic Autoimmunity," in Fundamental Immunology, 4th edition, Philadelphia, Lippencot-Raven Publishers, pp. 1067-1088 (1999).
Colman, et al., "Effects of amino acid sequence changes on antibody-antigen interactions," Research in Immunology (1994); 145 (1): 33-36.
Constantine, M. M., et al., "Intravenous immunoglobulin utilization in the Canadian Atlantic provinces: a report of the Atlantic Collaborative Intravenous Immune Globulin utilization working group." Transfusion (2007); 47: 2072-2080.
Czajkowsky, D.M., et al., Fc-fusion proteins: new developments and future perspectives. EMBO Molecular Medicine (Oct. 2012); 4(10): 1015-1028. Epub Jul. 26, 2012.
Davidson, et al, "T helper cell1-type CD4+ T cells, but not B cells, mediate colitis in interleukin 10-deficient mice." J. Exp. Med. (1996); 184: 241-251.
Davis, et al., "Differential B cell expression of mouse Fc receptor homologs." International Immunology (2004); 16 (9): 1343-1353.
Davis, et al., "Intermolecular disulfide bonding in IgM: effects of replacing cysteine residues in the μ heavy chain." EMBO J. (1989); 8 (9): 2519-2526.
Debre, et al., "Infusion of Fcγ fragments for treatment of children with acute immune thrombocytopenic purpura." Lancet (1993); 342: 945-949.
Deo, Y. M. et al., "Clinical significance of IgG Fc receptors and FcγR-directed immunotherapies." Immunology Today (1997); 18 (3) :127-135.
Diebolder, et al., "Complement is activated by IgG hexamers assembled at the cell surface." Science (Mar. 2014); 343(6176): 1260-1263.
Dinarello, C. A., "Proinflammatory and anti-inflammatory cytokines as mediators in the pathogenesis of septic shock." Chest (1997); 112: 321S-329S.

European examination report dated May 18, 2011 in co-pending European application No. 08769936.9, 7 pages.
European Search Report for EP Application No. 13169230.3, dated Oct. 25, 2013, 15 pages.
Extended European Search Report for EP Application No. 13830394.6, dated Mar. 4, 2016, 9 pages.
Extended European Search Report for EP Application No. 16831166.0, dated Feb. 11, 2019, 8 pages.
Extended European Search Report for EP Application No. 18166541.5, dated Oct. 18, 2018, 9 pages.
Fan, et al., "Production of multivalent protein binders using a self-trimerizing collagen-like peptide scaffold." The FASEB Journal (2008); 22 (11): 3795-2804.
Flanagan, et al., "Soluble Fc Fusion Proteins for Biomedical Research." Meth. Mol. Biol. (2007); 378: 33-52.
Garratty, "Severe reactions associated with transfusion of patients with sickle cell disease." Transfusion (1997); 37 (4): 357-361.
Gavin, et al., "Cutting Edge: Identification of the Mouse IgG3 Receptor: Implications for Antibody Effector Function at the Interface Between Innate and Adaptive Immunity." J. Immunol. (1998); 160 (1): 20-23.
Gerber, et al., "Reversing Lipopolysaccharide Toxicity by Ligating the Macrophage Fcγ Receptors." J. Immunology (2001); 166: 6861-6868.
Ghielmetti, et al., "Gene expression profiling of the effects of intravenous immunoglobulin in human whole blood." Molecular Immunology (2006); 43 (7): 939-949.
Ghumra, et al., "Structural requirements for the interaction of human IgM and IgA with the human Fcα/μ receptor." Eur. J. Immunol. (2009); 39 (4): 1147-1156.
Gliknik website. www.gliknik.com/research/stradomer.php, 2012.
Goldenberg, "Multiple Sclerosis Review." P&T (2012); 37(3): 175-184.
Gralnick, et al., "Role of carbohydrate in multimeric structure of factor VIII/von Willebrand factor protein." PNAS (1983); 80 (9): 2771-2774.
Greenwood, et al., "Engineering multiple domains forms of the therapeutic antibody CAMPATH-1H: Effect on complement Lysis," Ther. Immunol. (1994); 1(5):247-255.
Ha, et al., "Isolation and characterization of IgG1 with asymmetrical Fc glycosylation." Glycobiology (2011); 21 (8): 1087-1096.
Harbury, et al. "A switch between two-, three-, and four-stranded coiled coils in GCN4 leucine zipper mutants." Science (1993); 262: 1401-1407.
Hart, et al., "Comparison of the suppressive effects of interleukin-10 and interleukin-4 on synovial fluid macrophages and blood monocytes from patients with inflammatory arthritis." Immunology (1995); 84: 536-542.
Hu, et al., "Targeting tumor vasculature endothelial cells and tumor cells for immunotherapy of human melanoma in a mouse xenograft model." PNAS (1999); 96 (14): 8161-8166.
Huang, et al., "In vitro study of combination of rhOPG-Fc and alendronate on inhibition osteoclast." Zhonghua Wai Ke Za Zhi (2005); 43(12):812-816. (Abstract Only, Article in Chinese).
Hughes-Jones and Gardner, "Reaction between the isolated globular sub-units of the complement component C1q and IgG-complexes." Mol Immunol. (1979); 16 (9): 697-701.
International Preliminary Report on Patentability for International Application No. PCT/US2015/059574, dated May 9, 2017, 12 pages.
International Preliminary Report on Patentability for International Application No. PCT/US2016/043746, dated Jan. 30, 2018, 9 pages.
International Preliminary Report on Patentability for International Application No. PCT/US2017/036425, dated Dec. 11, 2018, 8 pages.
International Preliminary Report on Patentability for International Application No. PCT/US2017/043538, dated Jan. 22, 2019, 9 pages.
International Preliminary Report on Patentability for PCT/US2013/023404, 17 pages, dated Jul. 29, 2014.
International Preliminary Report on Patentability for PCT/US2013/055800, 23 pages, dated Feb. 24, 2015.

(56) References Cited

OTHER PUBLICATIONS

International Preliminary Report on Patentability, dated Jan. 29, 2013 in International application No. PCT/US2011/045768, 10 pages.
International Preliminary Report on Patentability, PCT appln. No. PCT/US2008/065428, 8 pages, dated Dec. 1, 2009.
International Search Report and Written Opinion for International Application No. PCT/US2011/045768, 15 pages, dated Mar. 8, 2012.
International Search Report and Written Opinion for International Application No. PCT/US2015/059574, dated Feb. 3, 2016, 14 pages.
International Search Report and Written Opinion for International Application No. PCT/US2016/043746, dated Jan. 17, 2017, 13 pages.
International Search Report and Written Opinion for International Application No. PCT/US2017/036425, dated Oct. 31, 2017, 13 pages.
International Search Report and Written Opinion for International Application No. PCT/US2017/043538, dated Jan. 5, 2018, 13 pages.
International Search Report for PCT/US2008/065428, 5 pages, dated Feb. 10, 2009.
International Search Report for PCT/US2013/023404, 4 pages, dated Apr. 15, 2013.
International Search Report for PCT/US2013/055800, 7 pages, dated Mar. 4, 2014.
Jain, et al., "Fully recombinant IgG2a Fc multimers (stradomers) effectively treat collagen-induced arthritis and prevent idiopathic thrombocytopenic purpura in mice." Arthritis Res. Ther. (2012); 14 (4): R192, 12 pages.
Jain, et al., "Tumour antigen targeted monoclonal antibodies incorporating a novel multimerisation domain significantly enhance antibody dependent cellular cytotoxicity against colon cancer." European Journal of Cancer (2013); 49 (15): 3344-3352.
Jefferis, et al., "Interaction sites on human IgG-Fc for FcγR: current models." Immunol. Lett. (2002); 82 (1-2):57-65.
Kacskovics, et al., "Fc receptors in livestock species." Vet. Immunol. Immunopathol. (2004); 102: 351-362.
Landschulz, et al., "The Leucine Zipper: A Hypothetical Structure Common to a New Class of DNA Binding Proteins." Science (1988); 240: 1759-1764.
Lee, J. K. "Determination of the Molecular Size Distribution of Immunoglobulin G (IgG) in Intravenous IgG-Albumin Formulations by High-Performance Liquid Chromatography." Journal of Chromatography (1988); 444: 141-152.
Lemieux and Bazin, "Autoantibody-Induced Formation of Immune Complexes in Normal Human Serum." Curr. Pharm Design (2006); 12: 173-179.
Levinson, D. R., "Intravenous Immune Globulin: medicare payment and availability." Report to DHHS, OEI-03-05-00404 (2007).
Liew, "TH1 and TH2 cells: a historical perspective." Nature Reviews, Immunology (2002);2: 55-60.
Liu and May, "Disulfide bond structures of IgG molecules." mAbs (Jan.-Feb. 2012); 4(1): 17-23. Epub Jan. 1, 2012.
Lucas, et al., "ERK activation following macrophage FcγR ligation leads to chromatin modifications at the IL-10 locus." Journal of Immunology (2005); 175: 469-477.
Lund, et al., "Multiple binding sites on the CH2 domain of IgG for mouse Fc gamma R11." Mol Immunol. (Jan. 1992); 29(1): 53-59.
Lund, et al., "Multiple Interactions of IgG with Its Core Oligosaccharide Can Modulate Recognition by Complement and Human Fcγ Receptor I and Influence the Synthesis of Its Oligosaccharide Chains." J. Immunol. (1996); 157: 4963-4969.
Meijer, et al., "Pharmacokinetics of Murine Anti-Human CD3 Antibodies in Man Are Determined by the Disappearance of Target Antigen." Journal of Pharmacology and Experimental Therapeutics (2002); 300 (1): 346-353.
Mekhaiel, et al., "Polymeric human Fc-fusion proteins with modified effector functions." Scientific Reports (2011); 1: 124, pp. 1-11.
Mendel and Mendel, "'Non-specific' binding. The problem, and a solution." Biochemical Journal (1985); 228 (1): 269-272.
Mihaesco and Seligmann, "Papain Digestion Fragments of Human IGM Globulins." Journal of Experimental Medicine (1968); 127 (3): 431-453.
Mimoto, et al., Engineered antibody Fc variant with selectively enhanced FcγRIIb binding over both FcγRIIa$^{R131}$ and FcγRIIa$^{H131}$. Protein Engineering, Design and Selection (2013); 26 (10): 589-598.
Mimura, et al., "Role of Oligosaccharide Residues of IgG1-Fc in FcγRIIb Binding." Journal of Biological Chemistry (Sep. 2001); 276(49): 45539-45547.
Monoclonal antibody 13-1 heavy chain-mouse, GenBank Accession # PC4436 (Date: Feb. 4, 1998).
Moore, et al., "Engineered Fc variant antibodies with enhanced ability to recruit complement and mediate effector functions." mAbs (2010); 2: 2, 181-189.
Morris, et al., "Development and characterization of recombinant human Fc:OX4OL fusion protein linked via a coiled-coil trimerization domain." Molecular Immunology (2007); 44 (12): 3112-3121.
Mosser, D. M., "The Many Faces of Macrophage Activation." J. Leukocyte Biology (2003); 73: 209-212.
Mosser, et al., "Interleukin-10: new perspectives on an old cytokine." Immunological Reviews (2008); 226 (1): 205-218.
Mössner, et al., "Increasing the efficacy of CD20 antibody therapy through the engineering of a new type II anti-CD20 antibody with enhanced direct and immune effector cell-mediated B-cell cytotoxicity." Blood (2010); 115 (22): 4393-4402.
Nagashima, et al., "Enhanced antibody-dependent cellular phagocytosis by chimeric monoclonal antibodies with tandemly repeated Fc domains." Journal of Bioscience and Bioengineering (2011); 111 (4): 391-396.
Nagashima, et al., "Fc Taryotaika ni yoru Kokassei Kotai." Proc. 126th Ann. Meet. Pharm. Soc. Japan 126:107 (abstract No. P28[S]am-551) (2006).
Nagashima, et al., "Tandemly repeated Fc domain augments binding avidities of antibodies for Fcγ receptors, resulting in enhanced antibody-dependent cellular cytotoxicity." Mol. Immunol. (2008); 45: 2752-2763.
Ngo, et al., "Computational complexity, protein structure prediction, and the levinthal paradox," in the Protein Folding Problem and Tertiary Structure Prediction, Boston: Birkhauser, pp. 433 and 492-495 (1994).
Nimmerjahn and Ravetch, "The antiinflammatory activity of IgG: the intravenous IgG paradox." Journal of Experimental Medicine (2007); 204 (1): 11-15.
Nimmerjahn and Ravetch, "Antibody-mediated modulation of immune responses." Immunological Rev. (2010); 236: 265-275.
Ong, et al., "How to accelerate the endothelialization of stents." Archives de maladies du coeur et des vaisseaux (2005); 98 (2): 123-126.
Opposition Proceedings No. 2012392760, Notice of Opposition filed by Gliknik, Inc. on Oct. 2, 2018, in Australian Patent Application No. 2012392760 in the name of Liverpool School of Tropical Medicine, 2 pages.
Opposition Proceedings No. 2012392760, Statement of Grounds and Particulars of Opposition filed by Gliknik, Inc. on Jan. 2, 2019, in Australian Patent Application No. 2012392760 in the name of Liverpool School of Tropical Medicine, 11 pages.
O'Shea, et al., "Evidence that the leucine zipper is a coiled coil." Science (1989); 243 (4890): 538-542.
Oyama, et al., "A Case of Autoimmune-Related Retinopathy and Optic Neuropathy Syndrome Treated by Autologous Nonmyeloablative Hematopoietic Stem Cell Transplantation." Journal of Neuro-Ophthalmology (2009); 29 (1): 43-49.
Partial European Search Report, EP appl. No. 13169230.3, dated Jul. 31, 2013, 8 pages.
Proceedings of the 126th Annual Meeting of the Pharmaceutical Society of Japan, No. 126 2006, p. 107 (P28[S]am-551) (and Machine translation of pertinent portions), 4 pages.
Ratcliffe et al., "Measurement of the binding activity of defined IgG aggregates to macrophage Fc receptors," Immunology Letters, 7(2):73-76 (1983).

(56) References Cited

OTHER PUBLICATIONS

Reeck, et al., ""Homology" in proteins and nucleic acids: a terminology muddle and a way out of it." Cell (Aug. 1987); 50(5): 667.
Reeth et al., "Positive selection vectors to generate fused genes for the expression of his-tagged proteins." BioTechniques (1998); 25: 898-904.
Reff and Heard, "A review of modifications to recombinant antibodies: attempt to increase efficacy in oncology applications." Crit. Rev. Oncol./Hematol. (2001); 40: 25-35.
Reid and Porter, "Subunit composition and structure of subcomponent C1q of the first component of human complement." Biochemical Journal (1976); 155 (1): 19-23.
Rudikoff, et al. "Single amino acid substitution altering antigen-binding specificity." Proceedings of the National Academy of Sciences (1982); 79.6: 1979-1983.
Salfield, "Isotype selection in antibody engineering." Nat. Biotechnol. (2007); 25: 1369-1372.
Samuelsson, A., et al., "Anti-inflammatory Activity of IVIG Mediated Through the Inhibitory Fc Receptor." Science (Jan. 2001); 291(5503): 484-486.
Saphire, et al., "Crystal structure of a neutralizing human IGG against HIV-1: a template for vaccine design." Science (Aug. 2001); 293(5532): 1155-1159.
Saphire, et al., "Crystallization and preliminary structure determination of an intact human immunoglobulin, b12: an antibody that broadly neutralizes primary isolates of HIV-1." Acta Cryst. (2001); D57: 168-171.
Sazinsky, et al., "Aglycosylated immunoglobulin $G_1$ variants productively engage activating Fc receptors." PNAS (2008); 105 (51): 20167-20172.
Schuurman, et al., "The inter-heavy chain disulfide bonds of IgG4 are in equilibrium with intra-chain disulfide bonds." Mol. Immunol. (2001); 38: 1-8.
Shields, et al., "High Resolution Mapping of the Binding Site on Human IgG1 for FcγRI, FCγRII, FCγRIII, and FcRn and Design of IgG1 Variants with Improved Binding to the FcγR*," J. Biol. Chem. (2001); 276: 6591-6604.
Shields, et al., "Lack of Fucose on Human IgG1 N-Linked Oligosaccharide Improves Binding to Human FcγRIII and Antibody-dependent Cellular Toxicity." The Journal of Biological Chemistry (2002); 277 (30): 26733-26740.
Siragam, et al., "Can antibodies with specificity for soluble antigens mimic the therapeutic effects of intravenous IgG in the treatment of autoimmune disease?" The Journal of Clinical Investigation (2005); 115 (1): 155-160.
Siragam, et al., "Intravenous immunoglobulin ameliorates ITP via activating Fcγ receptors on dendrite cells." Nature Med. (2006); 12(6):668-692.
Smith and Morrison, "Recombinant polymeric IgG: an approach to engineering more potent antibodies." Biotechnol. (1994); 12: 683-688.
Smith, et al., "Addition of a μ-tailpiece to IgG results in polymeric antibodies with enhanced effector functions including complement-mediated cytolysis by IgG4." J. Immunol. (1995); 154: 2226-2236.
Song, et al., "Monoclonal IgG can ameliorate immune thrombocytopenia in a murine model of ITP: an alternative to IVIG." Blood (2002); 101 (9): 3708-3713.
Sørensen, et al., "Effect of the IgM and IgA secretory tailpieces on polymerization and secretion of IgM and IgG." The Journal of Immunology (Apr. 1996); 156(8): 2858-2865.
Stegall, et al., "Terminal Complement Inhibition Decreases Antibody-Mediated Rejection in Sensitized Renal Transplant Recipients." American Journal of Transplantation (2011); 11 (11): 2405-2413.
Stevenson, G. T. et al., "Engineered antibody for treating lymphoma." Recent Res. Canc. Res. (2002); 159: 104-112.
Sundaram, et al., "Lipopolysaccharide-induced suppression of erythrocyte binding and phagocytosis via FcγRI, FcγRII, FcγRIII, and CR3 receptors in murine macrophages." J. Leukocyte Biology (1993); 54: 81-88.

Supplemental European Search Report for European Application No. 08769936.9, dated May 26, 2010, 9 pages.
Supplemental European Search Report for European Application No. 11813204.2, dated Jul. 3, 2015, 6 pages.
Supplemental European Search Report for European Application No. 13741129.4, dated Nov. 4, 2015, 5 pages.
Sutterwala, et al., "Reversal of Proinflammatory Responses by Ligating the macrophage Fcγ Receptor Type I." Journal of Experimental Medicine (1998); 188 (1): 217-222.
Sutterwala, et al., "Selective Suppression of Interleukin-12 Induction After Macrophage Receptor Litigation." J. Exp. Med. (1985); 185: 1977-1985.
Tai, et al., "Potent in vitro and in vivo activity of an Fc-engineered humanized anti-HM1.24 antibody against multiple myeloma via augmented effector function." Blood (2012); 119 (9): 2074-2082.
Tankersley, D. L., "Dimer Formation in immunoglobulin Preparations and Speculations on the Mechanism of Action of Intravenous Immune Globulin in Autoimmune Diseases." Immunological Reviews (1994); 39: 159-172.
Teeling, et al., "Therapeutic efficacy of intravenous immunoglobulin preparations depends on the immunoglobulin G dimers: studies in experimental immune thrombocytopenia." Blood (2001); 98 (4): 1095-1099.
Tha-In, et al., "Modulation of the cellular immune system by intravenous immunoglobulin." Trends Immunol. (2008); 29 (12): 608-615.
Thiruppathi, et al., "Recombinant IgG2a Fc (M045) multimers effectively suppress experimental autoimmune myasthenia gravis." J. Autoimmunity (2014); 52 (2): 64-73.
Tremblay, et al., "Picogram doses of lipopolysaccharide exacerbate antibody-mediated thrombocytopenia and reduce the therapeutic efficacy of intravenous immunoglobulins in mice." British Journal of Hematology (2007); 139: 297-302.
Turhan, et al., "Intravenous immune globulin prevents venular vaso-occlusion in sickle cell mice by inhibiting leukocyte adhesion and the interactions between sickle erythrocytes and adherent leukocytes." Blood (2004); 103: 2397-2400.
Vajdos, et al. "Comprehensive functional maps of the antigen-binding site of an anti-ErbB2 antibody obtained with shotgun scanning mutagenesis." Journal of Molecular Biology (2002); 320 (2): 415-428.
Van Noort and Amor, "Cell Biology of Autoimmune Diseases." International Review of Cytology (1998); 178: 127-205.
Vialtel, et al., "Nucleation-controlled Polymerization of human Monoclonal Immunoglobulin G Cryoglobulins." The Journal of Biological Chemistry (1982); 257 (7): 3811-3818.
Vidarsson, et al., "IgG subclasses and allotypes: from structure to effector functions." Frontiers in Immunology (2014); 5 (1): 1-17.
Weber, et al., "B-cell activation influences T-cell polarization and outcome of anti-CD20 B-cell depletion in central nervous system autoimmunity." Annals of Neurology (2010); 68 (3): 369-383.
Wei, Xiaoshan et al., "Proteomics studies of autoimmune diseases of the nervous system." Journal of Apoplexy and Nervous Diseases (2009); vol. 26, No. 5, pp. 630-632, and English summary / abstract, 4 pages.
White, D.M., et al., "Design and expression of polymeric immunoglobulin fusion proteins: a strategy for targeting low-affinity Fc gamma receptors." Protein Expression and Purification (Apr. 2001); 21(3): 446-455.
Woof, et al., "Human antibody-Fc receptor interactions illuminated by crystal structures." Nat Rev Immunol. (Feb. 2004); 4(2): 89-99.
Wright and Morrison, "Effect of C2-Associated Carbohydrate Structure on Ig Effector Function: Studies with Chimeric Mouse-Human IgG1 Antibodies in Glycosylation Mutants of Chinese Hamster Ovary Cells." The Journal of Immunology (1998); 160 (7): 3393-3402.
Wright, et al., "Dimeric, Trimeric and Tetrameric Complexes of Immunoglobulin G Fix Complement." Biochem. J. (1980); 187: 775-780.
Written Opinion of the International Searching Authority, PCT appln. No. PCT/US2008/065428, 7 pages, dated Feb. 11, 2009.
Written Opinion of the International Searching Authority, PCT appl. No. PCT/US2013/023404, 16 pages, dated Apr. 15, 2013.

(56) References Cited

OTHER PUBLICATIONS

Written Opinion of the International Searching Authority, PCT appl. No. PCT/US2013/0055800, 22 pages, dated Mar. 4, 2014.
Wu, et al., "Structural basis for enhanced neutralization of HIV-1 by a dimeric IgG form of the glycan-recognizing antibody 2G12." Cell Rep. (Dec. 2013); 5(5): 1443-1455.
Yoo, et al. "Human IgG2 can form covalent dimers." The Journal of Immunology (2003); 170 (6): 3134-3138.
Zang, C., "Annual founders week deemed a 'huge success,'" VOICE University of Maryland, pp. 1-5, http://umvoice.com/2011/12/annual-founders-week-deemed-a-huge-success/, visited website Dec. 10, 2012.
Zhang, et al., "Alteration in the IL-2 signal peptide affects secretion of proteins in vitro and in vivo." Journal Gene Medicine (2005); 7: 354-365.
Zhang, et al., "Dynamic and transient remodeling of the macrophages IL-10 promoter during transcription." Journal of Immunology (2006); 177: 1282-1288.
De Jong, et al., "A Novel Platform for the Potentiation of Therapeutic Antibodies Based on Antigen-Dependent Formation of IgG Hexamers at the Cell Surface". PLoS Biol. (Jan. 6, 2016); 14(1):e1002344. eCollection Jan. 2016.
Extended European Search Report for European Patent Application No. 17810971.6, dated Dec. 16, 2019, 8 pages.
Extended European Search Report for European Patent Application No. 17832021.4, dated Feb. 26, 2020, 11 pages.
Opposition Proceedings No. 2012392760 (Australian Patent Application No. 2012392760 in the name of Liverpool School of Tropical Medicine) filed by Gliknik, Inc. on Jan. 2, 2019, Evidence in Answer in Opposition, Declaration of Anthony Lawrence Shaw (and exhibits ALS-18 and ALS-19 and exhibits ALS-18 and ALS-19) dated and filed Sep. 4, 2019, 14 pages.
Opposition Proceedings No. 2012392760 (Australian Patent Application No. 2012392760 in the name of Liverpool School of Tropical Medicine) filed by Gliknik, Inc. on Jan. 2, 2019, Applicant's Evidence in Answer, Declaration of Sarah Cox (and Exhibit SC1), dated Jul. 2, 2019, and filed Jul. 3, 2019, 36 pages.
Opposition Proceedings No. 2012392760 (Australian Patent Application No. 2012392760 in the name of Liverpool School of Tropical Medicine) filed by Gliknik, Inc. on Jan. 2, 2019, Applicant's Evidence in Answer, Declaration of Dr Beate Peter (and Exhibits BP1-BP9) dated Jul. 2, 2019, and filed Jul. 3, 2019, 147 pages.
Spirig, et al., "rIgG1 Fc Hexamer Inhibits Antibody-Mediated Autoimmune Disease via Effects on Complement and FcgRs". J Immunol. (Apr. 15, 2018); 200(8): 2542-2553. Epub Mar. 12, 2018.
Subedi and Barb, "The Structural Role of Antibody N-Glycosylation in Receptor Interactions". Structure (Sep. 1, 2015); 23(9): 1573-1583. Epub Jul. 23, 2015.
Wang, et al., "Molecular Basis of Assembly and Activation of Complement Component C1 in Complex with Immunoglobulin G1 and Antigen". Mol Cell. (Jul. 7, 2016); 63(1): 135-145. Epub Jun. 16, 2016.
Chen, et al., "Fusion protein linkers: Property, design and functionality". Advanced Drug Delivery Reviews (Oct. 15, 2013); 65(10); 1357-1369.
De Taeye, et al., "The Ligands for Human IgG and Their Effector Functions ". Antibodies (2019); 8(2): 30, 18 pages.
Maeda, et al., "Engineering of Functional Chimeric Protein G-Vargula Luciferase". Analytical Biochemistry (Jul. 1, 1997); 249(2): 147-152.
Orlando, M., "Modification of proteins and low molecular weight substances with hydroxyethyl starch (HES)", Inaugural Dissertation, Giesen, 2003, 191 pages.

\* cited by examiner

FIG. 1

CCVECPPCP   SEQ ID NO: 43 (portion of IgG2 hinge)

CCVECPPCP
236   240      Cysteine positions in the IgG2 hinge
 237    243

FIG. 2

CCVECPPCP
│ │ │   │
CCVECPPCP      OR

SCDKTHTCPPCP (Band 2 configuration)

CCVECPPCP    SEQ ID NO: 43 (portion of IgG2 hinge)
│ │ │   │
CCVECPPCP    SEQ ID NO: 43

SCDKTHTCPPCP    SEQ ID NO: 44 (portion of IgG1 hinge)

SCDKTHTCPPCP

CCVECPPCP
│ │ │   │           OR
CCVECPPCP

SCDKTHTCPPCP (Band 3 configuration)

SCDKTHTCPPCP    SEQ ID NO: 44

CCVECPPCP    SEQ ID NO: 43
│ │ │   │
CCVECPPCP    SEQ ID NO: 43

SCDKTHTCPPCP    SEQ ID NO: 44
  <u>5</u>       <u>11</u>  <u>14</u>   Cysteine positions IgG1 Hinge

6 – GL2045
7 – G895
8 – G896
9 – G897

1 – G1057
2 – G1059
3 – GL-2045
4 – G1060
5 – G1062

1 – GL2045
2 – G856
3 – G857
4 – G858
5 – G859

1 – GL2045 (AC)
2 – G948 #1
3 – G948 #2
4 – G949 #5
5 – G899

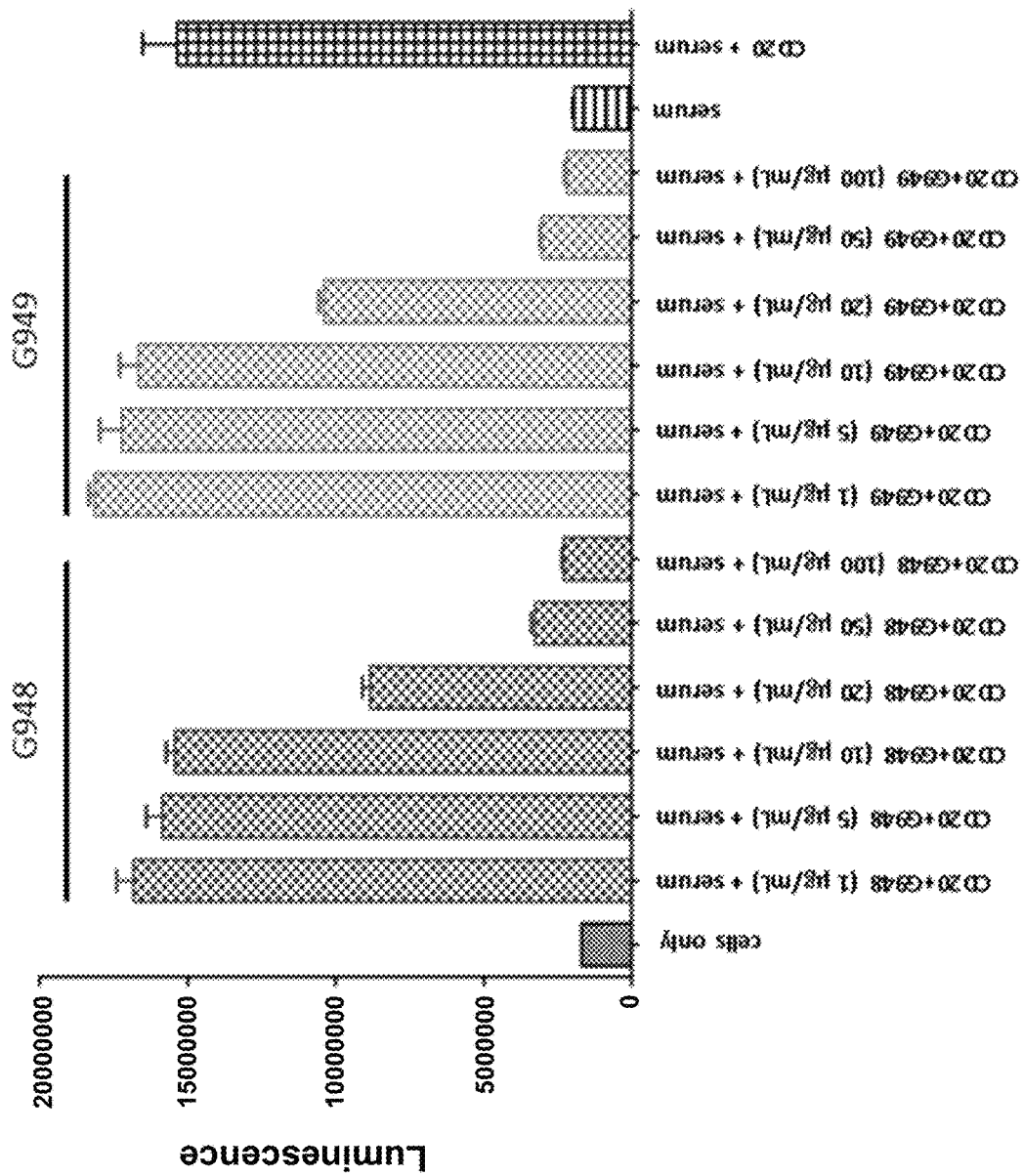

SEQUENCE LISTING

```
<160> NUMBER OF SEQ ID NOS: 44

<210> SEQ ID NO 1
<211> LENGTH: 20
<212> TYPE: PRT
<213> ORGANISM: Artificial Sequence
<220> FEATURE:
<223> OTHER INFORMATION: leader sequence

<400> SEQUENCE: 1

Met Glu Thr Asp Thr Leu Leu Leu Trp Val Leu Leu Leu Trp Val Pro
1               5                   10                  15

Gly Ser Thr Gly
            20

<210> SEQ ID NO 2
<211> LENGTH: 232
<212> TYPE: PRT
<213> ORGANISM: Homo sapiens

<400> SEQUENCE: 2

Glu Pro Lys Ser Cys Asp Lys Thr His Thr Cys Pro Pro Cys Pro Ala
1               5                   10                  15
```

```
Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 3
<211> LENGTH: 40
<212> TYPE: PRT
<213> ORGANISM: Homo sapiens

<400> SEQUENCE: 3

Gly Gly Gly Ser Ile Lys Gln Ile Glu Asp Lys Ile Glu Glu Ile Leu
1               5                   10                  15

Ser Lys Ile Tyr His Ile Glu Asn Glu Ile Ala Arg Ile Lys Lys Leu
            20                  25                  30

Ile Gly Glu Arg Gly His Asp Ile
        35                  40

<210> SEQ ID NO 4
<211> LENGTH: 38
<212> TYPE: PRT
<213> ORGANISM: Homo sapiens

<400> SEQUENCE: 4

Gly Gly Gly Ser Ile Lys Gln Ile Glu Asp Lys Ile Glu Glu Ile Leu
1               5                   10                  15

Ser Lys Ile Tyr His Ile Glu Asn Glu Ile Ala Arg Ile Lys Lys Leu
            20                  25                  30

Ile Gly Glu Arg Gly His
        35

<210> SEQ ID NO 5
<211> LENGTH: 34
```

```
<212> TYPE: PRT
<213> ORGANISM: Homo sapiens

<400> SEQUENCE: 5

Ile Lys Gln Ile Glu Asp Lys Ile Glu Glu Ile Leu Ser Lys Ile Tyr
1               5                   10                  15
His Ile Glu Asn Glu Ile Ala Arg Ile Lys Lys Leu Ile Gly Glu Arg
            20                  25                  30
Gly His

<210> SEQ ID NO 6
<211> LENGTH: 36
<212> TYPE: PRT
<213> ORGANISM: Homo sapiens

<400> SEQUENCE: 6

Gly Gly Gly Ser Ile Lys Gln Ile Glu Asp Lys Ile Glu Glu Ile Leu
1               5                   10                  15
Ser Lys Ile Tyr His Ile Glu Asn Glu Ile Ala Arg Ile Lys Lys Leu
            20                  25                  30
Ile Gly Glu Arg
        35

<210> SEQ ID NO 7
<211> LENGTH: 32
<212> TYPE: PRT
<213> ORGANISM: Homo sapiens

<400> SEQUENCE: 7

Ile Lys Gln Ile Glu Asp Lys Ile Glu Glu Ile Leu Ser Lys Ile Tyr
1               5                   10                  15
His Ile Glu Asn Glu Ile Ala Arg Ile Lys Lys Leu Ile Gly Glu Arg
            20                  25                  30

<210> SEQ ID NO 8
<211> LENGTH: 12
<212> TYPE: PRT
<213> ORGANISM: Homo sapiens

<400> SEQUENCE: 8

Glu Arg Lys Cys Cys Val Glu Cys Pro Pro Cys Pro
1               5                   10

<210> SEQ ID NO 9
<211> LENGTH: 15
<212> TYPE: PRT
<213> ORGANISM: Homo sapiens

<400> SEQUENCE: 9

Glu Pro Lys Ser Cys Asp Lys Thr His Thr Cys Pro Pro Cys Pro
1               5                   10                  15

<210> SEQ ID NO 10
<211> LENGTH: 244
<212> TYPE: PRT
<213> ORGANISM: Homo sapiens

<400> SEQUENCE: 10

Glu Pro Lys Ser Cys Asp Lys Thr His Thr Cys Pro Pro Cys Pro Ala
1               5                   10                  15
Pro Glu Leu Leu Gly Gly Pro Ser Val Phe Leu Phe Pro Pro Lys Pro
            20                  25                  30
```

```
Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
210                 215                 220

Ser Leu Ser Leu Ser Pro Gly Lys Glu Arg Lys Cys Cys Val Glu Cys
225                 230                 235                 240

Pro Pro Cys Pro

<210> SEQ ID NO 11
<211> LENGTH: 15
<212> TYPE: PRT
<213> ORGANISM: Homo sapiens

<400> SEQUENCE: 11

Glu Pro Lys Ser Ser Asp Lys Thr His Thr Cys Pro Pro Cys Pro
1               5                   10                  15

<210> SEQ ID NO 12
<211> LENGTH: 15
<212> TYPE: PRT
<213> ORGANISM: Homo sapiens

<400> SEQUENCE: 12

Glu Pro Lys Ser Cys Asp Lys Thr His Thr Ser Pro Pro Cys Pro
1               5                   10                  15

<210> SEQ ID NO 13
<211> LENGTH: 15
<212> TYPE: PRT
<213> ORGANISM: Homo sapiens

<400> SEQUENCE: 13

Glu Pro Lys Ser Cys Asp Lys Thr His Thr Cys Pro Pro Ser Pro
1               5                   10                  15

<210> SEQ ID NO 14
<211> LENGTH: 217
<212> TYPE: PRT
```

<213> ORGANISM: Homo sapiens

<400> SEQUENCE: 14

```
Ala Pro Glu Leu Leu Gly Gly Pro Ser Val Phe Leu Phe Pro Pro Lys
1               5                   10                  15
Pro Lys Asp Thr Leu Met Ile Ser Arg Thr Pro Glu Val Thr Ser Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
            100                 105                 110
Pro Arg Glu Pro Gln Val Tyr Thr Leu Pro Pro Ser Arg Glu Glu Met
        115                 120                 125
Thr Lys Asn Gln Val Ser Leu Thr Cys Leu Val Lys Gly Phe Tyr Pro
    130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Tyr Ser Lys Leu Thr Val Asp Lys Ser Arg Trp Gln Gln Gly Asn Val
            180                 185                 190
Phe Ser Cys Ser Val Met His Glu Ala Leu His Asn His Tyr Thr Gln
        195                 200                 205
Lys Ser Leu Ser Leu Ser Pro Gly Lys
    210                 215
```

<210> SEQ ID NO 15
<211> LENGTH: 217
<212> TYPE: PRT
<213> ORGANISM: Homo sapiens

<400> SEQUENCE: 15

```
Ala Pro Glu Leu Leu Gly Gly Pro Ser Val Phe Leu Phe Pro Pro Lys
1               5                   10                  15
Pro Lys Asp Thr Leu Met Ile Ser Arg Thr Pro Glu Val Thr Cys Val
            20                  25                  30
Val Val Asp Val Ser His Glu Asp Pro Glu Val Lys Phe Asn Trp Tyr
        35                  40                  45
Val Asp Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Ser Lys Val Ser Asn Lys
                85                  90                  95
Ala Leu Pro Ala Pro Ile Glu Lys Thr Ile Ser Lys Ala Lys Gly Gln
            100                 105                 110
Pro Arg Glu Pro Gln Val Tyr Thr Leu Pro Pro Ser Arg Glu Glu Met
        115                 120                 125
Thr Lys Asn Gln Val Ser Leu Thr Cys Leu Val Lys Gly Phe Tyr Pro
```

```
                130                 135                 140
Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
    210                 215

<210> SEQ ID NO 16
<211> LENGTH: 217
<212> TYPE: PRT
<213> ORGANISM: Homo sapiens

<400> SEQUENCE: 16

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
                100                 105                 110

Pro Arg Glu Pro Gln Val Tyr Thr Leu Pro Pro Ser Arg Glu Glu Met
            115                 120                 125

Thr Lys Asn Gln Val Ser Leu Thr Ser Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
                180                 185                 190

Phe Ser Cys Ser Val Met His Glu Ala Leu His Asn His Tyr Thr Gln
                195                 200                 205

Lys Ser Leu Ser Leu Ser Pro Gly Lys
    210                 215

<210> SEQ ID NO 17
<211> LENGTH: 217
<212> TYPE: PRT
<213> ORGANISM: Homo sapiens

<400> SEQUENCE: 17

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
```

```
                20                  25                  30
Val Val Asp Val Ser His Glu Asp Pro Glu Val Lys Phe Asn Trp Tyr
            35                  40                  45
Val Asp Gly Val Glu Val His Asn Ala Lys Thr Lys Pro Arg Glu Glu
    50                  55                  60
Gln Tyr Asn Ser Thr Tyr Arg Val Val Ser Val Leu Thr Val Leu His
65                  70                  75                  80
Gln Asp Trp Leu Asn Gly Lys Glu Tyr Lys Cys Lys Val Ser Asn Lys
                85                  90                  95
Ala Leu Pro Ala Pro Ile Glu Lys Thr Ile Ser Lys Ala Lys Gly Gln
            100                 105                 110
Pro Arg Glu Pro Gln Val Tyr Thr Leu Pro Pro Ser Arg Glu Glu Met
        115                 120                 125
Thr Lys Asn Gln Val Ser Leu Thr Cys Leu Val Lys Gly Phe Tyr Pro
    130                 135                 140
Ser Asp Ile Ala Val Glu Trp Glu Ser Asn Gly Gln Pro Glu Asn Asn
145                 150                 155                 160
Tyr Lys Thr Thr Pro Pro Val Leu Asp Ser Asp Gly Ser Phe Phe Leu
                165                 170                 175
Tyr Ser Lys Leu Thr Val Asp Lys Ser Arg Trp Gln Gln Gly Asn Val
            180                 185                 190
Phe Ser Cys Ser Val Met His Glu Ala Leu His Asn His Tyr Thr Gln
        195                 200                 205
Lys Ser Leu Ser Leu Ser Pro Gly Lys
    210                 215

<210> SEQ ID NO 18
<211> LENGTH: 12
<212> TYPE: PRT
<213> ORGANISM: Homo sapiens

<400> SEQUENCE: 18

Glu Arg Lys Cys Cys Val Glu Ser Pro Pro Cys Pro
1               5                   10

<210> SEQ ID NO 19
<211> LENGTH: 12
<212> TYPE: PRT
<213> ORGANISM: Homo sapiens

<400> SEQUENCE: 19

Glu Arg Lys Cys Ser Val Glu Cys Pro Pro Cys Pro
1               5                   10

<210> SEQ ID NO 20
<211> LENGTH: 12
<212> TYPE: PRT
<213> ORGANISM: Homo sapiens

<400> SEQUENCE: 20

Glu Arg Lys Ser Cys Val Glu Cys Pro Pro Cys Pro
1               5                   10

<210> SEQ ID NO 21
<211> LENGTH: 12
<212> TYPE: PRT
<213> ORGANISM: Homo sapiens

<400> SEQUENCE: 21
```

```
Glu Arg Lys Cys Cys Val Glu Cys Pro Pro Ser Pro
1               5                   10
```

<210> SEQ ID NO 22
<211> LENGTH: 15
<212> TYPE: PRT
<213> ORGANISM: Homo sapiens

<400> SEQUENCE: 22

```
Glu Pro Lys Ser Cys Asp Lys Thr His Thr Ser Pro Pro Ser Pro
1               5                   10                  15
```

<210> SEQ ID NO 23
<211> LENGTH: 15
<212> TYPE: PRT
<213> ORGANISM: Homo sapiens

<400> SEQUENCE: 23

```
Glu Pro Lys Ser Ser Asp Lys Thr His Thr Cys Pro Pro Ser Pro
1               5                   10                  15
```

<210> SEQ ID NO 24
<211> LENGTH: 15
<212> TYPE: PRT
<213> ORGANISM: Homo sapiens

<400> SEQUENCE: 24

```
Glu Pro Lys Ser Ser Asp Lys Thr His Thr Ser Pro Pro Cys Pro
1               5                   10                  15
```

<210> SEQ ID NO 25
<211> LENGTH: 15
<212> TYPE: PRT
<213> ORGANISM: Homo sapiens

<400> SEQUENCE: 25

```
Glu Pro Lys Ser Ser Asp Lys Thr His Thr Ser Pro Pro Ser Pro
1               5                   10                  15
```

<210> SEQ ID NO 26
<211> LENGTH: 217
<212> TYPE: PRT
<213> ORGANISM: Homo sapiens

<400> SEQUENCE: 26

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125
```

```
Thr Lys Asn Gln Val Ser Leu Thr Ser Leu Val Lys Gly Phe Tyr Pro
        130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
                180                 185                 190

Phe Ser Ser Ser Val Met His Glu Ala Leu His Asn His Tyr Thr Gln
                195                 200                 205

Lys Ser Leu Ser Leu Ser Pro Gly Lys
    210                 215

<210> SEQ ID NO 27
<211> LENGTH: 264
<212> TYPE: PRT
<213> ORGANISM: Homo sapiens

<400> SEQUENCE: 27

Met Glu Thr Asp Thr Leu Leu Leu Trp Val Leu Leu Leu Trp Val Pro
1               5                   10                  15

Gly Ser Thr Gly Glu Pro Lys Ser Ser Asp Lys Thr His Thr Cys Pro
                20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 28
```

```
<211> LENGTH: 264
<212> TYPE: PRT
<213> ORGANISM: Homo sapiens

<400> SEQUENCE: 28

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Ser Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 29
<211> LENGTH: 264
<212> TYPE: PRT
<213> ORGANISM: Homo sapiens

<400> SEQUENCE: 29

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Ser Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80
```

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 30
<211> LENGTH: 264
<212> TYPE: PRT
<213> ORGANISM: Homo sapiens

<400> SEQUENCE: 30

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro

```
            180                 185                 190
Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
            245                 250                 255

Cys Val Glu Ser Pro Pro Cys Pro
            260
```

<210> SEQ ID NO 31
<211> LENGTH: 264
<212> TYPE: PRT
<213> ORGANISM: Homo sapiens

<400> SEQUENCE: 31

```
Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
            115                 120                 125

Ser Asn Lys Ala Leu Pro Ala Pro Ile Glu Lys Thr Ile Ser Lys Ala
        130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
        210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Ser Val Glu Cys Pro Pro Cys Pro
            260
```

<210> SEQ ID NO 32
<211> LENGTH: 264

```
<212> TYPE: PRT
<213> ORGANISM: Homo sapiens

<400> SEQUENCE: 32

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Ser
                245                 250                 255

Cys Val Glu Cys Pro Pro Cys Pro
            260

<210> SEQ ID NO 33
<211> LENGTH: 264
<212> TYPE: PRT
<213> ORGANISM: Homo sapiens

<400> SEQUENCE: 33

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80
```

```
Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Ser Pro
            260

<210> SEQ ID NO 34
<211> LENGTH: 264
<212> TYPE: PRT
<213> ORGANISM: Homo sapiens

<400> SEQUENCE: 34

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Ser Pro
            20                  25                  30

Pro Ser Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190
```

-continued

Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
            245                 250                 255

Cys Val Glu Cys Pro Pro Cys Pro
            260

<210> SEQ ID NO 35
<211> LENGTH: 264
<212> TYPE: PRT
<213> ORGANISM: Homo sapiens

<400> SEQUENCE: 35

Met Glu Thr Asp Thr Leu Leu Leu Trp Val Leu Leu Leu Trp Val Pro
1               5                   10                  15

Gly Ser Thr Gly Glu Pro Lys Ser Ser Asp Lys Thr His Thr Cys Pro
            20                  25                  30

Pro Ser Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
            245                 250                 255

Cys Val Glu Cys Pro Pro Cys Pro
            260

<210> SEQ ID NO 36
<211> LENGTH: 264
<212> TYPE: PRT

<213> ORGANISM: Homo sapiens

<400> SEQUENCE: 36

```
Met Glu Thr Asp Thr Leu Leu Leu Trp Val Leu Leu Leu Trp Val Pro
1               5                   10                  15

Gly Ser Thr Gly Glu Pro Lys Ser Ser Asp Lys Thr His Thr Ser Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Gly Arg Lys Cys
                245                 250                 255

Cys Val Glu Cys Pro Pro Cys Pro
            260
```

<210> SEQ ID NO 37
<211> LENGTH: 264
<212> TYPE: PRT
<213> ORGANISM: Homo sapiens

<400> SEQUENCE: 37

```
Met Glu Thr Asp Thr Leu Leu Leu Trp Val Leu Leu Leu Trp Val Pro
1               5                   10                  15

Gly Ser Thr Gly Glu Pro Lys Ser Ser Asp Lys Thr His Thr Ser Pro
            20                  25                  30

Pro Ser Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
```

```
                85                  90                  95
Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
            115                 120                 125

Ser Asn Lys Ala Leu Pro Ala Pro Ile Glu Lys Thr Ile Ser Lys Ala
            130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 38
<211> LENGTH: 264
<212> TYPE: PRT
<213> ORGANISM: Homo sapiens

<400> SEQUENCE: 38

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
            50                  55                  60

Thr Ser Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
            115                 120                 125

Ser Asn Lys Ala Leu Pro Ala Pro Ile Glu Lys Thr Ile Ser Lys Ala
            130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190
```

Glu Asn Asn Tyr Lys Thr Thr Pro Pro Val Leu Asp Ser Asp Gly Ser
            195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
            245                 250                 255

Cys Val Glu Cys Pro Pro Cys Pro
            260

<210> SEQ ID NO 39
<211> LENGTH: 264
<212> TYPE: PRT
<213> ORGANISM: Homo sapiens

<400> SEQUENCE: 39

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Ser Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 40
<211> LENGTH: 264
<212> TYPE: PRT
<213> ORGANISM: Homo sapiens

<400> SEQUENCE: 40

```
Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Ser Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260
```

<210> SEQ ID NO 41
<211> LENGTH: 264
<212> TYPE: PRT
<213> ORGANISM: Homo sapiens

<400> SEQUENCE: 41

```
Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95
```

```
Arg Glu Glu Gln Tyr Asn Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Ser Asn Lys Ala Leu Pro Ala Pro Ile Glu Lys Thr Ile Ser Lys Ala
        130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260
```

<210> SEQ ID NO 42
<211> LENGTH: 264
<212> TYPE: PRT
<213> ORGANISM: Homo sapiens

<400> SEQUENCE: 42

```
Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Ser Asn Lys Ala Leu Pro Ala Pro Ile Glu Lys Thr Ile Ser Lys Ala
        130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Ser Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
```

```
                195                 200                 205
Phe Phe Leu Tyr Ser Lys Leu Thr Val Asp Lys Ser Arg Trp Gln Gln
        210                 215                 220

Gly Asn Val Phe Ser Ser Val Met His Glu Ala Leu His Asn His
225                 230                 235                 240

Tyr Thr Gln Lys Ser Leu Ser Leu Ser Pro Gly Lys Glu Arg Lys Cys
                245                 250                 255

Cys Val Glu Cys Pro Pro Cys Pro
            260

<210> SEQ ID NO 43
<211> LENGTH: 9
<212> TYPE: PRT
<213> ORGANISM: Homo sapiens

<400> SEQUENCE: 43

Cys Cys Val Glu Cys Pro Pro Cys Pro
1               5

<210> SEQ ID NO 44
<211> LENGTH: 12
<212> TYPE: PRT
<213> ORGANISM: Homo sapiens

<400> SEQUENCE: 44

Ser Cys Asp Lys Thr His Thr Cys Pro Pro Cys Pro
1               5                   10
```

CYSTEINE-OPTIMIZED STRADOMERS

REFERENCE TO RELATED APPLICATIONS

This application is the U.S. national stage to International Patent Application No.: PCT/US2017/036425, filed Jun. 7, 2017, which claims the benefit of priority to U.S. Provisional Application Nos. 62/346,994, filed Jun. 7, 2016 and 62/350,534, filed Jun. 15, 2016, the contents of each of which are each incorporated herein by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: GLIK_016_01WO_SeqList_ST25.txt; date recorded: May 16, 2017; file size: 59 kilobytes).

BACKGROUND

GL-2045 is a stradomer that is in development as a recombinant mimetic of pooled human intravenous immunoglobulin (IVIG). IVIG has been used since the early 1950's to treat immune deficiency disorders and more recently, and more commonly, for autoimmune and inflammatory diseases. IVIG mediates immune tolerogenic effects via several mechanisms, including binding of IVIG aggregates to Complement C1q and Fc gamma receptors (FcγRs) and cross-linking of these receptors on immune cells including NK cells (e.g. FcγRIIIa), macrophages (e.g. FcγRIIa), B cells (e.g. FcγRIIb), and monocytes and monocyte derived cells including dendritic cells.

GL-2045 has various advantages over IVIG (e.g., IVIG is limited by being a pooled blood product). GL-2045 also has potential clinical utility in treating a wide range of autoimmune diseases, including but not limited to idiopathic thrombocytopenic purpura, chronic inflammatory polyneuropathy, multifocal motor neuropathy, myasthenia gravis, organ transplantation, and rheumatoid arthritis. GL-2045 binds with high affinity and avidity to all canonical receptors and to complement C1q, and has been demonstrated to have functional efficacy in vitro at 10-1,000 fold greater potency compared with IVIG.

The amino acid sequences of IgG Fc regions include cysteines that are critical for the tertiary structure of the Fc region. A typical, full IgG1 antibody having two light and two heavy chains contains 4 inter-chain disulfide bonds and 12 intra-chain disulfide bonds. In the IgG1 CH2-CH3 region, there are 4 cysteines that form intra-chain disulfide bonds; and the remaining 8 intra-chain disulfide bonds are in the CL, CH1, variable light, and variable heavy chains. The IgG1 hinge region contains two inter-chain disulfide bonds linking the two heavy chains, and the cysteine residue at position 220 (EU index as in Kabat) links the heavy and light chains by a disulfide bond. The chain linkages differ for other IgGs; for example, in IgG2, IgG3, and IgG4, the cysteine residue at position 131 (EU index as in Kabat) links the heavy and light chains by a disulfide bond. The IgG2 hinge has 4 inter-chain linkages linking the two heavy chains.

Cysteine residues that are not involved in the formation of the tertiary structure are a potential liability, particularly in purified recombinantly-expressed proteins, as those cysteines are subject to chemical modifications. Examples of chemical modifications are non-reducible thioester bond formation and trisulfide bond formation (reviewed in "Disulfide bond structures of IgG molecules Structural variations, chemical modifications and possible impacts to stability and biological function," Hongcheng Liu and Kimberly May mAbs 4:1, 17-23; January/February 2012).

There is therefore a need for improvements to stradomers by reducing the presence of cysteine residues, without reducing the multimerization or function of the stradomer.

SUMMARY OF THE INVENTION

The present disclosure provides stradomers comprising fewer cysteine residues than a corresponding parental stradomer wherein the structure and function of the stradomers are substantially maintained. In some embodiments, the stradomers are multimerized stradomers. In some aspects, the present disclosure provides multimerizing stradomer units comprising at least two multimerizing stradomer unit monomers that each comprise at least one Fc domain monomer and at least one multimerization domain monomer and wherein at least one of the multimerizing stradomer unit monomers comprises at least one point mutation at a cysteine residue. In some embodiments, the IgG1 Fc domain is an IgG1 Fc domain comprising an IgG1 CH2 and an IgG1 CH3 domain. In some embodiments, the IgG1 Fc domain comprises an IgG1 hinge, IgG1 CH2 and an IgG1 CH3 domain. In some embodiments, the multimerization domain is an IgG2 hinge, GPP domain, zinc finger or isoleucine zipper. In some embodiments, the at least one multimerization domain is located on the N-terminus of the Fc domain. In some embodiments, the at least one multimerization domain is located on the C-terminus of the Fc domain.

In one embodiment, the Fc domain comprises an IgG1 Fc domain comprising an IgG1 CH2 domain and an IgG1 CH3 domain and the multimerization domain comprises an IgG2 hinge. In some embodiments, the IgG2 hinge is located on the N-terminus of the IgG1 Fc domain. In some embodiments, the IgG2 hinge is located on the C-terminus of the IgG1 Fc domain. In some embodiments, the IgG1 Fc domain comprises an IgG1 hinge, IgG1 CH2, and IgG1 CH3 domains and the at least one multimerization domain is an IgG2 hinge domain. In some embodiments, the IgG2 hinge domain is located on the N-terminus of the IgG1 Fc domain. In some embodiments, the IgG2 hinge domain is located on the C-terminus of the IgG1 Fc domain.

In some embodiments, the at least one point mutation is at a cysteine residue located in the IgG1 hinge region of the stradomer monomer. In some embodiments, the at least one point mutation is at a cysteine residue located in the IgG1 CH2-IgG1 CH3 region of the stradomer monomer. In some embodiments, the at least one point mutation is at a cysteine residue located in the IgG2 hinge region of the stradomer monomer. In some embodiments, the cysteine-optimized stradomer comprises two or more stradomer units each comprising point mutations at cysteine residues located in two or more of the IgG1 hinge, IgG1 CH2-IgG1 CH3, and IgG2 hinge region of at least one or both of the stradomer unit monomers that comprise the stradomer units.

In some embodiments, the stradomer unit comprises at least two stradomer unit monomers with at least one point mutation at an amino acid position selected from positions 5, 11, 14, 46, 106, 152, 210, 236, 237, 240, and 243 (according to the numbering of present application; see Table 1 for relationship to Kabat) of at least one or both of the at least two stradomer unit monomers. In some embodiments, the stradomer unit comprises at least two stradomer unit monomers with at least two point mutations at amino acid positions selected from positions 5, 11, and 14 of at least one or both of the at least two stradomer unit monomers. In some embodiments, the stradomer unit comprises at least two stradomer unit monomers with point mutations at positions 5, 11, and 14 of at least one or both of the two or more stradomer unit monomers. In some embodiments, the stradomer unit comprises at least two stradomer unit monomers with two point mutations at amino acid positions selected from positions 236, 237, 240, and 243 of at least one or both of the two or more stradomer unit monomers. In some embodiments, the stradomer unit comprises at least two stradomer unit monomers with three point mutations at amino acid positions selected from positions 236, 237, 240, and 243 of at least one or both of the at least two stradomer unit monomers. In some embodiments, the stradomer unit comprises at least two stradomer unit monomers with point mutations at positions 236, 237, 240, and 243 of at least one or both of the at least two stradomer unit monomers. In some embodiments, the stradomer unit comprises at least two stradomer unit monomers with two point mutations at amino acid positions selected from positions 46, 106, 152, and 210 of at least one or both of the at least two stradomer unit monomers. In some embodiments, the stradomer unit comprises at least two stradomer unit monomers with three point mutations at amino acid positions selected from positions 46, 106, 152, and 210 of at least one of the two or more stradomer unit monomers. In some embodiments, the stradomer unit comprises two or more stradomer unit monomers with a point mutation at one or more of amino acid positions 5, 11, 14, 243 of at least one or both of the at least two stradomer unit monomers, and the stradomer unit monomers do not comprise a point mutation at positions 236, 237, or 240 of either or both of the at least two stradomer unit monomers. In some embodiments, the amino acid sequence of the stradomer unit monomers that comprise the stradomer unit is selected from the group consisting of SEQ ID NOs: 27-42.

In some embodiments, the at least one point mutation is a mutation from a cysteine to any other amino acid. In other embodiments, the at least one point mutation is a deletion of the cysteine residue. In other embodiments, the point mutation is a mutation from a cysteine to a serine, alanine, or valine. In particular embodiments, the point mutation is a mutation from a cysteine to a serine. In some embodiments, the stradomer comprises more than one mutation, and each cysteine residue is mutated to an amino acid independently selected from serine, alanine, and valine.

In some embodiments, the number of cysteines present in each stradomer unit monomer of the stradomer unit that make up the stradomers of the current invention is independently selected from 10, 9, 8, 7, 6, 5, or fewer.

In some embodiments, the multimerizing stradomer unit comprises at least one stradomer unit monomer with a fewer number of cysteines relative to a stradomer comprising at least two stradomer unit monomers of SEQ ID NO: 10 and the stradomer unit exhibits increased multimerization relative to a stradomer unit comprising at least two stradomer unit monomers of SEQ ID NO: 10. In some embodiments, the stradomer unit exhibiting increased multimerization relative to a stradomer comprising at least two stradomer unit monomers of SEQ ID NO: 10 also forms multimerized stradomers that exhibit increased functionality relative to a stradomer composed of at least two stradomer units comprising stradomer unit monomers of SEQ ID NO: 10.

In other embodiments, the multimerizing stradomer unit monomers comprises a fewer number of cysteine residues compared to a stradomer unit monomer comprising SEQ ID NO: 10 and exhibits decreased multimerization (i.e. exhibits an increased formation of homodimers relative to a stradomer unit comprising the stradomer unit monomers of SEQ ID NO: 10). In some embodiments, the stradomer unit exhibiting decreased multimerization relative to a stradomer unit comprising at least two stradomer unit monomers of SEQ ID NO: 10 also forms multimerized stradomers that exhibit decreased functionality relative to a stradomer comprising at least two stradomer unit monomers of SEQ ID NO: 10 and the decreased potency is associated with increased safety and improved tolerability as a result of decreased undesired chemical modifications and aggregation relative to a stradomer comprising at least two stradomer unit monomers of SEQ ID NO: 10.

In some aspects, the present disclosure provides methods for treating or preventing inflammatory, autoimmune, or infectious diseases or disorders, comprising administering to a subject in need thereof a stradomer comprising stradomer units that each comprise at least one IgG1 Fc domain and at least one IgG2 hinge, wherein the stradomer units also each comprise at least two stradomer unit monomers comprising at least one point mutation at a cysteine residue in the IgG1 Fc domain or the IgG2 hinge region of at least one of the at least two stradomer unit monomers. In some embodiments, the disease or disorder is selected from hematologic autoimmune conditions such as idiopathic thrombocytopenic purpura and aplastic anemia; neurologic autoimmune conditions such as chronic inflammatory polyneuropathy, multifocal motor neuropathy, and myasthenia gravis; vascular autoimmune conditions such as rejection associated with organ transplantation and Kawasaki disease; and rheumatologic/dermatologic autoimmune conditions such as polymyositis/dermatomyositis, inclusion body myositis, systemic lupus erythematosus, and rheumatoid arthritis. In some embodiments, the subject is a human. In some embodiments, the stradomer is administered to the subject intravenously, subcutaneously, orally, intraperitoneally, sublingually, buccally, transdermally, by subdermal implant, or intramuscularly.

BRIEF DESCRIPTION OF THE FIGURES

FIG. 1 shows disulfide bonding analysis of the GL-2045 homodimer.

FIG. 2 shows disulfide bonding analysis of the GL-2045 dimer and trimer of the homodimer.

FIG. 8A-8C show the CDC activity for G2045 (FIG. 8A), G858 and G859 (FIG. 8B) and G948 and G949 (FIG. 8C). Each stradomer was tested at increasing concentrations: 1 µg/mL, 5 µg/mL, 10 µg/mL, 20 µg/mL, 50 µg/mL, or 100 µg/mL. Cells only (first bar from left on all three of FIG. 8A-8C) or cells plus serum alone (second to last bar from left on all three of FIG. 8A-8C) were used as negative controls. The positive control is shown as the far right (last bar from left) on all three of FIG. 8A-8C, and was cells with anti-CD20 antibody and serum.

DETAILED DESCRIPTION OF THE INVENTION

Figure 3:
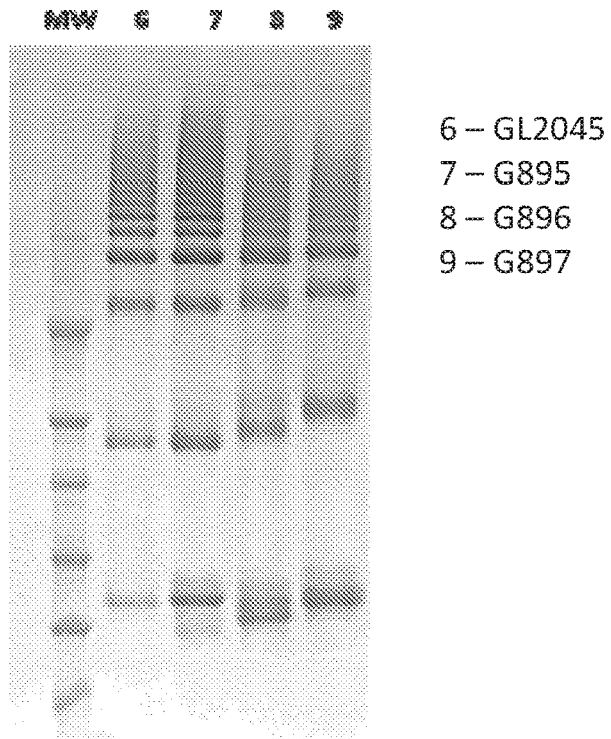
FIG. 3 shows the SDS-PAGE gel of individual cysteine mutations in the IgG1 hinge domain monomer. The SDS-PAGE was run using 4-12% NuPageBT (Invitrogen) for 4 h at 150V in MOPS running buffer.

There is a need in the art for recombinant anti-inflammatory and anti-autoimmune agents. Stradomers were developed for this purpose. Yet the stradomers previously described comprise cysteines that are not involved in the disulfide bond formation to generate either the homodimer or the multimers that form the quaternary structure of this class of stradomers. These free cysteine residues are highly reactive and participate in side chain reactions with other functional groups present in the same protein chain (such as intra-chain disulfide bonds) or with functional groups present in separate, independent protein chains (such as inter-chain or inter-unit disulfide bonds). While these reactions are critical to the formation of the homodimeric stradomer units as well as the formation of multimerized stradomers, the presence of free cysteines may cause unwanted intra- and/or inter-molecular disulfide bond formation. In some instances, these unwanted disulfide bonds can lead to a decrease in the conformational stability of the homodimeric stradomer units and/or the multimerized stradomers, and/or result in unwanted protein oligomerization, the formation of un-ordered aggregates of the homodimeric stradomer units, or non-specific binding to other proteins and other molecules. The cysteine-optimized multimerizing stradomers described herein were thus created to overcome the potential disadvantages of previously described stradomers. The compounds described herein are surprisingly capable of combining the immune tolerance induction that characterizes IVIG and multimerizing stradomers with a reduction in the cysteine content and associated formation of unwanted oxidation reactions, thereby avoiding formation of un-ordered aggregates or non-specific binding to other proteins.

Stradomer Components and Functions

Stradomers are biomimetic compounds that are capable of binding two or more Fc receptors, thereby presenting functional polyvalent Fc to Fc receptors (e.g., low affinity and high affinity canonical FcRs and the neonatal receptor (FcRn)), complement, and other receptors and Fc interacting molecules. Stradomers preferably demonstrate significantly improved binding relative to an Fc domain. Many different physical stradomer conformations have been previously described in U.S. Patent Application Publication Nos. 2010/0239633 and 2013/01516767 and International PCT Publication No. WO 2017/019565. Stradomers (e.g., GL-2045) that bind most or all of the ligands to which immunoglobulin IgG1 Fc binds have been previously disclosed (U.S. Pat. No. 8,690,237 and U.S. Patent Application Publication Nos. 2010-0239633 and 2013-0156765). These stradomer structures include branched and linear designs presenting more than one Fc to Fc receptors; cluster stradomers including the multimerized stradomers of the present invention that present more than one Fc to Fc receptors; and core stradomers including presenting more than one Fc to Fc receptors via attachment of Fc to a core moiety, such as through use of an IgM CH4 domain and/or a J chain. Stradomers that comprise an Fab are referred to herein as "stradobodies" and are described in U.S. Patent Application Publication Nos. 2010-0239633, 2013-0156765, and 2014-0072582. In addition to the ability to presents polyvalent Fc to Fc receptors, complement components, and other components of the immune system, stradobodies have the Fab-targeting (e.g., antigen-specificity) of a monoclonal antibody. Stradobodies may therefore have utility in targeting cancers, infectious diseases, and components of inflammatory pathways.

As used herein, the terms "biomimetic," "biomimetic molecule," "biomimetic compound," and related terms are used herein to refer to a human-made compound that imitates the function of another compound, such as pooled human Intravenous Immunoglobulin (hIVIG), a monoclonal antibody, or the Fc or Fab fragment of an antibody. "Biologically active" biomimetics are compounds which possess biological activities that are the same as or similar to their naturally occurring counterparts. By "naturally occurring" is meant a molecule or portion thereof that is normally found in an organism. By naturally occurring is also meant substantially naturally occurring (e.g. comprise only minor or conservative changes relative to that which is naturally occurring). "Immunologically active" biomimetics are biomimetics which exhibit one or more immunological activities that are the same as or are substantially similar to naturally occurring immunologically active molecules, such as antibodies, cytokines, interleukins, and other immunological molecules known in the art. In some embodiments, the biomimetics of the present invention are cysteine-optimized multimerizing stradomers, as defined herein.

The monomers (e.g., Fc domain monomers, stradomer unit monomers, etc.) of the individual fragments and domains discussed herein are the single chains or arms that must associate with a second chain or arm to form a functional dimeric structure (e.g., Fc domains, stradomer units, etc.). In some embodiments, the functional dimeric structure is a homodimer.

As used herein, "Fc domain" describes the minimum region (in the context of a larger polypeptide) or smallest protein folded structure (in the context of an isolated protein) that can bind to or be bound by one or more FcγR (e.g., FcγRI, FcγRIIA, FcγRIIB, FcγRIIIA, FcγRIIIB and FcγRIV); FcRn; DC-SIGN; SIGN-R1; TRIM21; Dectin-1; Fc Receptor Like Molecules such as FCRL1-6, FCRLA, and FCRLB; and/or complement components C1q, C3, C3a, C3b, C4, or C4a. In both an Fc fragment and an Fc partial fragment, the Fc domain is the minimum binding region that allows binding of the molecule to an Fc receptor. At a minimum, an Fc domain is a dimeric polypeptide (or a dimeric region of a larger polypeptide) that comprises two peptide chains or arms (e.g., Fc domain monomers) that associate to form a functional Fc receptor binding site. Therefore, the functional form of the individual Fc fragments and Fc domains discussed herein generally exist in a dimeric form, generally in homodimeric form. When two such Fc domain monomers associate (e.g., by inter-chain disulfide bonds), the resulting Fc domain has Fc receptor binding activity. Thus, an Fc domain is a dimeric structure (e.g., homodimeric structure) that can bind an Fc receptor.

A homodimeric structure is comprised of two monomers that are homologous to each other. By "homologous" is meant identity over the entire sequence of a given nucleic acid or amino acid sequence. For example, by "80% homologous" is meant that a given sequence shares about 80% identity with the claimed sequence and can include insertions, deletions, substitutions, and frame shifts. In preferred embodiments, the Fc domain monomers comprising the dimeric Fc domain are 100% homologous to each other, thereby forming a homodimeric protein. One of ordinary skill in the art will understand that sequence alignments can be done to take into account insertions and deletions to determine identity over the entire length of a sequence. While an Fc domain can be limited to a discrete homodimeric polypeptide that is bound by an Fc receptor, it will also be clear that an Fc domain can be a part or all of an Fc fragment, as well as part or all of an Fc partial fragment. The term "Fc domains" as used herein will be recognized by a skilled artisan as meaning more than one Fc domain.

"Isolated" refers to a material that is free to varying degrees from components which normally accompany it as found in its native state. "Isolate" denotes a degree of separation from original source or surroundings.

As used herein, "Fc domain monomer" describes the single chain protein that, when associated with another Fc domain monomer, comprises an Fc domain that can bind to an Fcγ receptor. Typically, the association of two Fc domain monomers creates one Fc domain.

As used herein, "Fc partial domain monomer" describes the single chain protein that, when associated with another Fc partial domain monomer, comprises an Fc partial domain. The association of two Fc partial domain monomers creates one Fc partial domain.

The term "Fc region" is used herein to refer to the region of the stradomer that comprises Fc domains and domain linkages. As used herein, a "domain linkage" is a peptide linkage between Fc domain monomers and/or Fc partial domain monomers that does not occur between Fc domain monomers and/or Fc partial domain monomers that are in their natural sequence. The domain linkage may be 1, 2, 3, 4, 5, 6, 7, 8, 9, 10, 11, 12, 13, 14, 15, 16, 17, 18, 19, 20 or more amino acids. Thus, the Fc region of the stradomers described (e.g., cysteine-optimized multimerizing stradomers) herein do not comprise an Fab domain.

As described above, "stradomers" are biomimetic compositions capable of binding to two or more Fc receptors, preferably two or more FcγRs, and can have three physical conformations: serial, cluster, or core. In a preferred embodiment, the stradomers of the present invention are cluster stradomers, also referred to herein as "multimerized stradomers". In the context of a cluster stradomer or multimerized stradomer, the term "stradomer unit" or "multimerizing stradomer unit" refers to a dimeric protein comprised of two monomers (e.g., stradomer unit monomers) that is capable of binding to one or more FcRs (e.g., an FcγR), is capable of multimerization with other stradomer units, and when associated with another stradomer unit is able to bind to two or more FcRs. A stradomer unit that forms a stradomer by some other means (i.e. by use of a core moiety) is simply called a stradomer unit, thus a multimerizing stradomer unit is a type of a stradomer unit that comprises a multimerization domain. A "stradomer unit monomer" refers to a single, contiguous peptide molecule that, when associated with at least a second stradomer unit monomer, forms a stradomer unit comprising at least one Fc domain, and in the context of a multimerized stradomer, at least one multimerization domain. A stradomer unit monomer of a multimerizing stradomer unit is called herein, a "multimerizing stradomer unit monomer."

In general, stradomer units are comprised of two associated stradomer unit monomers; however, a stradomer unit may also comprise three or more stradomer unit monomers. Thus, when referring to stradomer units and homodimeric stradomer units, one of skill in the art will understand that such structures comprising three or more stradomer unit monomers are encompassed by these terms so long as FcγR binding remains substantially intact. In preferred embodiments, a stradomer unit is comprised of two identical stradomer unit monomers (e.g., a homodimer). However, in some embodiments, a stradomer unit may be comprised of two stradomer unit monomers that differ from each other by at least one amino acid residue, such that the resultant stradomer unit is a heterodimeric protein.

In some embodiments, a stradomer unit monomer may have an amino acid sequence that will form one, two, three, four, five, six, seven, eight, nine, ten, eleven, twelve, thirteen, fourteen, fifteen, sixteen, seventeen, eighteen, or more Fc domains when associated with another stradomer unit monomer to form a stradomer unit. A stradomer unit monomer may further have an amino acid sequence that will form one, two, three, four, five, six, seven, eight, nine, ten, eleven, twelve, thirteen, fourteen, fifteen, sixteen, seventeen, eighteen, or more Fc partial domains when associated with another stradomer unit monomer to form a stradomer unit.

As described above, in the context of a multimerized stradomer, the stradomer units comprise at least one Fc domain and at least one "multimerization domain," and are referred to herein as "multimerizing stradomer units." Multimerization domains are amino acid sequences known to cause protein multimerization in the proteins where they naturally occur, examples of which are described in U.S. Patent Application Publication Nos. 2013-0156765 and 2014-0072582, incorporated by reference in their entireties for all purposes. "Multimerization," as used herein, refers to the linking or binding together of multiple (i.e., two or more) individual multimerizing stradomer units, for example to form dimers, trimers, tetramers, pentamers, hexamers, etc. of the multimerizing stradomer units (e.g., to form a multimerized stradomer). In general, the multimerization domains described herein comprise a peptide sequence that causes dimeric proteins (e.g., multimerizing stradomer units) to further multimerize. Examples of peptide multimerization domains include IgG2 hinge, isoleucine zipper, collagen glycine-proline-proline (GPP) repeats, and zinc fingers. In some embodiments, the multimerization domains may be an IgG2 hinge, isoleucine zippers, or a combination thereof. In a particular embodiment, the multimerization domain is an IgG2 hinge.

The term "multimerized stradomer" is used herein to refer to a multimeric compound comprised of two or more multimerizing stradomer units that is capable of binding to at least two FcRs. For example, multimerizing stradomer units are multimerized to form a multimerized stradomer when at least one multimerizing stradomer unit (i.e., at least one homodimeric polypeptide comprising one or more Fc domains and one or more multimerization domains) is attached to at least one other multimerizing stradomer unit via a multimerization domain. The resulting multimerized stradomer may comprise 2, 3, 4, 5, 6, 7, 8, 9, 10, 11, 12, 13, 14, 15, 16, 17, 18, or more multimerizing stradomer units. In particular embodiments, the multimerized stradomers described herein exhibit slow dissociation, characteristic of avidity, from Fcγ-receptors (FcγRs) and/or complement components.

GL-2045 is an exemplary multimerized stradomer that has been previous described (See U.S. Patent Application Publication No. 2013-0156765, incorporated by reference) and is comprised of the EEM polymorphism of human IgG1 Fc and the hinge domain of IgG2. The DEL polymorphism of human IgG1 Fc is structurally and functionally indistinguishable from the EEM polymorphism. The DEL polymorphism of GL-2045 is structurally and functionally indistinguishable from the EEM polymorphism of SEQ ID NO 10. The stradomer unit monomers that make up the multimerizing stradomer units of GL-2045 have the following structure, from N-terminus to C-terminus: IgG1 Hinge—IgG1 CH2 IgG1 CH3-IgG2 Hinge. Thus, GL-2045 is a multimerized stradomer that is capable of binding two or more FcγRs comprising two or more multimerizing stradomer units, each comprising an IgG1 Fc domain and an IgG2 hinge multimerization domain. The amino acid sequence of the stradomer unit monomers that make up the multimerizing stradomer units of GL-2045 is:

(SEQ ID NO: 10)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSREEMTKNQVSL

TCLVKGFYPSDIAVEWESNGQPENNYKTTPPVLDSDGSFFLYSKLTVDKS

RWQQGNVFSCSVMHEALHNHYTQKSLSLSPGKERKCCVECPPCP

In such embodiments, the IgG2 hinge domain of the GL-2045 multimerizing stradomer units serves as a multimerization domain. In some embodiments, GL-2045 can comprise 2, 3, 4, 5, 6, 7, 8, 9, 10 or more of the homodimeric GL-2045 stradomer units that are readily visible by SDS-PAGE and can be separated by size exclusion chromatography.

Cysteine residues play an indispensable role in determining the overall tertiary structure of immunoglobulins and GL-2045 by crosslinking proteins via disulfide bonds, which increase the rigidity of proteins and also confer proteolytic resistance. In the context of a multimerizing stradomer unit, cysteine residues are critical for the formation of intra-chain, inter-chain, and inter-unit disulfide bonds. Herein, "intra-chain" disulfide bonds refer to disulfide bonds that form between cysteine residues present in the same, single-chain protein (e.g., an Fc domain monomer, an Fc partial domain monomer, and/or a stradomer unit monomer) and provide structural support for Fc domain monomers and stradomer unit monomers. "Inter-chain" disulfide bonds, as used herein, refer to the disulfide bonds that form between one cysteine residue present in one protein chain and another cysteine residue present in a different protein chain, for example, a cysteine residue present in one Fc domain monomer and a cysteine residue present in another Fc domain monomer, or a cysteine residue present in one stradomer unit monomer and a cysteine residue present in another stradomer unit monomer. Inter-chain disulfide bonds therefore facilitate the association of two monomers (i.e. two Fc domain monomers or two stradomer unit monomers) into a dimeric protein (i.e., an Fc domain or a stradomer unit). "Inter-unit" disulfide bonds, as used herein, refer to the disulfide bonds that form between two or more of the stradomer units described herein. Inter-unit disulfide bonds therefore determine the overall quaternary structure of the highly ordered multimers of the stradomer units (e.g., the quaternary structure of multimerized stradomers). Thus, as used herein, the term "cysteine optimized stradomer" refers to a stradomer comprised of multimerizing stradomer units wherein one or more cysteine residues in each of the multimerizing stradomer unit monomers that comprise the stradomer units that make up the cysteine-optimized stradomer have been mutated or deleted.

As shown above in SEQ ID NO: 10, each GL-2045 stradomer unit monomer contains 11 cysteine residues located at amino acid positions 5, 11, 14 (located in the IgG1 hinge region of the GL-2045 stradomer unit monomer); 46, 106, 152, 210 (located in the IgG1 CH2-CH3 region of the GL-2045 stradomer unit monomer); and 236, 237, 240, and 243 (located in the IgG2 hinge region of the GL-2045 stradomer unit monomer). The numbering of the cysteine residues contained in the GL-2045 stradomer unit monomers begins at the N-terminal amino acid and continues sequentially throughout the entirety of the GL-2045 stradomer unit monomer protein sequence. One of skill in the art will recognize that the mature protein may be expressed by use of a leader peptide and the numbering provided herein assumes the cleavage of the leader peptide. The correspondence between the numbering of the cysteine residues used herein and that of the EU index as in Kabat (Kabat et al., Sequences of Proteins of Immunological Interest, 5th Ed. Public Health Service, National Institutes of Health, Bethesda, Md. (1991), expressly incorporated herein by references) is shown in Table 1 below. The "EU index as in Kabat" refers to the numbering of the human IgG1 EU antibody and the IgG2 EU antibody.

TABLE 1

Numbering of residues in the present application and the EU Index as in Kabat

| Location of cysteine residue | EU Index | Present Application |
|---|---|---|
| IgG1 hinge | 220 | 5 |
| IgG1 hinge | 226 | 11 |
| IgG1 hinge | 229 | 14 |
| IgG1 CH2—CH3 | 261 | 46 |
| IgG1 CH2—CH3 | 321 | 106 |
| IgG1 CH2—CH3 | 367 | 152 |
| IgG1 CH2—CH3 | 425 | 210 |
| IgG2 hinge | 219 | 236 |
| IgG2 hinge | 220 | 237 |
| IgG2 hinge | 226 | 240 |
| IgG2 hinge | 229 | 243 |

As described above, a native IgG1 CH2-CH3 region monomer comprises 4 cysteines that form intra-chain disulfide bonds. The native IgG1 hinge region monomer comprises 3 cysteines, two of which from inter-chain disulfide bonds linking the two heavy chains. The remaining cysteine residue at position 220 forms an inter-chain disulfide bond linking the heavy and light chains. Cysteine residues that are not involved in the formation disulfide bonds that define the tertiary structure of the IgG1 Fc region can readily form disulfide bonds with other cysteines by oxidation. The other cysteines can be cysteines that would otherwise be involved in the desired disulfide bond formation, or cysteines that bind cysteines in other proteins causing covalently linked aggregate formation (i.e., aggregates of the desired protein that are not highly ordered multimers or aggregates of the stradomer with other unrelated proteins). Thus, in the case of multimerized stradomers (including, for example GL-2045), binding of cysteines that are not involved in the formation of the highly ordered multimers may result in less-ordered, and thus less controlled and less functional, multimers (due to binding that prohibits desired cross-linking), or may result in the formation of undesired aggregates (due to binding with cysteines in other proteins).

The present inventors have previously described, in the context of stradomers that preferentially bind complement, (See International PCT Publication No. WO 2017/019565, incorporated by reference) that mutation of any one of the 4 cysteines in the IgG2 hinge region of a multimerizing stradomer unit monomer may be associated with greatly diminished multimerization of the stradomer. However, it was subsequently, and surprisingly, discovered that in the context of GL-2045, mutation of specific cysteines in the IgG2 hinge region and also in the IgG1 Fc region of one or both of the multimerizing stradomer unit monomers that comprise the stradomer units that multimerize to form GL-2045, can be tolerated without loss of stradomer unit multimerization or stradomer function. It is particularly surprising that specific cysteines that have previously been demonstrated to be involved in the pattern of disulfide bonds in the GL-2045 stradomer unit (e.g., intra-chain and inter-chain disulfide bonds), the dimer of the GL-2045 stradomer unit, or the trimer of the GL-2045 stradomer unit (e.g., inter-unit disulfide bonds) can be mutated without significant loss of stradomer function or structure.

Therefore, in some embodiments, the present disclosure provides compositions and methods for maintaining the multimeric structure of multimerized stradomers thereby preserving the compound's ability to induce immune suppression or tolerance, while eliminating cysteine residues that can be associated with poorly controlled formation of unwanted species such as oxidation of free cysteines in the stradomer with other proteins. In some embodiments, the present disclosure provides compositions and methods for improving the multimeric structure of multimerized stradomers, thereby enhancing the compound's ability to induce immune suppression or tolerance, while eliminating cysteine residues that can be associated with formation of unwanted species.

Cysteine-Optimized Multimerizing Stradomer Unit Structure and Cysteine-Optimized Multimerized Stradomers In some aspects, the present invention provides for cysteine-optimized multimerizing stradomer units and cysteine-optimized multimerized stradomers comprising the same. In some embodiments, the cysteine-optimized multimerizing stradomer units comprise two multimerizing stradomer unit monomers at least one of which is a cysteine-optimized multimerizing stradomer unit monomer comprising at least one point mutation at a cysteine residue relative to the amino acid sequence of a parental stradomer unit. In some cysteine-optimized multimerizing stradomer units comprise two cysteine-optimized multimerizing stradomer unit monomers each comprising at least one point mutation at a cysteine residue relative to the amino acid sequence of a parental stradomer unit.

A "parental stradomer unit" is a stradomer unit from which the cysteine-optimized variants of the present invention are derived and which is not cysteine-optimized (e.g., a non-cysteine optimized multimerizing stradomer unit). A "parental stradomer" is a stradomer comprised of parental stradomer units. In some embodiments, the parental stradomer unit may comprise additional mutations in the IgG1 CH2 and/or IgG1 CH3 domains that are unrelated to the disulfide-bonding pattern of the multimerizing stradomer units. For example, in some embodiments, a parental stradomer unit may be a complement-preferential stradomer unit, such as those described in International PCT Publication No. WO 2017/019565, incorporated by reference. In some embodiments, the at least one point mutation at a cysteine residue is a mutation from cysteine to serine, alanine, or valine. In some embodiments, the at least one point mutation at a cysteine residue comprises a deletion of at least one cysteine residue relative to the amino acid sequence of GL-2045.

In some embodiments, the cysteine-optimized multimerizing stradomer units described herein comprise at least one Fc domain, wherein the at least one Fc domain is an IgG1 Fc domain. In a further embodiment, the IgG1 Fc domain comprises an IgG1 CH2 and IgG1 CH3 domain. In some embodiments, the IgG1 Fc domain comprises an IgG1 hinge, an IgG1 CH2 and an IgG1 CH3 domain. In some embodiments, the cysteine-optimized multimerizing stradomer units of the present invention comprise at least two Fc domains. In some embodiments the cysteine-optimized multimerizing stradomer unit comprises an IgG3 CH2 or IgG3 CH3.

In some aspects, the cysteine-optimized multimerizing stradomer units comprise at least one multimerization domain and at least one Fc domain. As described above, multimerizing stradomer units comprise one or more multimerization domains that function in the formation of multimers of the individual stradomer units to form the multimerized stradomer. For example, cysteine-optimized multimerizing stradomer units are multimerized when at least one cysteine-optimized multimerizing stradomer unit (i.e., at least one homodimeric polypeptide comprising one or more Fc domains and one or more multimerization domains) is attached to at least one other cysteine-optimized multimerizing stradomer unit via a multimerization domain. In some embodiments, the cysteine-optimized multimerizing stradomer unit is comprised of one or more Fc domains and one or more multimerization domains independently selected from the group consisting of an IgG2 hinge, an isoleucine zipper, and a GPP repeat. In some embodiments, the cysteine-optimized multimerizing stradomer unit comprises an isoleucine zipper and one or more Fc domains. In some embodiments, the cysteine-optimized multimerizing stradomer unit comprises an IgG2 hinge and one or more Fc domains. In some embodiments, the cysteine-optimized multimerizing stradomer unit comprises a GPP repeat and one or more Fc domains. In further embodiments, the cysteine-optimized multimerizing stradomer unit comprises an isoleucine zipper, an IgG2 hinge, and one or more Fc domains. In some embodiments, the cysteine-optimized multimerizing stradomer units of the present invention are comprised of one Fc domain and one IgG2 hinge in which one or more cysteines in either or both of the Fc domain(s) and/or one IgG2 hinge has been mutated.

In further embodiments, a cysteine-optimized multimerizing stradomer unit comprises an IgG1 Fc domain comprising an IgG1 CH2 and an IgG1 CH3 domain linked to an IgG2 hinge, wherein specific mutations at one of 11 cysteine residues comprised within one of the at least two stradomer unit monomers have been made. In some embodiments, the IgG2 hinge domain may be linked to the amino or carboxy terminus of the IgG1 Fc domain. In further embodiments, the IgG1 Fc domain further comprises an IgG1 hinge region. In such embodiments, the cysteine-optimized multimerizing stradomer unit retains the ability to form a functional homodimer of the cysteine-optimized stradomer unit monomer and the cysteine-optimized multimerizing stradomer unit retains the ability to form a multimerized stradomer through cysteine binding. In such embodiments, the mutation of non-critical cysteines prevents or reduces oxidation or undesired aggregates. The resultant cysteine-optimized multimerized stradomers further retain some, most, or all of the functionality of the multimerized parental stradomer (e.g., binding to two or more FcγRs and/or inhibition of CDC).

In some embodiments, the cysteine-optimized multimerized stradomers of the present invention are variants of the exemplary parental multimerized stradomer, GL-2045. The multimerizing stradomer units of GL-2045 have the structure: IgG1 Hinge—IgG1 CH2-IgG1 CH3-IgG2 Hinge. As used herein, the terms "IgG1 CH2 IgG1 CH3" and "IgG1 CH2-CH3" and the like are used interchangeably. In some embodiments, the amino acid sequence of the cysteine-optimized multimerizing stradomer unit monomers comprise fewer than 11 cysteines. In some embodiments, the cysteine-optimized multimerizing stradomer units provided herein comprise 10, 9, 8, 7, 6, or fewer cysteines in each of the stradomer unit monomers.

In some embodiments, a cysteine-optimized stradomer unit monomer is generated by introducing a mutation at one or more cysteine residues in the corresponding parental stradomer unit monomer. In a further embodiment, more than one cysteine residue is mutated in the corresponding parental stradomer unit monomer. In a still further embodiment, 2, 3, 4, 5, or more cysteine residues are mutated in the corresponding parental stradomer unit monomer. In some embodiments, the one or more cysteine residues in the corresponding parental stradomer unit monomer are mutated to a serine residue. Serine is a common substitution for cysteine in the art but is not always the closest or most ideal replacement for cysteine. Cysteine is more hydrophobic than serine, and sometimes an alanine or valine, despite the difference in size, is a better substitute in order to retain that hydrophobic character. In some embodiments, an alanine substitution may be preferred over valine due to its smaller size. In some embodiments, one or more cysteine residues in the parental stradomer unit monomer are mutated to alanine or valine. In other embodiments, the one or more point mutations at a cysteine residue is a deletion of the cysteine residue.

In some embodiments, the at least one point mutation of the cysteine-optimized multimerizing stradomer unit monomer is at a cysteine residue in the IgG1 hinge region of a multimerizing stradomer unit monomer. In some embodiments, the cysteine-optimized stradomer comprises stradomer unit monomers comprising two point mutations in the IgG1 hinge region of a multimerizing stradomer unit monomer. In some embodiments, the cysteine-optimized stradomer unit monomer comprises three point mutations in the IgG1 hinge region of a multimerizing stradomer unit monomer.

In some embodiments, the at least one point mutation of the cysteine-optimized multimerizing stradomer unit monomer is at a cysteine residue in the IgG2 hinge region of a multimerizing stradomer unit monomer. In some embodiments, the cysteine-optimized stradomer unit comprises stradomer unit monomers with two or more point mutations in the IgG2 hinge region of a multimerizing stradomer unit monomer. In some embodiments, the cysteine-optimized stradomer unit comprises stradomer unit monomers comprising three or more point mutations in the IgG2 hinge region of a multimerizing stradomer unit monomer. In some embodiments, the cysteine-optimized stradomer unit comprises stradomer unit monomers with four point mutations in the IgG2 hinge region of a multimerizing stradomer unit monomer.

In some embodiments, individual cysteine residues or numerous combinations of the cysteine residues at positions 5, 11, 14, and 243 of the GL-2045 stradomer unit monomer of SEQ ID NO: 10 are mutated to reduce cysteine oxidation and aggregation, and the cysteine residues at positions 236, 237, and 240 are maintained as cysteines.

In some embodiments, the at least one point mutation at a cysteine residue is in the IgG1 CH2-CH3 region of at least one of the GL-2045 stradomer unit monomers that comprise the GL-2045 stradomer unit. In some embodiments, the cysteine-optimized stradomer unit comprises at least one or both stradomer unit monomers with two point mutations in the IgG1 CH2-CH3 region of the GL-2045 stradomer unit monomer. In some embodiments, the cysteine-optimized stradomer unit comprises at least one or both stradomer unit monomers with three point mutations in the IgG1 CH2-CH3 region of the GL-2045 stradomer unit monomer. In some embodiments, the cysteine-optimized stradomer unit comprises at least one or both stradomer unit monomers with four point mutations in the IgG1 CH2-CH3 region of the GL-2045 stradomer unit monomer. It is known in the art that the 4 cysteines of the IgG1 CH2-CH3 region in the context of an intact IgG1 molecule form intra-chain disulfide bonds. These intra-chain bonds result in a functional conformation that allows for the IgG1 Fc domain to bind its targets. Surprisingly, the present inventors have discovered that, in the context of a multimerizing stradomer unit monomer, particularly the GL-2045 stradomer unit monomer, one or more of these 4 cysteines of the IgG1 CH2-CH3 region can be mutated and that the resultant variant multimerizing stradomer unit monomer still retains the ability to form a functional homodimer and the homodimers so formed further retain the ability to form multimerized stradomers. What is more, the resultant cysteine-optimized multimerized stradomers further substantially retain the functionality of the parent multimerized stradomer including, inter alia, binding to two or more FcγRs and/or inhibition of CDC. In some embodiments, the resulting cysteine-optimized multimerizing stradomer units and multimerized stradomers comprised thereof substantially retain the functionality of the parental non-cysteine-optimized multimerizing stradomer unit and multimerized stradomers comprised thereof, yet one or more or both of the stradomer unit monomers that make up the multimerizing stradomer unit have fewer than 4 intra-chain disulfide bonds in the IgG1 CH2-CH3 region of the monomers. In some embodiments, the resulting cysteine-optimized multimerizing stradomer and multimerized stradomers comprised thereof are equally as functional (e.g., forms functional homodimers and binds to two or more FcγRs and/or inhibits CDC) as the parental non-cysteine-optimized multimerizing stradomer unit and multimerized stradomers thereof, yet has fewer than 4 intra-chain disulfide bonds in the IgG1 CH2-CH3 region of one or more or both of the stradomer unit monomers that comprise the multimerizing stradomer unit. In some embodiments, the resulting cysteine-optimized multimerizing stradomer units and multimerized stradomers made thereof are more functional compared with the parental non-cysteine-optimized multimerizing stradomer unit and multimerized stradomers made thereof yet has fewer than 4 intra-chain disulfide bonds in the IgG1 CH2-CH3 region of one or both of the stradomer unit monomer that make up the stradomer unit. In some embodiments, the resulting cysteine-optimized multimerizing stradomer units and multimerized stradomers comprised thereof are less functional compared with the parental non-cysteine-optimized multimerizing stradomer unit and multimerized stradomers thereof and has fewer than 4 intra-chain disulfide bonds in the IgG1 CH2-CH3 region of one or more or both of the stradomer unit monomers that comprise the multimerizing stradomer unit. The cysteine-optimized multimerizing stradomer unit monomers described herein may have 3, 2, or 1 disulfide intra-chain bonds compared with the 4 disulfide intra-chain bonds normally found in the IgG1 CH2-CH3 region of an intact IgG1 Fc domain. Thus, in some embodiments, one or more of the cysteines of the IgG1 CH2-CH3 region in one or more or both multimerizing stradomer unit monomers can be mutated or deleted and retain the ability to form a functional homodimer and the resulting homodimers further retain the ability to form multimerized stradomers. These cysteine-optimized multimerizing stradomer units and multimerized stradomers made thereof further substantially retain the functionality of the parent multimerizing stradomer unit and multimerized stradomers made thereof.

In some embodiments, the cysteine-optimized stradomer comprises cysteine-optimized multimerizing stradomer units that in turn each comprise one or more cysteine-optimized multimerizing stradomer unit monomers that comprise point mutations at cysteine residues in one or more of the IgG1 hinge region, the IgG2 hinge region, and/or the IgG1 CH2-CH3 region of the one or more cysteine-optimized multimerizing stradomer unit monomer.

In some embodiments, the cysteine-optimized stradomer unit and thus the multimerized stradomers comprise a multimerizing stradomer unit monomer sequence selected from the group consisting of SEQ ID NOs: 27-42. In some embodiments, the cysteine-optimized stradomer unit monomer comprises an IgG1 hinge region comprising an amino acid sequence selected from the group consisting of SEQ ID NOs: 11-13 and 22-25. In some embodiments, the cysteine-optimized stradomer unit monomer comprises an IgG2 hinge region comprising an amino acid sequence selected from SEQ ID NOs: 18-21. In some embodiments, the cysteine-optimized stradomer unit monomer comprises an IgG1 CH2-CH3 region monomer comprising an amino acid sequence selected from the SEQ ID NOs: 14-17 and 26.

The cysteine-optimized multimerizing stradomer units may be configured in several configurations as described, for example in U.S. Patent Application Publication No. 2013-0156765, incorporated by reference herein in its entirety. As described above, multimerizing stradomer units contain at least one multimerization domain and at least one Fc domain. The structure, identity and placement of those domains can vary quite substantially. For example, the IgG Fc domain can be, for example an IgG1 or an IgG3 Fc domain or combinations thereof. Further, the IgG Fc domain may comprise all or part of the IgG1 hinge domain in addition to the IgG1 CH2 and CH3 domain, or the IgG1 hinge may be lacking. Further, the multimerization domain, for example, IgG2 hinge domain, may be placed N-terminal to or C-terminal to the one or more IgG Fc domains. A non-limiting list of possible configurations of this basic structure is as follows:

IgG2 hinge-IgG1 hinge-IgG1 CH2-IgG1 CH3
IgG2 hinge-IgG1 CH2-IgG1 CH3
IgG1 hinge-IgG1 CH2-IgG1 CH3-IgG2 hinge
IgG1 CH2-IgG1 CH3-IgG2 hinge From this basic structure, the IgG1 Fc domain regions may each independently be replaced with IgG3 domains, for example. Further, additional IgG Fc domains can be added such that each multimerizing stradomer unit monomer comprises two or more Fc domains.

Similarly, the IgG2 multimerization domain can be exchanged for any multimerization domain known in the art, and additional multimerization domains, including one or more additional IgG2 hinge may be added to any of the compounds described above.

In some embodiments, the cysteine-optimized multimerized stradomer may be structurally similar to the corresponding parental stradomer (e.g. a non-cysteine-optimized multimerized stradomer on which it is based), such as by SDS-PAGE or chromatographically. In further embodiments, the cysteine-optimized multimerized stradomer may be functionally similar to the corresponding parental stradomer (e.g. a non-cysteine-optimized multimerized stradomer on which it is based), such as in binding to canonical FcRs, FcRn, or complement C1q; inhibition of CDC; activity in animal models of disease including but not limited to collagen-induced arthritis, idiopathic thrombocytopenic purpura, experimental autoimmune neuropathy, and experimental autoimmune myasthenia gravis; and/or activity in the treatment of a disease in a subject, such as immune suppression or immune tolerance.

In some embodiments, the cysteine-optimized multimerized stradomer that substantially retains structure and function relative to the non-cysteine-optimized multimerized/parental stradomer is less prone than the non-optimized form to chemical modification (e.g., oxidation of cysteine residues) that can result in the formation of fewer multimers and/or formation of aggregates or other unordered multimer species by cysteine-binding other proteins.

In some embodiments, the cysteine-optimized multimerizing stradomer units exhibit increased multimerization relative to the corresponding parental stradomer units. "Increased multimerization" as used herein refers to an increase in the percentage of stradomer multimers (e.g., dimers of the homodimer, trimers of the homodimer, tetramers of the homodimer, etc.) present prior to purification compared to the percentage of multimers of the parental stradomers when cultured under the same conditions (e.g., media, cell type, temperature, culture time, etc.). In some embodiments, the cysteine-optimized multimerized stradomers exhibit increased percentages of the dimer of the homodimer relative to the corresponding parental stradomer. In some embodiments, the cysteine-optimized multimerized stradomers exhibit increased percentages of the trimer of the homodimer relative to the corresponding parental stradomer. In some embodiments, the cysteine-optimized multimerized stradomers exhibit increased percentages of the tetramer of the homodimer relative to the corresponding parental stradomer. In some embodiments, the cysteine-optimized multimerized stradomers exhibit increased percentages of the pentamer of the homodimer relative to the corresponding parental stradomer. In some embodiments, the cysteine-optimized multimerized stradomers exhibit increased percentages of the hexamer of the homodimer relative to the corresponding parental stradomer.

In some embodiments, the cysteine-optimized multimerizing stradomer units exhibit decreased multimerization relative to the corresponding parental stradomer. "Decreased multimerization" as used herein refers to an decrease in the percentage of stradomer multimers (e.g., dimers of the homodimer, trimers of the homodimer, tetramers of the homodimer, etc.) present prior to purification compared to the percentage of multimers of the parental stradomers when cultured under the same conditions (e.g., media, cell type, temperature, culture time, etc.). Decreased multimerization can also refer to an increase in the percentage of homodimers present prior to purification compared to the parental stradomer. In some embodiments, the cysteine-optimized multimerized stradomers exhibit decreased percentages of the dimer of the homodimer relative to the corresponding parental stradomer. In some embodiments, the cysteine-optimized multimerized stradomers exhibit decreased percentages of the trimer of the homodimer relative to the corresponding parental stradomer. In some embodiments, the cysteine-optimized multimerized stradomers exhibit decreased percentages of the tetramer of the homodimer relative to the corresponding parental stradomer. In some embodiments, the cysteine-optimized multimerized stradomers exhibit decreased percentages of the pentamer of the homodimer relative to the corresponding parental stradomer. In some embodiments, the cysteine-optimized multimerized stradomers exhibit decreased percentages of the hexamer of the homodimer relative to the corresponding parental stradomer.

In some embodiments, cysteine-optimized multimerizing stradomer units and multimerized compounds composed thereof exhibit increased function relative to the corresponding parental stradomer. "Increased function" as used herein refers to an increase in one or more functions of the multimerizing stradomer units and multimerized compounds such as the ability to form homodimers (in the context of multimerizing stradomer units), binding to FcγRs, binding to complement components, and/or inhibition of CDC (in the context of multimerized stradomers). In some embodiments, cysteine-optimized multimerizing stradomer units and multimerized compounds composed thereof exhibit substantially the same or similar function relative to the corresponding parental stradomer. In some embodiments, cysteine-optimized multimerizing stradomer units and multimerized compounds made thereof exhibit decreased function relative to the corresponding parental stradomer. In such embodiments, the cysteine-optimized multimerizing stradomer units and multimerized compounds made thereof with decreased function relative to the corresponding parental stradomer are still capable of exerting a therapeutic effect, and are less prone to chemical modification and unwanted protein aggregation associated with free cysteine residues. In such a case, the cysteine-optimized multimerized stradomers of the present invention may require more drug to be administered for equivalent efficacy relative to the parental compound because of lower potency but the cysteine-optimized multimerizing stradomer is safer and better tolerated as a result of decreased undesired chemical modifications and aggregation.

In some embodiments, the cysteine-optimized multimerizing stradomer units described herein demonstrate decreased formation of un-ordered aggregates or superior conformational stability compared to the corresponding parental multimerizing stradomer units. For example, in some embodiments, the percentage of un-ordered aggregates present in a composition of cysteine-optimized multimerizing stradomer units or multimerized stradomers is 15% or less. In some embodiments, the percentage of un-ordered aggregates present in a composition of cysteine-optimized multimerizing stradomer units or multimerized stradomers is 10%, 5%, 2%, 1% or less. In such embodiments, the decreased formation of un-ordered aggregates or superior conformational stability may result in one or more of the following: (i) a decrease in the off-target effects of the cysteine-optimized multimerized stradomers when administered to a subject or contacted with a cell; (ii) an enhanced safety profile of the cysteine-optimized multimerized stradomers when administered to a subject; (iii) a decrease in the amount of the multimerized stradomers required to achieve a desired therapeutic effect; (iv) more reliable manufacturing processes as a result of less binding variability, as indicated by manufacturing analytical methods; (v) more efficient manufacturing processes as a result of greater flexibility in choice and number of columns and conditions that can be used while maintaining constant amounts of homodimer, dimer, trimer, tetramer, and higher order multimers; and/or (vi) an increase in the amount of time the cysteine-optimized multimerizing stradomer.

In some embodiments, the cysteine-optimized multimerizing stradomer units and multimerized stradomers described herein demonstrate decreased formation of un-ordered aggregated and superior conformational stability compared to the corresponding parental multimerizing stradomer units and multimerized stradomers. The increase in conformational stability and/or decreased aggregate formation may be determined by a number of analytical methods, including but not limited to SDS-PAGE, comparative mass spectrometry, SEC-MALLS (MultiAngle Laser Light Scattering), and Dynamic Light Scattering, wherein the conformational stability and/or aggregate formation of the cysteine-optimized multimerizing stradomer units and multimerized stradomers is directly compared to that of corresponding parental multimerizing stradomer units and multimerized stradomers.

Cysteine-Optimized Multimerizing Stradobodies

In further embodiments, the cysteine-optimized multimerizing stradomer unit further comprises an Fab and is referred to herein as a "cysteine-optimized multimerizing stradobody." Stradobodies have been previously described in U.S. Patent Application Publication Nos. 2010-0239633, 2013-0156765, and 2014-0072582. By virtue of such Fab domains and Fc domains, stradobodies have both antigen binding capacity and Fcγ receptor binding activity. In some embodiments, the Fcγ receptor-binding activity may be due to an ability to bind and cross-link FcγR with an affinity and/or avidity equal to or greater than the Fc portion of a native structure holo-antibody. In some embodiments the Fab comprises a heavy chain and a light chain in which the heavy chain comprises a variable domain and a CH1 domain. Multimerizing stradomer units further comprising an Fab are herein termed multimerizing stradobodies, and have been previously described, for example, in U.S. Patent Publication No. 2014-0072582 and PCT Publication No. WO 2014/031646. In some embodiments, the present disclosure provides a cysteine-optimized multimerizing stradobody.

The term "Fab domain" describes the minimum region (in the context of a larger polypeptide) or smallest protein folded structure (in the context of an isolated protein) that can bind to an antigen. The Fab domain is the minimum binding region of an Fab fragment that allows binding of the molecule to an antigen. "Fab domain" is used interchangeably herein with "Fab". The Fab portion of the stradobody may comprise both a heavy and a light chain. The variable heavy chain and the light chain may be independently from any compatible immunoglobulin such as IgA1, IgA2, IgM, IgD, IgE, IgG1, IgG2, IgG3, or IgG4, and may be from the same or different Ig isotype, but preferably are from the same Ig isotype. The light chains kappa or lambda may also be from different Ig isotypes.

Through the Fab domain, the immunologically active biomimetics of the present invention are capable of binding to one or more antigens. In some embodiments, the immunologically active biomimetics of the present invention are capable of binding to two different antigens, similar to bispecific antibodies. In other embodiments, the immunologically active biomimetics of the present invention are capable of binding to more than two different antigens. The biomimetics of the present invention also possess one or more immune modulating activities of the IgG Fc domain and have at least a first Fc domain capable of binding one or more FcγRs (e.g., FcγRI, FcγRIIA, FcγRIIB, FcγRIIIA, FcγRIIIB and FcγRIV); FcRn; DC-SIGN; SIGN-R1; TRIM21; Dectin-1; Fc Receptor Like Molecules such as FCRL1-6, FCRLA, and FCRLB; or complement components C1q, C3, C3a, C3b, C4, or C4a. In some embodiments, the biomimetics of the present invention possess a second Fc domain capable of binding one or more FcγRs (e.g., one or more of FcγRI, FcγRIIA, FcγRIIB, FcγRIIIA, FcγRIIIB and FcγRIV); FcRn; DC-SIGN; SIGN-R1; TRIM21; Dectin-1; Fc Receptor Like Molecules such as FCRL1-6, FCRLA, and FCRLB; or complement components C1q, C3, C3a, C3b, C4, or C4a. Thus, when multimerized, the immunologically active biomimetics contain at least two dimeric structures, each possessing the ability to bind to one or more antigens, and the ability to bind to one or more FcγRs (e.g., one or more of FcγRI, FcγRIIA, FcγRIIB, FcγRIIIA, FcγRIIIB and FcγRIV); FcRn; DC-SIGN; SIGN-R1; TRIM21; Dectin-1; Fc Receptor Like Molecules such as FCRL1-6, FCRLA, and FCRLB; or complement components C1q, C3, C3a, C3b, C4, or C4a.

The Fab of the cysteine-optimized multimerizing stradobody can be the Fab comprised within any monoclonal antibody. In some embodiments, the Fab of the cysteine-optimized multimerizing stradobody is directed towards a tumor antigen or an antigen involved in autoimmune disease. In further embodiments, the Fab of the cysteine-optimized multimerizing stradobody is directed towards EGFR, HER2/neu, CD3, CD19, CD20, carcinoembryonic antigen (CEA), TNF, TNF-α, TNF-β, IFNγ, IFNα, IFNβ, IL-1, IL-2, IL-4, IL-5, IL-6, IL-8, IL-10, IL-12, IL-13, IL-15, IL-17, or IL-23, Rho(D), Lymphotoxin (LT), Lymphotoxin(3 (LT(3), OX40 Ligand, CTLA-4, PD-1, PD-L1, PD-L2, LAG3, B7-H3, B7-H4, IDO, VISTA, A2aR, GITR, CD52, KIR, CD40 Ligand, CD95/Fas Ligand, CD 27, CD27 Ligand (CD70), CD30 Ligand, CD137/4-1BB Ligand, TRAIL, TRANCE/RANKL, TWEAK/Apo-3, APRIL, BAFF/Blys, LIGHT, TL1A/VEGI, GITR Ligand, EDA-A1, EDA-A2. The Fc isotype of the stradobody can be any Fc, including without limitation IgG1, IgG4, IgG3, or IgG2.

Exemplary Cysteine-Optimized Multimerizing Stradomers

The cysteine-optimized multimerizing stradomer units and multimerized stradomers disclosed herein and provided below are based on non-cysteine-optimized multimerizing stradomer units and multimerized stradomers (e.g., parental stradomers) that have been described, for example, in U.S. Pat. No. 8,690,237, U.S. Patent Application Publication Nos. 2010-0239633 and 2013-0156765, and International PCT Publication No. WO 2017/019565.

TABLE 2

Amino acid sequences of GL-2045 stradomer unit monomers and components of multimerizing stradomer compounds.

| Compound or component | Sequence | SEQ ID NO: |
|---|---|---|
| GL-2045 | EPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQ DWLNGKEYKCKVSNKALPAPIEKTISKAKGQPREPQVYTLPPSREEMT KNQVSLTCLVKGFYPSDIAVEWESNGQPENNYKTTPPVLDSDGSFFLY SKLTVDKSRWQQGNVFSCSVMHEALHNHYTQKSLSLSPGKERKCCVEC PPCP | 10 |
| Leader sequence | METDTLLLWVLLLWVPGSTG | 1 |
| IgG1 Fc | EPKSCDKTHTCPPCPAPELLGGPSVFLFPPKPKDTLMISRTPEVTCVV VDVSHEDPEVKFNWYVDGVEVHNAKTKPREEQYNSTYRVVSVLTVLHQ DWLNGKEYKCKVSNKALPAPIEKTISKAKGQPREPQVYTLPPSREEMT KNQVSLTCLVKGFYPSDIAVEWESNGQPENNYKTTPPVLDSDGSFFLY SKLTVDKSRWQQGNVFSCSVMHEALHNHYTQKSLSLSPGK | 2 |
| ILZ w/ restriction site | GGGSIKQIEDKIEEILSKIYHIENEIARIKKLIGERGH<u>DI</u> | 3 |
| ILZ | GGGSIKQIEDKIEEILSKIYHIENEIARIKKLIGERGH | 4 |
| Modified ILZ | IKQIEDKIEEILSKIYHIENEIARIKKLIGERGH | 5 |
| Modified ILZ | GGGSIKQIEDKIEEILSKIYHIENEIARIKKLIGER | 6 |
| Modified ILZ | IKQIEDKIEEILSKIYHIENEIARIKKLIGER | 7 |
| Native IgG2 Hinge | ERKCCVECPPCP | 8 |
| Native IgG1 hinge | EPKSCDKTHTCPPCP | 9 |

*Restriction site indicated by underlined amino acid residues

TABLE 3

Exemplary cysteine-optimized multimerizing stradomer unit monomers*

| Compound | Amino Acid Sequence of cysteine-optimized stradomer compounds | SEQ ID NO. |
| --- | --- | --- |
| G895 | METDTLLLWVLLLWVPGSTGEPKSSDKTHTCPPCPAPELLGGPSVFLFPPKPKDTLMISRT PEVTCVVVDVSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALHNHYTQK SLSLSPGKERKCCVECPPCP | 27 |
| G896 | METDTLLLWVLLLWVPGSTGEPKSCDKTHTSPPCPAPELLGGPSVFLFPPKPKDTLMISRT PEVTCVVVDVSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALHNHYTQK SLSLSPGKERKCCVECPPCP | 28 |
| G897 | METDTLLLWVLLLWVPGSTGEPKSCDKTHTCPPSPAPELLGGPSVFLFPPKPKDTLMISRT PEVTCVVVDVSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALHNHYTQK SLSLSPGKERKCCVECPPCP | 29 |
| G856 | METDTLLLWVLLLWVPGSTGEPKSCDKTHTCPPCPAPELLGGPSVFLFPPKPKDTLMISRT PEVTCVVVDVSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALHNHYTQK SLSLSPGKERKCCVESPPCP | 30 |
| G857 | METDTLLLWVLLLWVPGSTGEPKSCDKTHTCPPCPAPELLGGPSVFLFPPKPKDTLMISRT PEVTCVVVDVSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALHNHYTQK SLSLSPGKERKCSVECPPCP | 31 |
| G858 | METDTLLLWVLLLWVPGSTGEPKSCDKTHTCPPCPAPELLGGPSVFLFPPKPKDTLMISRT PEVTCVVVDVSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALHNHYTQK SLSLSPGKERKSCVECPPCP | 32 |
| G859 | METDTLLLWVLLLWVPGSTGEPKSCDKTHTCPPCPAPELLGGPSVFLFPPKPKDTLMISRT PEVTCVVVDVSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALHNHYTQK SLSLSPGKERKCCVECPPSP | 33 |
| G899 | METDTLLLWVLLLWVPGSTGEPKSCDKTHTSPPSPAPELLGGPSVFLFPPKPKDTLMISRT PEVTCVVVDVSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALHNHYTQK SLSLSPGKERKCCVECPPCP | 34 |
| G948 | METDTLLLWVLLLWVPGSTGEPKSSDKTHTCPPSPAPELLGGPSVFLFPPKPKDTLMISRT PEVTCVVVDVSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALHNHYTQK SLSLSPGKERKCCVECPPCP | 35 |
| G949 | METDTLLLWVLLLWVPGSTGEPKSSDKTHTSPPCPAPELLGGPSVFLFPPKPKDTLMISRT PEVTCVVVDVSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALHNHYTQK SLSLSPGKERKCCVECPPCP | 36 |
| G930 | METDTLLLWVLLLWVPGSTGEPKSSDKTHTSPPSPAPELLGGPSVFLFPPKPKDTLMISRT PEVTCVVVDVSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALHNHYTQK SLSLSPGKERKCCVECPPCP | 37 |
| G1057 | METDTLLLWVLLLWVPGSTGEPKSCDKTHTCPPCPAPELLGGPSVFLFPPKPKDTLMISRT PEVTSVVVDVSHEDPEVKFNWYVDGVEVHNAKTKPREEQYNSTYRVVSVLTVLHQDWLNGK EYKCKVSNKALPAPIEKTISKAKGQPREPQVYTLPPSREEMTKNQVSLTCLVKGFYPSDIA VEWESNGQPENNYKTTPPVLDSDGSFFLYSKLTVDKSRWQQGNVFSCSVMHEALHNHYTQK SLSLSPGKERKCCVECPPCP | 38 |

TABLE 3-continued

Exemplary cysteine-optimized multimerizing stradomer unit monomers*

| Compound | Amino Acid Sequence of cysteine-optimized stradomer compounds | SEQ ID NO. |
|---|---|---|
| G1058 | METDTLLLWVLLLWVPGSTGEPKSCDKTHTCPPCPAPELLGGPSVFLFPPKPKDTLMISRT<br>PEVTCVVVDVSHEDPEVKFNWYVDGVEVHNAKTKPREEQYNSTYRVVSVLTVLHQDWLNGK<br>EYKSKVSNKALPAPIEKTISKAKGQPREPQVYTLPPSREEMTKNQVSLTCLVKGFYPSDIA<br>VEWESNGQPENNYKTTPPVLDSDGSFFLYSKLTVDKSRWQQGNVFSCSVMHEALHNHYTQK<br>SLSLSPGKERKCCVECPPCP | 39 |
| G1059 | METDTLLLWVLLLWVPGSTGEPKSCDKTHTCPPCPAPELLGGPSVFLFPPKPKDTLMISRT<br>PEVTCVVVDVSHEDPEVKFNWYVDGVEVHNAKTKPREEQYNSTYRVVSVLTVLHQDWLNGK<br>EYKCKVSNKALPAPIEKTISKAKGQPREPQVYTLPPSREEMTKNQVSLTSLVKGFYPSDIA<br>VEWESNGQPENNYKTTPPVLDSDGSFFLYSKLTVDKSRWQQGNVFSCSVMHEALHNHYTQK<br>SLSLSPGKERKCCVECPPCP | 40 |
| G1060 | METDTLLLWVLLLWVPGSTGEPKSCDKTHTCPPCPAPELLGGPSVFLFPPKPKDTLMISRT<br>PEVTCVVVDVSHEDPEVKFNWYVDGVEVHNAKTKPREEQYNSTYRVVSVLTVLHQDWLNGK<br>EYKCKVSNKALPAPIEKTISKAKGQPREPQVYTLPPSREEMTKNQVSLTCLVKGFYPSDIA<br>VEWESNGQPENNYKTTPPVLDSDGSFFLYSKLTVDKSRWQQGNVFSSSVMHEALHNHYTQK<br>SLSLSPGKERKCCVECPPCP | 41 |
| G1062 | METDTLLLWVLLLWVPGSTGEPKSCDKTHTCPPCPAPELLGGPSVFLFPPKPKDTLMISRT<br>PEVTCVVVDVSHEDPEVKFNWYVDGVEVHNAKTKPREEQYNSTYRVVSVLTVLHQDWLNGK<br>EYKCKVSNKALPAPIEKTISKAKGQPREPQVYTLPPSREEMTKNQVSLTSLVKGFYPSDIA<br>VEWESNGQPENNYKTTPPVLDSDGSFFLYSKLTVDKSRWQQGNVFSSSVMHEALHNHYTQK<br>SLSLSPGKERKCCVECPPCP | 42 |

*Positions at which a cysteine has been mutated relative to the GL-2045 stradomer unit monomer sequence are in bold and underlined text.

The skilled artisan will recognize that the specific cysteine-optimized multimerizing stradomer unit monomers described above in Table 3 are exemplary and that other multimerizing stradomer unit monomers with various structures can be cysteine optimized to be similarly useful as the compositions and methods of the present disclosure. For example, the parent compound GL-2019 (described in U.S. Patent Application Publication Nos. US 2010-0239633 and US2013-0156765) or any of the parent compounds described, for example, in WO 2017/019565 may be used as the parental stradomer.

It is understood that the cysteine-optimized multimerizing stradomers disclosed herein can be derived from any of a variety of species. Indeed, Fc domains, or Fc partial domains, in any one biomimetic molecule (e.g., in any cysteine-optimized multimerizing stradomer) of the present invention can be derived from immunoglobulin from more than one (e.g., from two, three, four, five, or more) species. However, they will more commonly be derived from a single species. In some embodiments, the Fc domains of the cysteine-optimized multimerizing stradomers are human. In addition, it will be appreciated that any of the methods disclosed herein (e.g., methods of treatment) can be applied to any species. Generally, the components of a biomimetic applied to a species of interest will all be derived from that species. However, biomimetics in which all the components are of a different species or are from more than one species (including or not including the species to which the relevant method is applied) can also be used.

The specific CH2, and CH3 domains and hinge regions that comprise the Fc domains and Fc partial domains of the cysteine-optimized multimerizing stradomer units of the present invention may be independently selected, both in terms of the immunoglobulin subclass, as well as in the organism, from which they are derived. Accordingly, the cysteine-optimized multimerizing stradomer units disclosed herein may comprise Fc domains and partial Fc domains that independently come from various immunoglobulin types such as human IgG1, IgG2, IgG3, IgG4, IgA1, IgA2, IgD, IgE, and IgM, mouse IgG2a, or dog IgGa or IgGb. Preferably, for human therapeutics the CH2 and CH3 Fc domains of the current invention are of the human IgG1 isotype or human IgG3 isotype. Similarly each Fc domain and partial Fc domain may be derived from various species, preferably a mammalian species, including non-human primates (e.g., monkeys, baboons, and chimpanzees), humans, murine, rattus, bovine, equine, feline, canine, porcine, rabbits, goats, deer, sheep, ferrets, gerbils, guinea pigs, hamsters, bats, birds (e.g., chickens, turkeys, and ducks), fish and reptiles to produce species-specific or chimeric cysteine-optimized multimerizing stradomer molecules.

Individual Fc domains and partial Fc domains may also be humanized. Thus, "humanized" cysteine-optimized multimerizing stradomers may be designed analogous to "humanized" monoclonal antibodies.

Pharmaceutical Compositions

In some embodiments, the present invention provides for compositions of the cysteine-optimized multimerized stradomers described herein. The term "composition" as used herein refers to a formulation of one or more cysteine-optimized multimerized stradomers described herein that is capable of being administered to a subject and/or cell. Typically, formulations include all physiologically acceptable compositions including derivatives and/or prodrugs, solvates, stereoisomers, racemates, or tautomers thereof with any physiologically acceptable carriers, diluents, and/or excipients. A "therapeutic composition" or "pharmaceutical composition" (used interchangeably herein) is a composition of one or more cysteine-optimized multimerized stradomers that capable of is capable of being administered or delivered to a subject and/or cell in order to exert a particular physiological effect (e.g., for the treatment of a particular disease or disorder).

The route of administration of the cysteine-optimized multimerized stradomer compositions will vary, naturally, with the location and nature of the disease being treated. Administration will be via any common route, orally, parenterally, or topically. Exemplary routes include, but are not limited to oral, nasal, buccal, rectal, vaginal, ophthalmic, subcutaneous, intramuscular, intraperitoneal, intravenous, intra-arterial, intratumoral, spinal, intrathecal, intra-articular, intra-arterial, sub-arachnoid, sublingual, oral mucosal, bronchial, lymphatic, intra-uterine, subcutaneous, intratumor, integrated on an implantable device such as a suture or in an implantable device such as an implantable polymer, intradural, intracortical, or dermal. Such compositions would normally be administered as pharmaceutically acceptable compositions as described herein. The term "parenteral administration" as used herein includes any form of administration in which the compound is absorbed into the subject without involving absorption via the intestines. Exemplary parenteral administrations that are used in the present invention include, but are not limited to intramuscular, intravenous, intraperitoneal, intratumoral, intraocular, nasal or intra-articular administration. In a preferred embodiment the cysteine-optimized multimerizing stradomer is administered intravenously or subcutaneously.

In general, the cysteine-optimized multimerized stradomers are administered as pharmaceutically acceptable compositions. The term "pharmaceutically acceptable composition" includes compositions comprising one or more "pharmaceutically acceptable carriers" which refer any and all solvents, dispersion media, coatings, antibacterial and antifungal agents, isotonic and absorption delaying agents and the like. The use of such media and agents for pharmaceutically active substances is well known in the art. Exemplary pharmaceutically acceptable carriers include, but are not limited to, to sugars, such as lactose, glucose and sucrose; starches, such as corn starch and potato starch; cellulose, and its derivatives, such as sodium carboxymethyl cellulose, ethyl cellulose and cellulose acetate; tragacanth; malt; gelatin; talc; cocoa butter, waxes, animal and vegetable fats, paraffins, silicones, bentonites, silicic acid, zinc oxide; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and any other compatible substances employed in pharmaceutical formulations. Except insofar as any conventional media and/or agent is incompatible with the agents of the present disclosure, its use in therapeutic compositions is contemplated. Supplementary active ingredients also can be incorporated into the compositions.

The cysteine-optimized multimerized stradomer compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Pharmaceutical formulations of cysteine-optimized multimerized stradomer compositions and methods for administering cysteine-optimized multimerized stradomer compositions, including sterile injectable compositions and compositions for other routes of administration, have been described in U.S. Pat. No. 8,690,237 and U.S. Patent Application Publication Nos. US 2010-0239633 and US 2013-0156765, each of which is incorporated herein by reference.

In addition, the cysteine-optimized multimerized stradomer of the current invention or compositions thereof may optionally be administered before, during or after another pharmaceutical agent. In some embodiments, the cysteine-optimized multimerized stradomers of the current invention or compositions thereof are administered at least 1, 2, 3, 4, 5, 10, 15, 20, or more times. In such embodiments, the multiple administrations may be administered by the same actor and/or in the same geographic location. In some embodiments, the multiple administrations may be administered by different actors and/or in different geographical locations. In some embodiments, multiple administrations of the cysteine-optimized multimerized stradomer or compositions thereof are administered separately through distinct routes of administration and/or are administered at separate times (e.g., sequentially).

Therapeutic Applications of Cysteine-Optimized Stradomers

In some aspects, the present disclosure provides methods for treating a disease or condition in a subject in need thereof, the method comprising administering a cysteine-optimized multimerized stradomer to the subject. In some aspects, methods are provided herein for the use of cysteine-optimized multimerized stradomers in the treatment and/or prevention of an inflammatory, autoimmune, or infectious disease or disorder.

The terms "treating" and "treatment" as used herein refer to administering to a subject a therapeutically effective amount of a cysteine-optimized multimerized stradomer of the present invention so that the subject has an improvement in a disease or condition, or a symptom of the disease or condition. The improvement is any improvement or remediation of the disease or condition, or symptom of the disease or condition. In some embodiments, the improvement is an observable or measurable improvement, or may be an improvement in the general feeling of well-being of the subject. Thus, one of skill in the art realizes that a treatment may improve the disease condition, but may not be a complete cure for the disease. Specifically, improvements in subjects may include one or more of: decreased inflammation; decreased inflammatory laboratory markers such as C-reactive protein, TNF-α, IL-8, or C5a; increased anti-inflammatory biomarkers such as iC3b, IL-10, or IL-1RA; changes in cellular phenotype such as increase in regulatory T cells, changes in HLA-DR on monocytes, or changes in B cell maturation markers; decreased autoimmunity as evidenced by one or more of: improvements in autoimmune markers such as autoantibodies or in platelet count, white blood cell count, or red blood cell count, decreased rash or purpura, decreased weakness, numbness, or tingling, increased glucose levels in patients with hyperglycemia, decreased joint pain, inflammation, swelling, or degradation, decreased cramping and diarrhea frequency and volume, decreased angina, decreased tissue inflammation, or decreased seizure frequency; decreased cancer pain, increased survival or improvements in the quality of life; delayed progression or improvement of osteoporosis; or decreased symptoms of an infectious disease, decreased presence of an infectious agent (e.g., a decrease in viral load), and/or decreased inflammation caused by immunopathogenicity triggered by an infectious agent (e.g., viral encephalitis, viral hemorrhagic fever, or sepsis).

In some embodiments, the cysteine-optimized multimerized stradomers and compositions thereof are administered prophylactically, e.g., prior to the onset of a disease or disease symptoms. As used herein, "prophylaxis" can mean complete prevention of the symptoms of a disease, a delay in onset of the symptoms of a disease, or a lessening in the severity of subsequently developed disease symptoms.

The term "subject" is used interchangeably with the term "patient" herein, and is taken to mean any mammalian subject to which cysteine-optimized multimerized stradomers of the present invention are administered according to the methods described herein. In a specific embodiment, the methods of the present disclosure are employed to treat a human subject. The methods of the present disclosure may also be employed to treat non-human primates (e.g., monkeys, baboons, and chimpanzees), mice, rats, bovines, horses, cats, dogs, pigs, rabbits, goats, deer, sheep, ferrets, gerbils, guinea pigs, hamsters, bats, birds (e.g., chickens, turkeys, and ducks), fish and reptiles. In some embodiments, the subject is a human.

In some embodiments, the cysteine-optimized multimerized stradomers of the present invention exhibit IVIG-like and GL-2045-like effects, such as IVIG-like and GL-2045-like immune suppression and/or immune tolerance. As used herein, the terms "IVIG-like effect" or "IVIG-like tolerance" and the like refer to anti-inflammatory, immunosuppressive, and tolerogenic effects similar to those mediated by IVIG. The precise mechanisms responsible for IVIG-like immunosuppression are not entirely understood, but are thought to include, without limitation, FcγR binding and blockage of Fc receptors on dendritic cells, monocytes, macrophages, B cells, and/or NK cells; enhanced complement-mediated removal of antibodies; and/or activation of regulatory T cells via T regulatory epitopes present in the IVIG molecule. Through some or all of these mechanisms of action, IVIG can reduce inflammation and/or induce immune tolerance. The present inventors have surprisingly found that specific mutations of cysteine residues in multimerizing stradomers produce a cysteine-optimized multimerized stradomer that can protect against inflammation and FcγR-mediated and complement-mediated cytotoxicity. These optimized multimerized stradomers are less prone to chemical modification, non-specific protein binding, and aggregate formation, thereby preserving IVIG-like tolerance. Similarly, the terms "GL-2045-like effect" or "GL-2045-like tolerance" and the like refer to anti-inflammatory, immunosuppressive, and tolerogenic effects similar to those mediated by GL-2045.

Immune suppression and/or immune tolerance can be demonstrated through a variety of read-outs including: a) inhibition of complement deposition and complement dependent cytotoxicity (CDC); b) inhibition of direct cytotoxicity (DC); c) inhibition of FcγR-mediated antibody-dependent cell cytotoxicity (ADCC), FcγR-mediated antibody-dependent cellular phagocytosis (ADCP), and other such natural effector cell mechanisms; d) changes in prevailing cell profiles such as increases in percentages or numbers of regulatory T cells; e) down regulation of MHC-II (e.g., HLA-DR) on monocytes and/or alteration of B cell maturation markers; f) changes in cell surface protein expression; g) decreases in pro-inflammatory cytokines including IL-1, IL-6, IL-8, IL12/23, IL-17, TNF-α, and interferon (IFN)-γ and increases in anti-inflammatory cytokines including IL-4, IL-10, IL-13, IL-16, IL-35, IL-1RA, TGF-β, and IFNα; and h) increases in anti-inflammatory soluble receptors for proinflammatory cytokines such as TNF or IL-6.

In some aspects, the higher order multimers of the cysteine-optimized multimerized stradomers provided herein bind to immune cells and to unbound complement. For example, because the cysteine-optimized multimerized stradomer is multimeric, the cysteine-optimized multimerized stradomer can avidly bind C1q without being cell-bound, resulting in initial activation of complement, generation of anti-inflammatory iC3b, and ultimately inhibition of CDC as a means of achieving tolerance. This is unlike a monoclonal antibody that must be bound to a cell in close proximity to other monoclonal antibodies in order to bind C1q effectively, resulting in CDC. Thus, the higher order multimers of cysteine-optimized multimerized stradomers can preferentially bind to complement components away from cells, preventing CDC, and relative to the non-aggregated major component of IVIG or relative to a mAb, each of which will first bind its target antigen through its Fab with avidity and only then bind to C1q (inducing CDC) and immune cells such as NK cells (ADCC) and macrophages (ADCP) through its Fc domain. As such, in some aspects, the IVIG-like immune suppression of the higher order multimers occurs by increased binding of hexameric C1q. In another aspect, the IVIG-like immune suppression of the higher order multimers occurs by presentation of polyvalent Fc to Fc receptors.

In some aspects, the cysteine-optimized multimerized stradomers provided herein exhibit superior immune suppression on a mg/Kg potency basis compared with IVIG or GL-2045. Thus, in some aspects, the present disclosure provides methods for eliciting IVIG-like immune suppression in a subject by administering to the subject a cysteine-optimized multimerized stradomer. Such IVIG-like immune suppression may involve the effector functions of inhibition of CDC, ADCC, ADCP, Fc-dependent apoptosis, and/or additional mechanisms.

In some embodiments, the suppression of inflammation is measured by a reduction in inflammatory cytokines such as, for example, IFNγ, TNF-α, IL-12, IL-6, and others known in the art; or increase in anti-inflammatory cytokines such as, for example, IL-1RA. In further embodiments, the suppression of inflammation in the subject is measured by changes in cell populations such as an increase in regulatory T cells and/or by changes in immune cell surface markers such as, for example, monocyte HLA-DR or B cell maturation markers, and/or changes in complement components detectable in serum.

In some embodiments, a therapeutically effective amount of the cysteine-optimized multimerized stradomers provided herein are administered to a subject in need thereof (e.g., a subject suffering from an inflammatory, autoimmune, and/or infectious disease described herein). The term "therapeutically effective amount" or "effective amount" as used herein refers to an amount that results in an improvement or remediation of the symptoms of the disease or condition. The therapeutically effective amount will vary according to the intended effect of the cysteine-optimized multimerized stradomer. For example, in some embodiments, a lower dose of a cysteine-optimized multimerized stradomer is a therapeutically effective amount for modulation of complement-dependent mechanisms, while a higher dose of a cysteine-optimized multimerized stradomer is a therapeutically effective amount for modulation of Fc receptor-mediated mechanisms of immune suppression. In some embodiments, the therapeutically effective amount of a cysteine-optimized multimerized stradomer is greater than, less than, or equal to a therapeutically effective amount of IVIG. In some embodiments, a therapeutic dose of IVIG, or a therapeutically effective amount of IVIG, may be about 200 mg/kg, about 500 mg/kg, about 1 g/kg, about 2 g/kg, or more. In some embodiments, a therapeutic dose of IVIG is about 200 mg/kg to about 5 g/kg, or about 600 mg/kg to about 2 g/kg.

In some embodiments, the cysteine-optimized multimerized stradomers provided herein are administered at the same dose as the parental non-cysteine-optimized multimerized stradomer such as GL-2045. In some embodiments, the cysteine-optimized multimerized stradomers provided herein are administered at a lower dose compared with GL-2045 to obtain a similar level of immune tolerance. In further embodiments, the dose level is less than about 50 mg/kg, less than about 10 mg/kg, less than about 5 mg/kg, less than about 1 mg/kg, less than about 0.5 mg/kg, less than about 0.1 mg/kg, less than about 0.05 mg/kg, or less than about 0.01 mg/kg. In some embodiments, the dose level is about 0.5 mg/kg to about 10 mg/kg.

In some embodiments, the mg/kg in vivo dosing level is determined by calculating the estimated circulating blood volume of the subject or group of subjects to receive the cysteine-optimized multimerizing stradomer.

In some embodiments, the cysteine-optimized multimerized stradomers described herein may be administered at least once daily, weekly, biweekly or monthly or potentially less frequently. The cysteine-optimized multimerized stradomers described herein may be administered at a dosing level designed to induce immune suppression and tolerance as described herein. Because of the enhanced efficacy of the cysteine-optimized multimerized stradomers of the current invention, or the nearly similar efficacy of the cysteine-optimized multimerized stradomers of the current invention with fewer free cysteines, in some embodiments the cysteine-optimized multimerized stradomers may be administered at a lower dose or higher dose compared with the corresponding non-cysteine-optimized multimerized stradomers. For example, the cysteine-optimized multimerized stradomers may be administered at a dose level that is lower or higher than the optimal dose of the corresponding non-cysteine-optimized multimerized stradomer. In some embodiments, the cysteine-optimized multimerized stradomer dose level is generally from about 1% to about 500% of the effective corresponding non-cysteine-optimized multimerized stradomer, more preferably, about 50% to about 100% of the effective corresponding non-cysteine-optimized multimerized stradomer, most preferably 60-95% of the effective corresponding non-cysteine-optimized multimerized stradomer.

The number of times a cysteine-optimized multimerized stradomer or composition thereof is administered to an subject in need thereof will depend on the discretion of a medical professional, the nature of the disease, the severity of the disease, and the subject's response to the formulation. Further, the dosage of each administration and/or frequency of administrations may be adjusted as necessary based on the patient's condition and physiologically responses. The dose of a cysteine-optimized multimerized stradomer or composition administered to a subject may be dependent on a variety of factors, including the disorder being treated and the severity of the disorder; the age, body weight, general health, sex and diet of the patient; the time of administration, route of administration, and rate of excretion; the duration of the treatment; drugs used in combination or coincidental with the cysteine-optimized multimerized stradomers; the judgment of the prescribing physician or veterinarian; and like factors known in the medical and veterinary arts.

In particular, the cysteine-optimized multimerized stradomers of the present invention may be used to treat conditions including but not limited to disease or disorder is selected from hematologic/vascular autoimmune conditions such as idiopathic thrombocytopenic purpura, alloimmune thrombocytopenia, post-transfusion purpura, aplastic anemia, red cell aplasia, autoimmune neutropenia, white cell aplasia, rejection associated with organ transplantation, systemic necrotizing vasculitis, autoimmune hemolytic anemia, hemophagocytic syndrome, Toxic Shock syndrome, hemolytic disease of the newborn, hemolytic transfusion reaction, and Kawasaki disease; neurologic autoimmune conditions such as chronic inflammatory polyneuropathy, multifocal motor neuropathy, Hashimoto's encephalopathy, limbic encephalitis, acute disseminated encephalomyelitis, IgM Paraproteinemic neuropathy, opsoclonus myoclonus ataxia, multiple sclerosis, epilepsy, Pediatric Autoimmune Neuropsychiatric Disease Associated with *Streptococcus*, Potassium-channel Antibody-Associated encephalopathy, and myasthenia gravis; and rheumatologic/dermatologic autoimmune conditions such as polymyositis/dermatomyositis, bullous pemphigoid, cicatricial pemphigoid, pemphigus *foliaceus*, pemphigus vulgaris, Toxic Epidermal Necrolysis, epidermolysis bullosa, pyoderma gangrenosum, inclusion body myositis, systemic lupus erythematosus, autoimmune uveitis, antiphospholipid syndrome, diabetic amyotrophy, Grave's ophthalmopathy, Scleromyxedema, Sjogren's syndrome, Rasmussen syndrome, and rheumatoid arthritis; congestive heart failure (CHF), vasculitis, rosacea, acne, eczema, myocarditis and other conditions of the myocardium, systemic lupus erythematosus, diabetes, spondylopathies, synovial fibroblast and bone marrow stroma abnormalities, bone loss, Paget's disease, osteoclastoma, disuse osteopenia, malnutrition, periodontal disease, Gaucher's disease, Langerhans' cell histiocytosis, spinal cord injury, acute septic arthritis, osteomalacia, Cushing's syndrome, monoostotic fibrous dysplasia, polyostotic fibrous dysplasia, periodontal reconstruction, bone fractures, sarcoidosis, bone pain management, humoral malignant hypercalcemia, ankylosing spondylitis and other spondyloarthropathies, transplantation rejection, and viral infections.

The cysteine-optimized multimerized stradomer of the present invention may be used to treat antibody-mediated or non-antibody-mediated autoimmune diseases. The term "autoimmune disease" as used herein refers to a varied group of more than 80 diseases and conditions. In all of these diseases and conditions, the underlying problem is that the body's immune system attacks the body itself. Autoimmune diseases affect all major body systems including connective tissue, nerves, muscles, the endocrine system, skin, blood, and the respiratory and gastrointestinal systems. Autoimmune diseases include, for example, systemic lupus erythematosus, rheumatoid arthritis, multiple sclerosis, myasthenia gravis, and type 1 diabetes.

In some embodiments, the present disclosure provides methods for reducing the incidence and/or severity of antibody mediated enhancement (AME). AME has been described in the art (Journal of Virology 77; 7539 (2003)) and develops when a subject develops antibodies against a virus during a virus infection. Virus-specific antibodies are then bound by C1q, enhancing internalization of the virus into cells, and thereby increasing viral load and worsening disease. In some embodiments, the cysteine-optimized multimerized stradomers provided herein, which act as a complement sink, disrupt, prevent, or reduce AME by binding up C1q such that antibody-bound virus is not taken up by cells via C1q.

The disease or condition treatable using the compositions and methods of the present invention may be a hematoimmunological process, including but not limited to idiopathic thrombocytopenic purpura, pregnancy or delivery of an Rh-positive baby irrespective of the ABO groups of the mother and baby, abortion/threatened abortion at any stage of gestation, ectopic pregnancy, antepartum fetal-maternal hemorrhage (suspected or proven) resulting from antepartum hemorrhage (e.g., placenta previa), amniocentesis, chorionic villus sampling, percutaneous umbilical blood sampling, other obstetrical manipulative procedure (e.g., version), or abdominal trauma, transfusion of Rh incompatible blood or blood products, alloimmune/autoimmune thrombocytopenia, acquired immune thrombocytopenia, autoimmune neutropenia, autoimmune hemolytic anemia, Parvovirus B19-associated red cell aplasia, acquired anti-factor VIII autoimmunity, acquired von Willebrand disease, multiple myeloma and monoclonal gammopathy of unknown significance, sepsis, aplastic anemia, pure red cell aplasia, Diamond-Blackfan anemia, hemolytic disease of the newborn, immune-mediated neutropenia, refractoriness to platelet transfusion, neonatal, post-transfusion purpura, hemolytic uremic syndrome, systemic vasculitis, thrombotic thrombocytopenic purpura, or Evan's syndrome.

The disease or condition may also be a neuroimmunological process, including but not limited to Guillain-Barre syndrome, chronic inflammatory demyelinating polyradiculoneuropathy, paraproteinemic IgM demyelinating polyneuropathy, Lambert-Eaton myasthenic syndrome, myasthenia gravis, multifocal motor neuropathy, lower motor neuron syndrome associated with anti-/GM1, demyelination, multiple sclerosis and optic neuritis, stiff man syndrome, paraneoplastic cerebellar degeneration with anti-Yo antibodies, paraneoplastic encephalomyelitis, sensory neuropathy with anti-Hu antibodies, epilepsy, encephalitis, myelitis, myelopathy especially associated with human T-cell lymphotropic virus-1, autoimmune diabetic neuropathy, Alzheimer's disease, Parkinson's disease, Huntington's disease, or acute idiopathic dysautonomic neuropathy.

The disease or condition may also be a Rheumatic disease process, including but not limited to Kawasaki's disease, rheumatoid arthritis, Felty's syndrome, ANCA-positive vasculitis, spontaneous polymyositis, dermatomyositis, antiphospholipid syndromes, recurrent spontaneous abortions, systemic lupus erythematosus, juvenile idiopathic arthritis, Raynaud's, CREST syndrome, or uveitis.

The disease or condition may also be a dermatoimmunological disease process, including but not limited to toxic epidermal necrolysis, gangrene, granuloma, autoimmune skin blistering diseases including pemphigus vulgaris, bullous pemphigoid, pemphigus *foliaceus*, vitiligo, Streptococal toxic shock syndrome, scleroderma, systemic sclerosis including diffuse and limited cutaneous systemic sclerosis, or atopic dermatitis (especially steroid dependent).

The disease or condition may also be a musculoskeletal immunological disease process, including but not limited to inclusion body myositis, necrotizing fasciitis, inflammatory myopathies, myositis, anti-Decorin (BJ antigen) myopathy, paraneoplastic necrotic myopathy, X-linked vacuolated myopathy, penacillamine-induced polymyositis, atherosclerosis, coronary artery disease, or cardiomyopathy.

The disease or condition may also be a gastrointestinal immunological disease process, including but not limited to pernicious anemia, autoimmune chronic active hepatitis, primary biliary cirrhosis, Celiac disease, dermatitis herpetiformis, cryptogenic cirrhosis, reactive arthritis, Crohn's disease, Whipple's disease, ulcerative colitis, or sclerosing cholangitis.

The disease or condition may also be graft versus host disease, antibody-mediated rejection of the graft, post-bone marrow transplant rejection, post-infectious disease inflammation, lymphoma, leukemia, neoplasia, asthma, Type 1 Diabetes mellitus with anti-beta cell antibodies, Sjogren's syndrome, mixed connective tissue disease, Addison's disease, Vogt-Koyanagi-Harada Syndrome, membranoproliferative glomerulonephritis, Goodpasture's syndrome, Graves' disease, Hashimoto's thyroiditis, Wegener's granulomatosis, micropolyarteritis, Churg-Strauss syndrome, polyarteritis *nodosa*, or multisystem organ failure.

In addition to having clinical utility for treating immunological disorders, cysteine-optimized multimerized stradomers have therapeutic use in infectious disease and inflammatory disease treatment. The cysteine-optimized multimerized stradomer may be used essentially following known protocols for IVIG and have the advantage not only of enhanced potency relative to IVIG in immune suppression, but also the added advantage of being less likely than corresponding non-cysteine-optimized multimerized stradomers to oxidize, aggregate, or form undesirable disulfide bonds. As described, certain cysteine-optimized multimerized stradomers additionally have enhanced multimerization and function relative to its corresponding non-cysteine-optimized multimerized stradomer.

Infectious diseases, include, but are not limited to, those caused by bacterial, mycological, parasitic, and viral agents. Examples of such infectious agents include, but are not limited to, *staphylococcus*, streptococcaceae, neisseriaaceae, cocci, enterobacteriaceae, pseudomonadaceae, vibrionaceae, *campylobacter*, pasteurellaceae, *bordetella, francisella, brucella*, legionellaceae, bacteroidaceae, *clostridium, corynebacterium, propionibacterium*, gram-positive bacilli, anthrax, *actinomyces, nocardia, mycobacterium, treponema, borrelia*, leptospira, *mycoplasma, ureaplasma, rickettsia*, chlamydiae, other gram-positive bacilli, other gram-negative bacilli, systemic mycoses, other opportunistic mycoses, protozoa, nematodes, trematodes, cestodes, adenoviruses, herpesviruses (including, for example, herpes simplex virus and Epstein Barr virus, and herpes zoster virus), poxviruses, papovaviruses, hepatitis viruses, papilloma viruses, orthomyxoviruses (including, for example, influenza A, influenza B, and influenza C), paramyxoviruses, coronaviruses, picornaviruses, reoviruses, togaviruses (e.g., alpha viruses such as Chikungunya virus), filoviruses (e.g., Ebolavirus, Margurgvirus, and Cuevavirus), flaviviruses (e.g., West Nile virus, Dengue virus, Yellow Fever virus, and Japanese Encephalitis virus), bunyaviridae, rhabdoviruses, respiratory syncitial virus, human immunodeficiency virus and retroviruses. Exemplary infectious diseases include but are not limited to candidiasis, candidemia, aspergillosis, streptococcal pneumonia, streptococcal skin and oropharyngeal conditions, gram negative sepsis, tuberculosis, mononucleosis, influenza, respiratory illness caused by Respiratory Syncytial Virus, malaria, Ebola virus disease (also known as Ebola hemorrhagic fever), encephalitis, schistosomiasis, and trypanosomiasis.

As used herein, the use of the word "a" or "an" when used in conjunction with the term "comprising" in the claims and/or the specification may mean "one," but it is also consistent with the meaning of "one or more," "at least one," and "one or more than one."

All references, patents, and patent applications cited herein are incorporated by reference in their entirety for all purposes.

EXAMPLES

The following examples are provided by way of illustration only and not by way of limitation. Those of skill in the

Example 1. Tryptic Digest Disulfide Bond Analysis of GL-2045

The disulfide bond structure of GL-2045 was analyzed by SDS-PAGE analysis followed by tryptic digests of bands 1-4, representing the homodimer (band 1), the dimer of the homodimer (band 2) the trimer of the homodimer (band 3) and the dimer of the dimer (the tetramer of the homodimer) (band 4). Digests were separated by HPLC with UV detection, and analyzed by in-line mass spectroscopy using a time of flight mass spectrometer (Agilent) equipped with electrospray ionization operating in a positive ion mode. The mass analysis from the peptide mapping separation was analyzed using Bioconfirm (Agilent). Sequence coverage of 100% was obtained for all four bands.

As described above, GL-2045 cysteines are present at positions 5, 11, 14, 46, 106, 152, 210, 236, 237, 240, and 243 of the stradomer unit monomer that comprise GL-2045. The GL-2045 disulfide bond analysis indicated that for band 1, the homodimer, cysteine residues at positions 5, 11 and 14 within the IgG1 hinge domain were all in the free sulfhydryl form. For all bands, cysteines 46 and 106, and separately cysteines 152 and 210 formed intra-chain disulfide bonds. In summary, cysteine residues at positions 46, 106, 152, and 210 of GL-2045 all formed intra-chain disulfide bonds in GL-2045 as occurs normally with immunoglobulin IgG1.

For band 1 (the homodimer) in GL-2045, four inter-chain disulfide linkages were present as shown in FIG. 1. Importantly, all of these disulfide bonds reside in the C-terminal IgG2 hinge domain of GL-2045; specifically, the bonds formed between cysteines that are present at positions 236, 237, 240, and 243 of the stradomer unit monomer.

For band 2 (dimer of the homodimer) and band 3 (trimer of the homodimer) in GL-2045, Fc multimerization occurred through a disulfide linkage between one of the cysteines in the C-terminal IgG2 domain of one GL-2045 stradomer unit and a cysteine within the N-terminal IgG1 domain of another GL-2045 stradomer unit (e.g., via one or more inter-unit disulfide bonds) as shown in FIG. 2. Specifically, a bond occurred between the cysteine at position 243 (IgG2 hinge domain monomer) and either the cysteine at position 14 or, alternatively, the cysteine at position 11 (each IgG1 hinge domain monomer) of the multimerized stradomer.

For band 4 (tetramer of the homodimer) in GL-2045, the multimerization was also a result of disulfide linkages between cysteines in the C-terminal IgG2 domain of one GL-2045 stradomer unit and cysteines in the N-terminal IgG1 domain of another GL-2045 stradomer unit (e.g., via one or more inter-unit disulfide bonds). The bond structure for band 4 was indistinguishable from the disulfide bond structure for bands 2 and 3, except for an additional structure involving cysteine number 5 in the IgG1 domain, which represented a small percentage of the band 4 composition compared to the structure shown in FIG. 2.

It was determined that the cysteine bonds involved in forming the monomer inter-chain disulfide bonds in the GL-2045 homodimer all reside within the IgG2 hinge monomer; they do not involve the 3 cysteines in the IgG1 hinge monomer nor the 4 cysteines in the IgG1 CH2 and CH3 monomer. This is in stark contrast to an ordinary IgG1 immunoglobulin, in which cysteine residues in the IgG1 hinge monomer, particularly those at positions 11 and 14 of the IgG1 hinge monomer, are responsible for homodimer formation through monomer inter-chain disulfide bonds (See, Liu et al., "Disulfide bond structures of IgG molecules Structural variations, chemical modifications and possible impacts to stability and biological function" mAbs 4:1, 17-23; January/February (2012)). In contrast, the GL-2045 homodimer demonstrates no inter-chain disulfide bonds in the IgG1 hinge monomer, IgG1 CH2, or IgG1 CH3 domain monomers. This indicates that the 3 cysteines in the IgG1 hinge monomer of the GL-2045 homodimer can be oxidized and are available for capping, e.g., by chemical modification or by a mutation to another amino acid, without altering the tertiary structure of GL-2045.

In summary, disulfide bond analysis suggested that all 11 of the cysteines in GL-2045 stradomer unit monomer are involved in disulfide bond formation and thus in the structure and function of the homodimer and/or multimers of GL-2045:

1. The 3 cysteine residues in the IgG1 hinge monomer each are uninvolved in homodimer formation and thus susceptible to unwanted and potentially detrimental oxidation. Cysteines 11 and 14, however, are expected to be critical for multimer formation based on the disulfide bond analysis, and cysteine 5 is involved in formation of a minor species. Without wishing to be bound by theory, it is possible that cysteine 5 may be more important as the degree of multimerization increases to band 5 and above;
2. The 4 cysteine residues in the IgG1 CH2 and CH3 domain monomers are involved in intra-chain disulfide bond formation as occurs in a normal IgG1 immunoglobulin. Thus, cysteines 46, 106, 152, and 210 each are occupied in disulfide bond formation, and each is expected to be important for multimer formation by stabilization of the GL-2045 homodimer; and
3. The 4 cysteines residues in the IgG2 hinge monomer are involved in the monomer inter-chain disulfide bond formation to create the homodimer and in the inter-unit disulfide bond formation to create the multimers. Thus cysteines 236, 237, 240, and 243 each are occupied in disulfide bond formation and expected to be critical for multimer formation.

The results of the study indicated that mutation of any of the 11 cysteines, all of which are involved in disulfide bond formation of GL-2045, could disrupt homodimer or multimer formation. In particular, cysteines 11 and 14 in the IgG1 hinge domain and cysteine 243 in the IgG2 hinge domain appeared to be critical for GL-2045 multimer formation; a mutation at any one of these positions would be expected to reduce or eliminate multimerization and function of the stradomer. Further, individual cysteine mutations at any one of positions 236, 237, and 240 of GL-2045 may be tolerated for maintenance of homodimer formation as disulfide bonds between the other 2 cysteines may be sufficient to maintain homodimer structure; however, based on GL-2045 structure, none of these mutations (at positions 236, 237, or 240) should affect multimerization of a cysteine-optimized GL-2045 derivative.

Example 2: Mutational Analysis of Single Cysteines in GL-2045

To further analyze the involvement of the individual cysteines in multimer formation, a mutational analysis was performed, wherein each individual cysteine was mutated to a serine residue. The effects of these individual mutations on multimer formation were analyzed by non-reducing SDS-PAGE.

GL-2045 variants were generated by PCR and cloned into expression vector pcDNA3.3. The variants were then expressed in HEK or CHO cells and purified by protein A affinity chromatography. Multimerization of each compound was then compared with GL-2045 by non-reducing SDS-PAGE analysis using Invitrogen gels that provided the highest resolution of higher order bands.

Single mutations were made of each of the individual cysteine residues in the IgG1 hinge domain monomer (Table 4), the IgG1 CH2 and CH3 domain monomers (Table 5), and the IgG2 hinge domain monomer (Table 6). For each of Tables 4-6, positions at which the cysteines were mutated to a serine are shown in bold and underlined text.

TABLE 4

Single Mutations in IgG1 hinge

| Compound | Mutation | Variant IgG1 Sequence | SEQ ID NO. |
|---|---|---|---|
| G895 | C5S | EPKSSDKTHTCPPCP | 11 |
| G896 | C11S | EPKSCDKTHTSPPCP | 12 |
| G897 | C14S | EPKSCDKTHTCPPSP | 13 |

TABLE 5

Single mutations in IgG1 CH2 and CH3

| Compound | Mutation | Variant IgG1 CH2 and CH3 Sequence | SEQ ID NO. |
|---|---|---|---|
| G1057 | C46S | APELLGGPSVFLFPPKPKDTLMISRTPEVTSVVV DVSHEDPEVKFNWYVDGVEVHNAKTKPREEQYNS TYRVVSVLTVLHQDWLNGKEYKCKVSNKALPAPI EKTISKAKGQPREPQVYTLPPSREEMTKNQVSLT CLVKGFYPSDIAVEWESNGQPENNYKTTPPVLDS DGSFFLYSKLTVDKSRWQQGNVFSCSVMHEALHN HYTQKSLSLSPGK | 14 |
| G1058 | C106S | APELLGGPSVFLFPPKPKDTLMISRTPEVTCVVV DVSHEDPEVKFNWYVDGVEVHNAKTKPREEQYNS TYRVVSVLTVLHQDWLNGKEYKSKVSNKALPAPI EKTISKAKGQPREPQVYTLPPSREEMTKNQVSLT CLVKGFYPSDIAVEWESNGQPENNYKTTPPVLDS DGSFFLYSKLTVDKSRWQQGNVFSCSVMHEALHN HYTQKSLSLSPGK | 15 |
| G1059 | C152S | APELLGGPSVFLFPPKPKDTLMISRTPEVTCVVV DVSHEDPEVKFNWYVDGVEVHNAKTKPREEQYNS TYRVVSVLTVLHQDWLNGKEYKCKVSNKALPAPI EKTISKAKGQPREPQVYTLPPSREEMTKNQVSLT SLVKGFYPSDIAVEWESNGQPENNYKTTPPVLDS DGSFFLYSKLTVDKSRWQQGNVFSCSVMHEALHN HYTQKSLSLSPGK | 16 |
| G1060 | C210S | APELLGGPSVFLFPPKPKDTLMISRTPEVTCVVV DVSHEDPEVKFNWYVDGVEVHNAKTKPREEQYNS TYRVVSVLTVLHQDWLNGKEYKCKVSNKALPAPI EKTISKAKGQPREPQVYTLPPSREEMTKNQVSLT CLVKGFYPSDIAVEWESNGQPENNYKTTPPVLDS DGSFFLYSKLTVDKSRWQQGNVFSSSVMHEALHN HYTQKSLSLSPGK | 17 |

TABLE 6

Single mutations in IgG2 hinge region

| Compound | Mutation | Variant IgG2 hinge Sequence | SEQ ID NO. |
|---|---|---|---|
| G856 | C240S | ERKCCVESPPCP | 18 |
| G857 | C237S | ERKCSVECPPCP | 19 |
| G858 | C236S | ERKSCVECPPCP | 20 |
| G859 | C243S | ERKCCVECPPSP | 21 |

Figure 4:
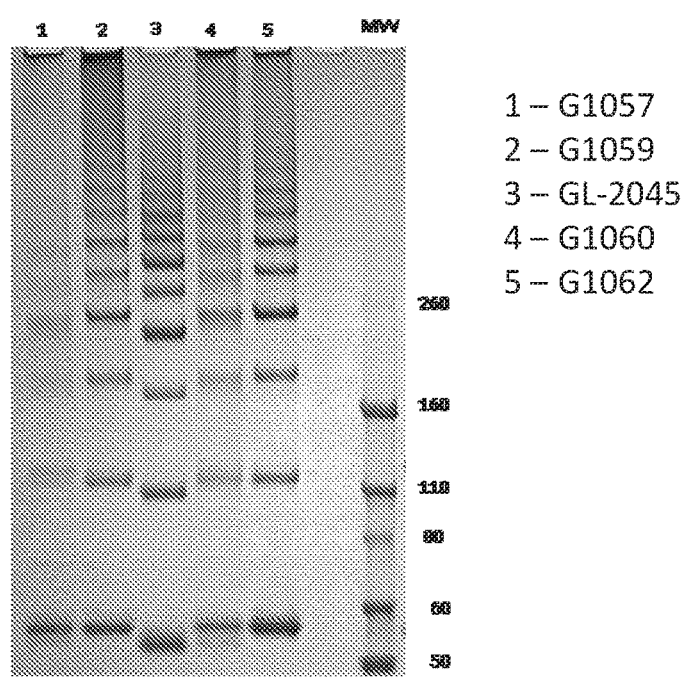
FIG. 4 shows the SDS-PAGE gel of stradomers having individual cysteine mutations in the IgG1 CH2 and CH3 domains (G1057, G1059, G1060, G1062) with GL-2045 as a comparison.
Figure 5:
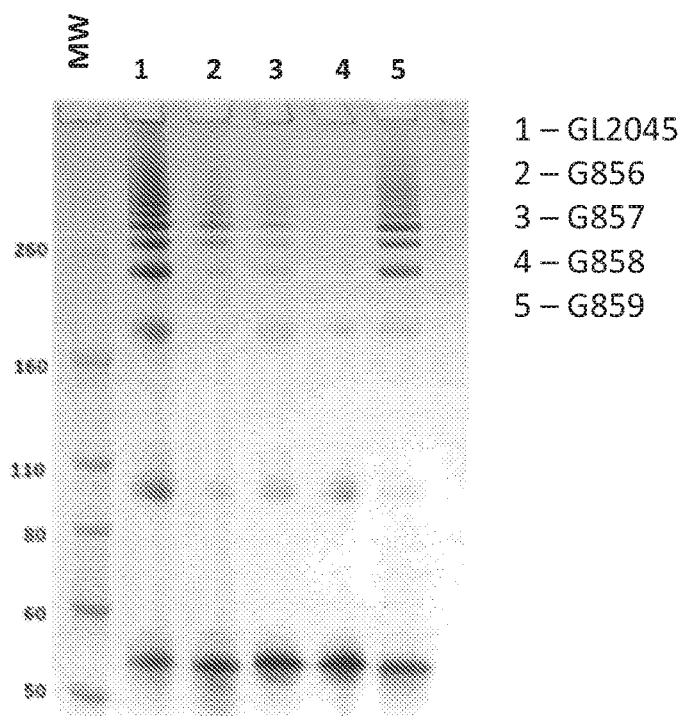
FIG. 5 shows the SDS-PAGE gel of individual cysteine mutations in the IgG2 hinge domain. The SDS-PAGE was run using 4-12% NuPageBT (Invitrogen) for 4 h at 150V in MOPS running buffer. From left to right, the lanes shown are: the molecular weight marker lane (MW); GL2045; G856; G857; G858; and G859.

The SDS-PAGE results for GL-2045 variants comprising single cysteine mutations in the IgG1 hinge domain monomer are shown in FIG. 3. SDS-PAGE results for GL-2045 variants comprising cysteine mutations in the IgG1 CH2 and CH3 domain monomers are shown in FIG. 4. SDS-PAGE results for GL-2045 variants comprising single cysteine mutations in the IgG2 hinge domain monomer are shown in FIG. 5. Unexpectedly, a cysteine mutation in any of the four cysteines in the IgG2 hinge domain monomer reduced or eliminated multimerization (FIG. 5). However, the cysteine to serine mutation at residue 243 (FIG. 5, G859) surprisingly, given its criticality for GL-2045, demonstrated only a modest decrease in multimerization. In contrast, a cysteine to serine mutation at any of the three cysteines in the IgG1 hinge domain monomer (G895, G896, or G897, FIG. 3) very surprisingly did not reduce or eliminate multimerization as anticipated, despite the fact that the cysteine residues at position 11 and position 14 were previously demonstrated to be critical to disulfide bonding of GL-2045. Moreover, the cysteine to serine mutation at residue 5, which was demonstrated not to be involved in multimerization of GL-2045, may further increase multimerization (FIG. 3, G895) as indicated by the lower intensity of lower molecular weight bands.

Disruption of the 46-106 intra-chain disulfide bond via mutation at position 46 or 106 of the stradomer unit monomer (in the IgG1 CH2 CH3 domain monomers; G1057, G1058) makes the GL-2045 protein non-functional, as no protein was obtained for the G1058 mutant and very weak multimerization was observed for G1057. Surprisingly, however, single mutants G1059 (position 152) and G1060 (position 210), and double mutant G1062 (positions 152 and 210 discussed below in Example 3) exhibited multimerization patterns comparable to the parental protein GL-2045 (FIG. 4) and inhibited CDC as discussed below in Example 4. Without wishing to be bound by theory, it is noted that G1059, G1060, and G1062 may initially form more non-specific aggregates compared to GL-2045 based on the very highest part of the gel shown in FIG. 4; these are readily removed with standard purification techniques routinely used to purify monoclonal antibodies.

Thus, the results of the study quite unexpectedly in light of the parent compound GL-2045 showed that the cysteine residues at positions 11 and 14 of the IgG1 hinge can be mutated from cysteine to serine without loss of multimerization. In addition, mutation of the cysteine at position 5 was tolerated and may be beneficial. Furthermore, a mutation in any of the four cysteines in the IgG2 hinge at positions 236, 237, or 240 unexpectedly reduced or eliminated multimerization. However, mutation of cysteine 243 was surprisingly relatively well tolerated, demonstrating only a modest decrease in multimerization. Further still, disruption at position 46 or 106 in the IgG1 CH2 CH3 domain rendered the protein non-functional, whereas mutations at positions 152 and/or 210 of the parental stradomer GL-2045 in the IgG1 CH2 CH3 domain were surprisingly tolerated.

Example 3. Dual and Triple Mutational Analysis of GL2045

In order to further assess the ability to cysteine-optimize multimerizing stradomers, dual mutations were made of each of pair of cysteine residues in the IgG1 hinge domain monomer (Table 7) and a triple mutation was made of all cysteine residues in the IgG1 hinge domain monomer (Table 8). In addition, a dual mutation was made in two of the cysteine residues in the IgG2 CH2 CH3 domain monomers (Table 9). For each of Tables 7-9, positions at which the cysteine was mutated to serine are in bold and underlined text.

TABLE 7

Dual Mutations in IgG1 hinge

| Compound | Mutation | IgG1 Hinge Sequence | SEQ ID NO. |
|---|---|---|---|
| G899 | C11S C14S | EPKSCDKTHTSPPSP | 22 |
| G948 | C5S C14S | EPKSSDKTHTCPPSP | 23 |
| G949 | C5S C11S | EPKSSDKTHTSPPCP | 24 |

TABLE 9

Triple Mutations in IgG1 hinge Compound

| Mutation | IgG1 Hinge Sequence | SEQ ID NO. |
|---|---|---|
| G930 C5S C11S C14S | EPKSSDKTHTSPPSP | 25 |

Figure 6:
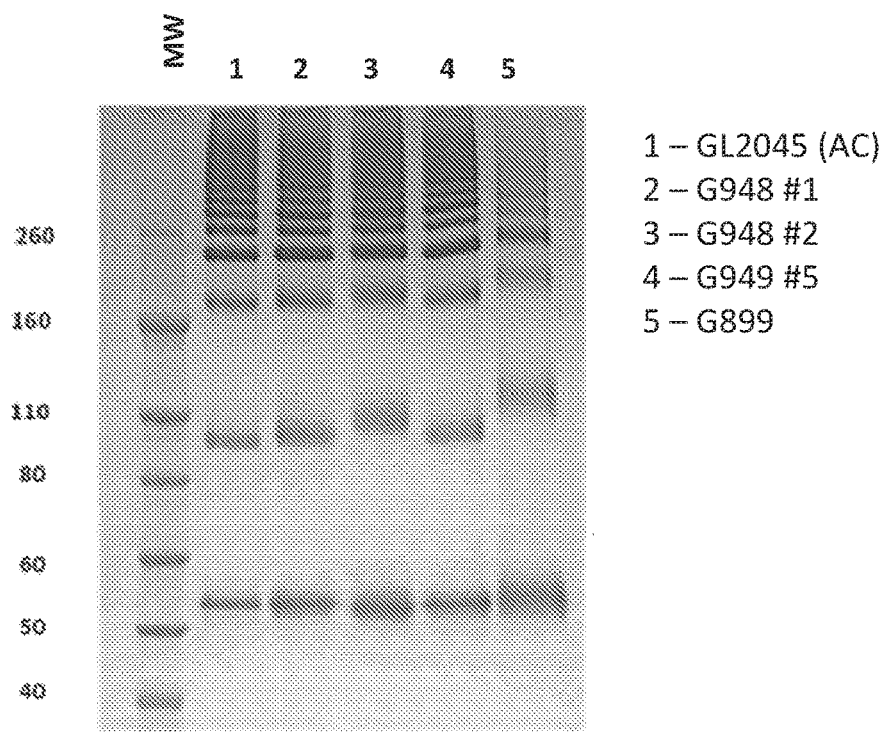
FIG. 6 shows the SDS-PAGE gel of dual mutations in IgG1 hinge domain. The SDS-PAGE was run using 4-12% NuPageBT (Invitrogen) for 4 h at 150V in MOPS running buffer.
Figure 7:
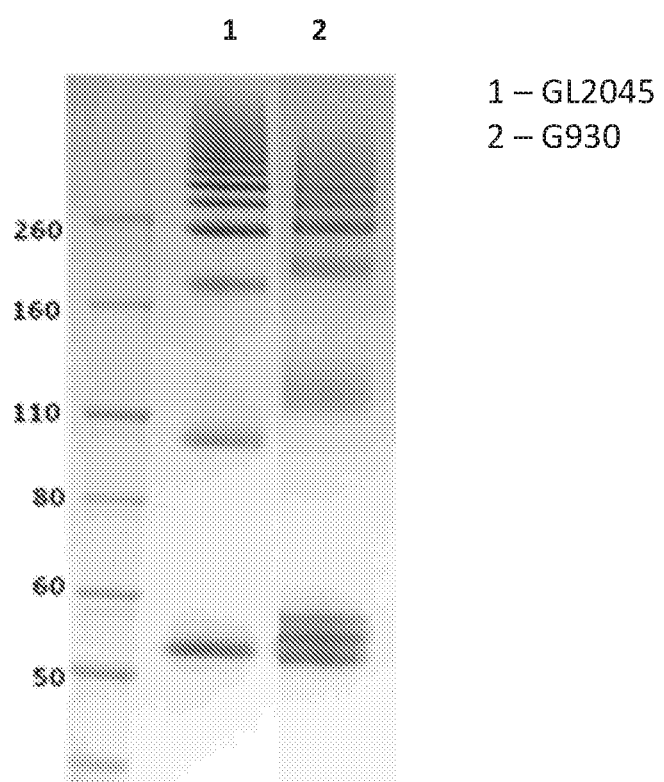
FIG. 7 shows the SDS-PAGE gel of triple mutations in IgG1 hinge domain.

The effects of dual cysteine mutations in the IgG1 hinge domain monomer on stradomer multimer formation are shown in FIG. 6. For G948, two individual clones were analyzed (G948 #1 and G948 #6). The triple cysteine mutations in the IgG1 hinge domain are shown in FIG. 7.

Together, the studies in Examples 2 and 3 quite unexpectedly showed the following results:

1. Despite the fact that disulfide bond analysis of GL-2045 indicated that all 11 cysteines residues are involved in disulfide bond formation, mutation of certain cysteines was well tolerated without disrupting homodimer or multimer formation.
2. Despite the fact that disulfide bonds of cysteines 11 and 14 were expected to be critical for multimer formation, serine mutations at each of these positions, individually (G896 and G897) or together (G899), were well tolerated and multimer formation was retained.
3. As expected given its lesser role in multimer formation, mutation of cysteine 5 was in fact well tolerated without large loss of multimers (G895); however, it was completely unexpected that multimer formation would be maintained in combination with a mutation to cysteine 11 (G949) or cysteine 14 (G948), and particularly unexpected that a triple mutation of cysteines 5, 11, and 14 (G930) would still result in multimer formation.
4. Despite the fact that disulfide bond analysis of GL-2045 indicated that cysteine 243 is critical for multimer formation, mutation to serine was well tolerated with excellent multimer formation (G859).
5. Despite the fact that disulfide bond analysis of GL-2045 indicated that individual cysteine mutations at positions 236, 237, and 240 may be required to maintain homodimer formation without affecting multimerization, mutation of any of these residues to serine led unexpectedly to excellent homodimer formation and unexpectedly to the loss of multimer formation (G856, G857, and G858).

TABLE 9

Dual Mutations in IgG1 CH2-CH3

| Compound | Mutation | IgG1 CH2-CH3 Sequence | SEQ ID NO. |
|---|---|---|---|
| G1062 | C152S C210S | APELLGGPSVFLFPPKPKDTL MISRTPEVTCVVVDVSHEDPE VKFNWYVDGVEVHNAKTKPRE EQYNSTYRVVSVLTVLHQDWL NGKEYKCKVSNKALPAPIEKT ISKAKGQPREPQVYTLPPSRE EMTKNQVSLTSLVKGFYPSDI AVEWESNGQPENNYKTTPPVL DSDGSFFLYSKLTVDKSRWQQ GNVFSSSVMHEALHNHYTQKS LSLSPGK | 26 |

As noted above in Example 2, double mutant G1062 (positions 152 and 210), exhibited comparable multimerization patterns relative to the parental protein GL-2045 (FIG. 4).

Example 4. Cysteine-Optimized Multimerizing Stradomers Retain Functionality

In order to demonstrate that the cysteine to serine mutations did not adversely affect function of the cysteine-optimized multimerizing GL-2045 stradomer variants, a complement-dependent cell killing (CDC) inhibition assay and an FcγRIIIA binding assay were performed.

CDC inhibition was assessed with an assay that determined the ability of the cysteine-optimized multimerizing GL-2045 stradomer variants to inhibit the normal CDC induced by a bound monoclonal antibody to a cell in the presence of serum. In general, the cysteine-optimized stradomers that multimerized well also inhibited CDC, and those cysteine-optimized stradomers that multimerized poorly did not inhibit CDC as well. This is expected given that C1q is hexameric.

Briefly, CD-20-expressing Will-2 cells were incubated with a CD-20 monoclonal antibody for 20 minutes in cell media, after which the cells were spun down and re-suspended in fresh media. Cells were incubated with media containing the stradomer test compound and distributed into 96 well plates. Serum was added to cell suspension and plates were incubated at 37° C. for 3 hours. Cell death was quantitated with the Promega Cytotox Glo Assay. Briefly, Cytotox Assay Reagent was added to each well and the plates were incubated in the dark for 15 minutes at room temperature. Luminescence was read on a Promega GloMax luminometer and cell death calculated.

Figure 8A:
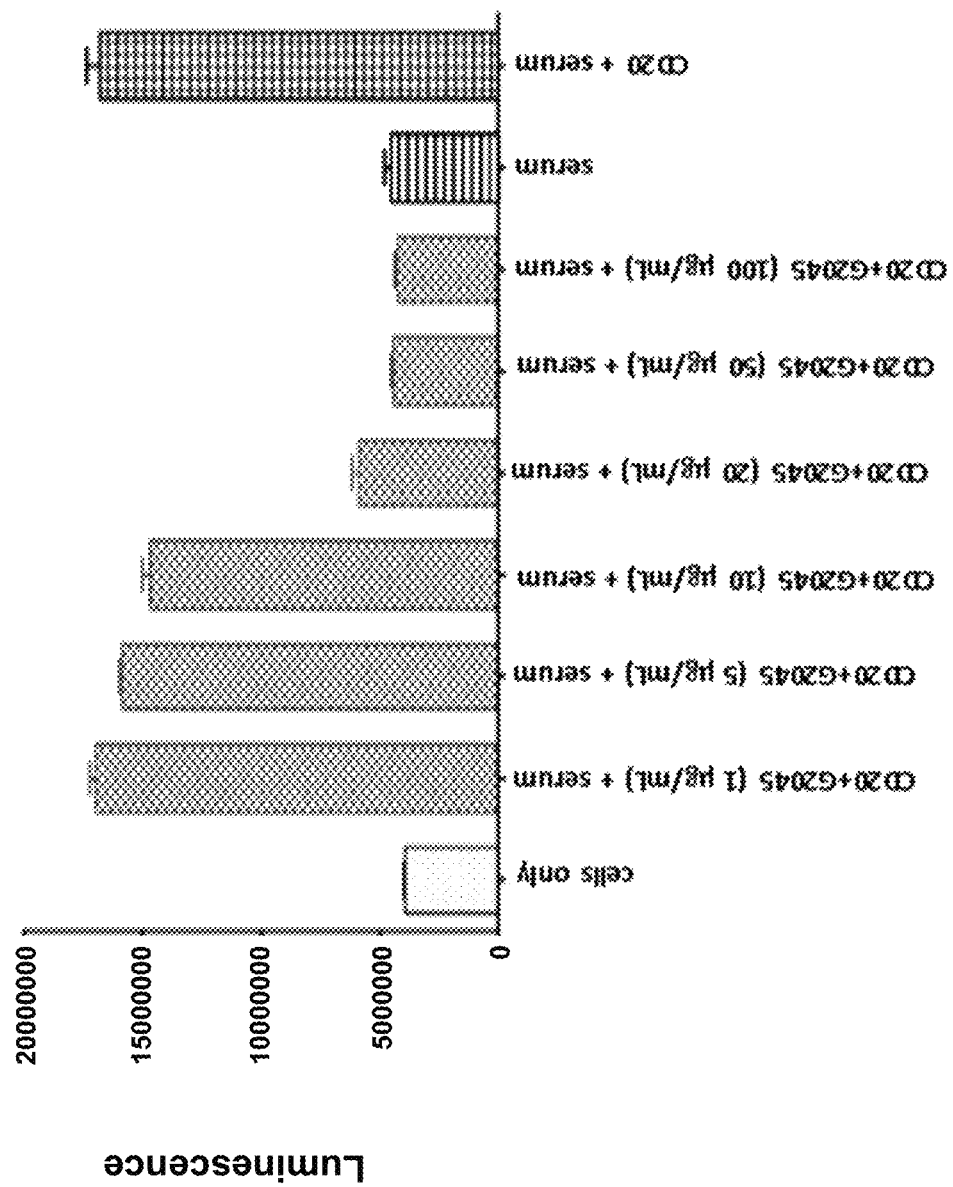
Figure 8B:
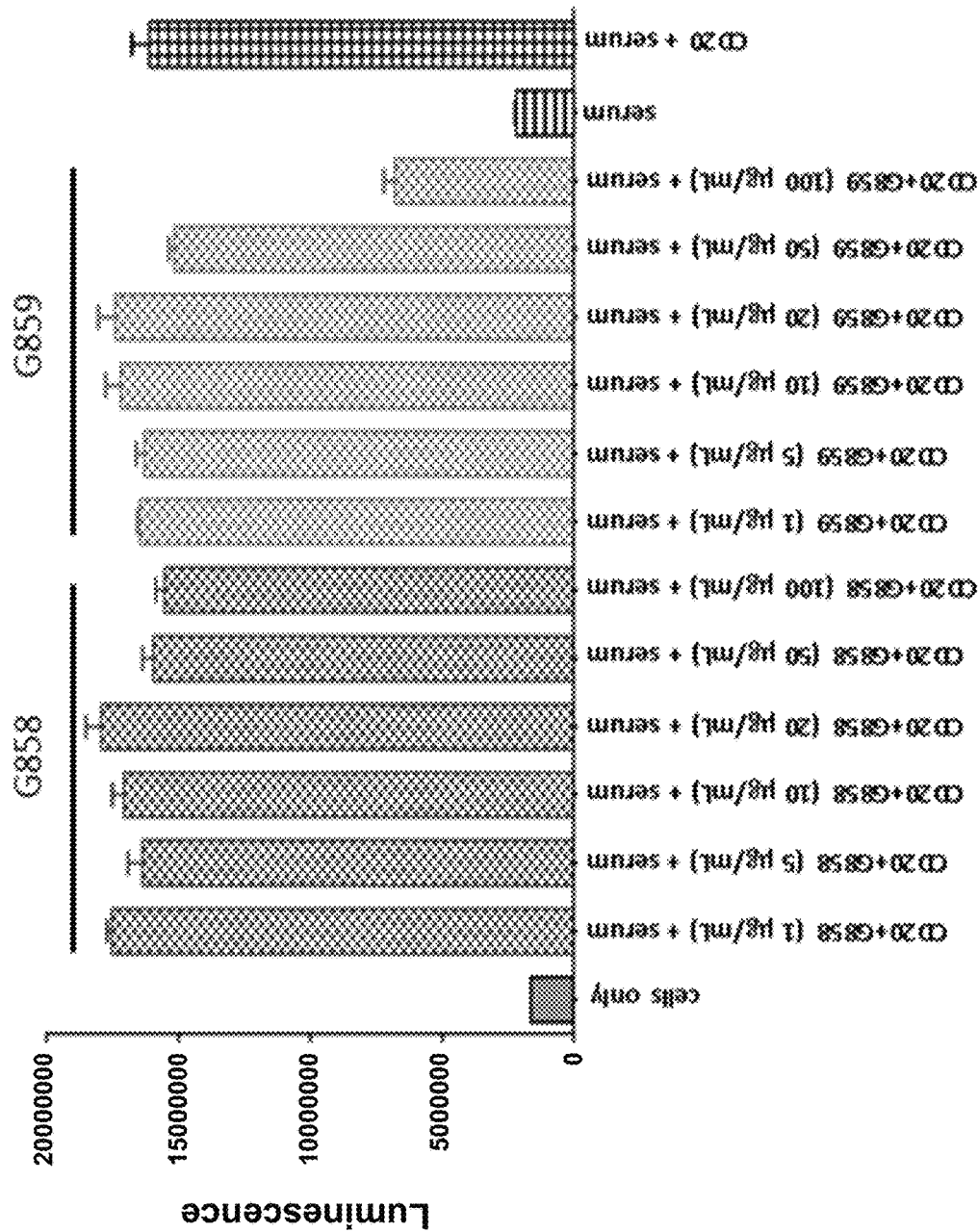

The effects of increasing concentrations of each test stradomer compound (e.g., 1 μg/mL, 5 μg/mL, 10 μg/mL, 20 μg/mL, 50 μg/mL, and 100 μg/mL) were determined for GL-2045 (FIG. 8A), G858 and 859 (FIG. 8B), and G948 and G949 (FIG. 8C). For each experiment, two negative control groups were used: one group comprising only cells (first bar on the left in each of FIGS. 8A-8C) and one group with cells and serum (second bar from right in each of FIGS. 8A-8C). A positive control group comprising cells, serum, and the CD20 antibody was also used in each experiment (last bar on the right in each of FIGS. 8A-8C). Estimated $EC_{50}$ values for CDC inhibition by G856, G857, G858, G859, G895, G896, G897, G899, G948, G949, G1057, G1059, G1060, and G1062 are provided below in Table 10. As noted above, no protein was obtained for G1057. Overall, the cysteine mutant stradomers that multimerized well also inhibited CDC (as shown by the lower estimated $EC_{50}$) and those cysteine mutant stradomers that multimerized poorly did not inhibit CDC as well.

TABLE 10

Estimated $EC_{50}$ values for CDC Inhibition of Cysteine Mutants

| Compound | Estimated $EC_{50}$ |
|---|---|
| G856 | 50 μg/mL |
| G857 | 200 μg/mL |
| G858 | >200 μg/mL |
| G859 | 100 μg/mL |
| G895 | 20 μg/mL |
| G896 | 75 μg/mL |
| G897 | 100 μg/mL |
| G899 | 100 μg/mL |
| G948 | 30 μg/mL |
| G949 | 40 μg/mL |
| G1057 | >200 μg/mL |
| G1058 | N/A* |
| G1059 | 20 μg/mL |
| G1060 | 50 μg/mL |
| G1062 | 20 μg/mL |
| GL-2045 | 15 μg/mL |

*No protein was obtained for G1058.

FcγRIIIA binding activity was assessed for each cysteine mutant by biolayer interferometry (ForteBio Octet®).

Briefly, binding was done in 1× kinetics binding buffer (ForteBio cat #18-1092). Stradomer concentrations used were 50 μg/mL, 25 μg/mL, 12.5 μg/mL, and 6.25 μg/mL. Binding analysis was performed using a ForteBio Octet Red system. The His-tagged receptor was loaded onto anti-penta-His sensors from ForteBio (HIS 1K cat #18-5121) at 5 μg/mL in 1× kinetics buffer for 300 sec and transferred to buffer for baseline measurement (60 sec). The on rate was measured for 300 sec after transfer of sensor tip to kinetics buffer containing ligand. The off rate was measured for 600 sec by transfer of sensor tip to kinetics buffer. His tagged receptors used were FcγRIIIA (R&D System cat #4325). Kd was calculated by ForteBio Data Analysis 6.4 software module using measured on and off rates and a 1:1 model fit. For Kd calculations an estimated average MW mass of 150 kD was assigned.

Figure 9A:
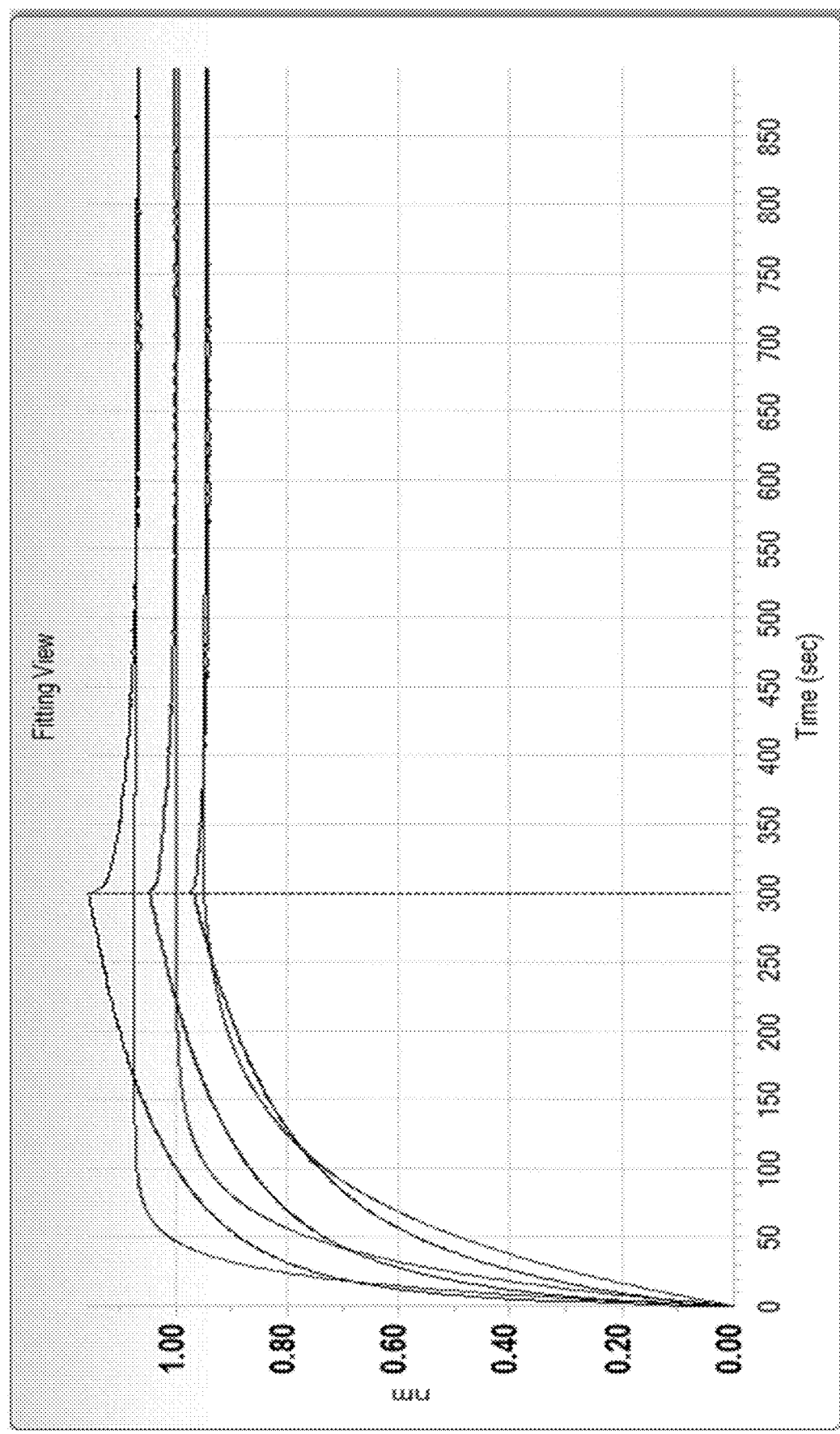
FIG. 9A-FIG. 9N shows the FcγRIIIa binding activity for each cysteine-optimized stradomer as assessed by biolayer interferometry (Octet®). FcγRIIIa binding activities for IgG2 hinge cysteine mutants (G856, G857, G858, G859, FIG. 9A-FIG. 9D), IgG1 hinge cysteine mutants (G895, G896, G897, G899, G948, G949, FIG. 9E-FIG. 9J), and IgG1 CH2-CH3 cysteine mutants (G1057, G1059, G1060, and G1062, FIG. 9K-FIG. 9N) are provided.
Figure 9B:
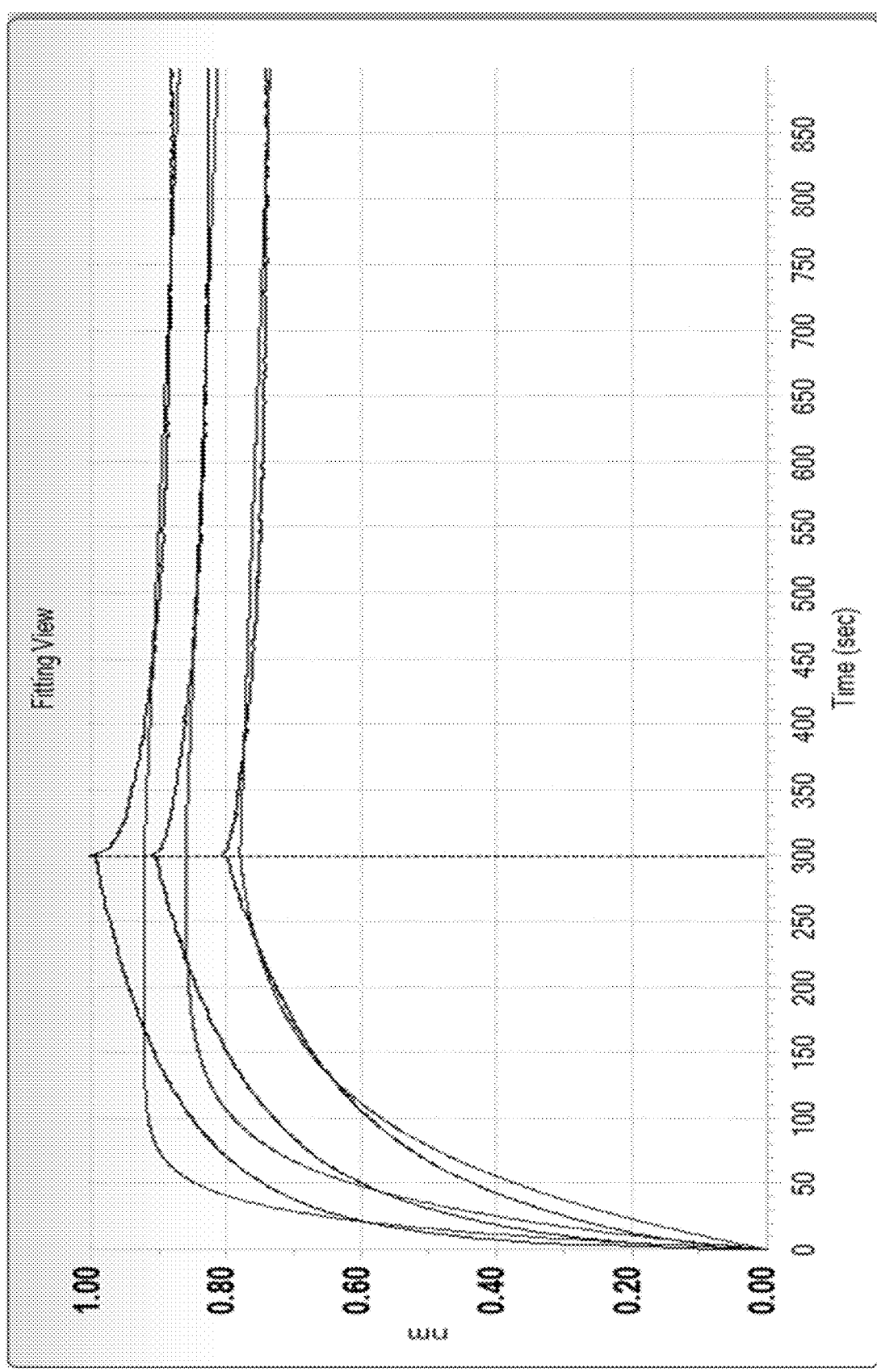
Figure 9C:
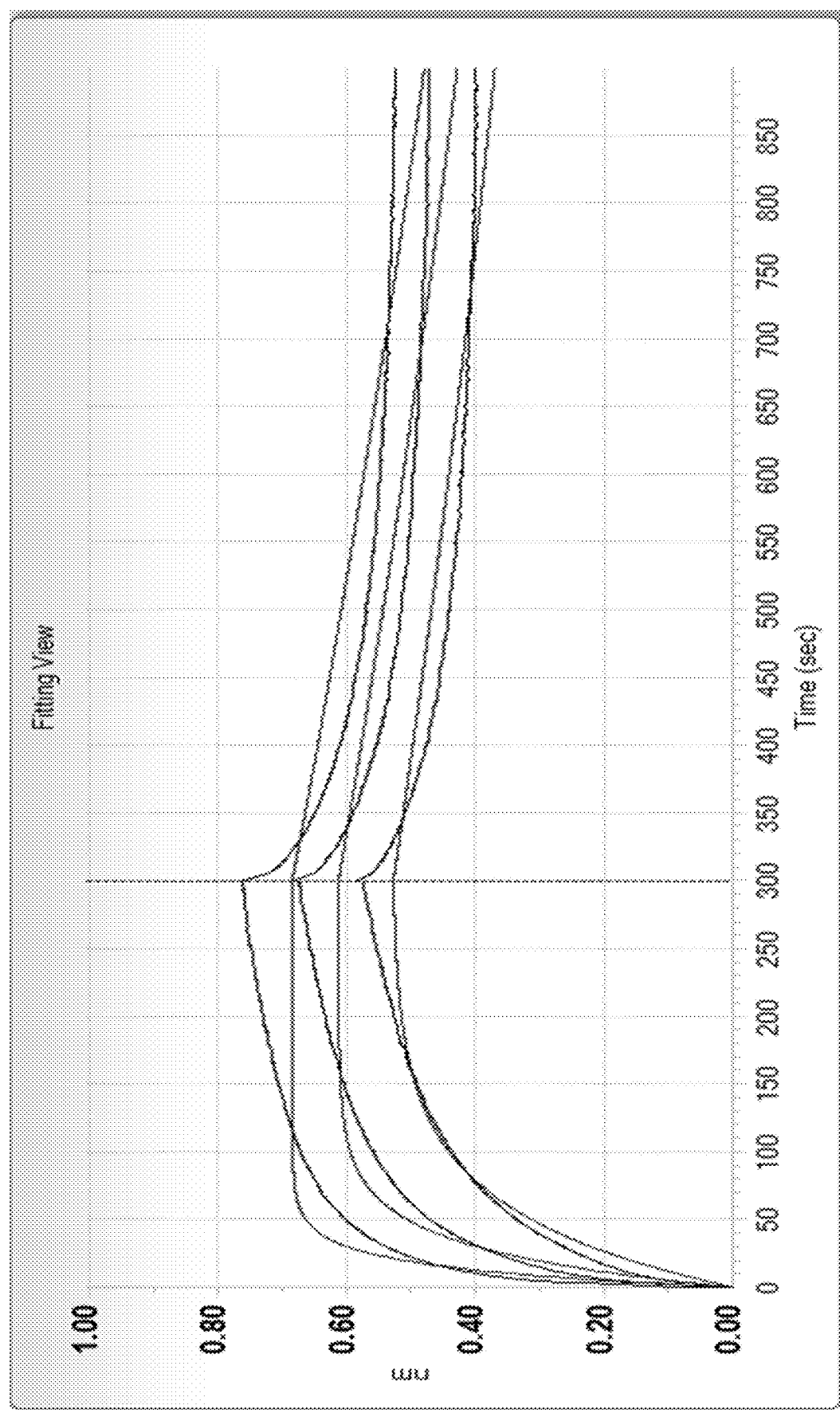
Figure 9D:
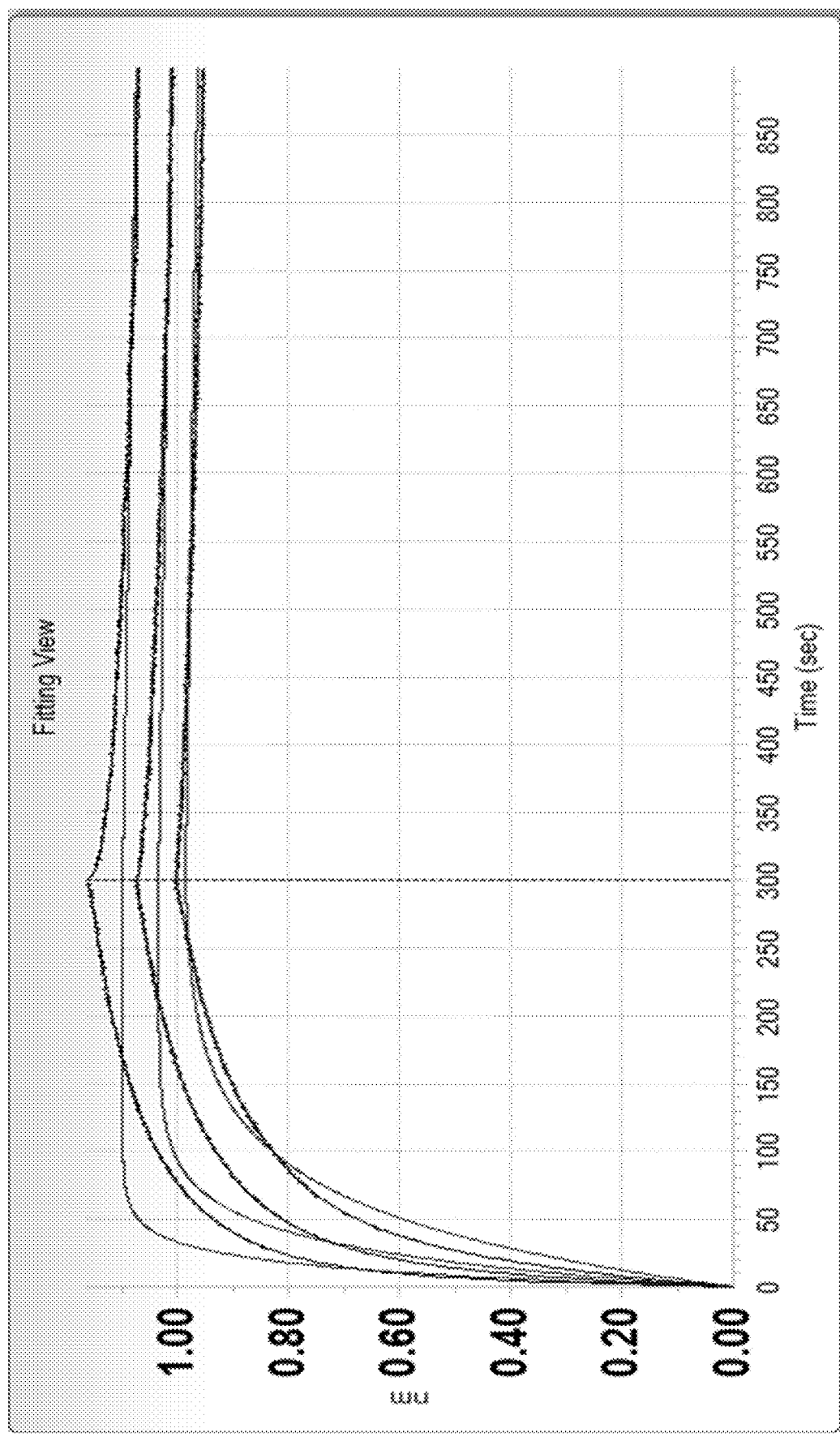
Figure 9E:
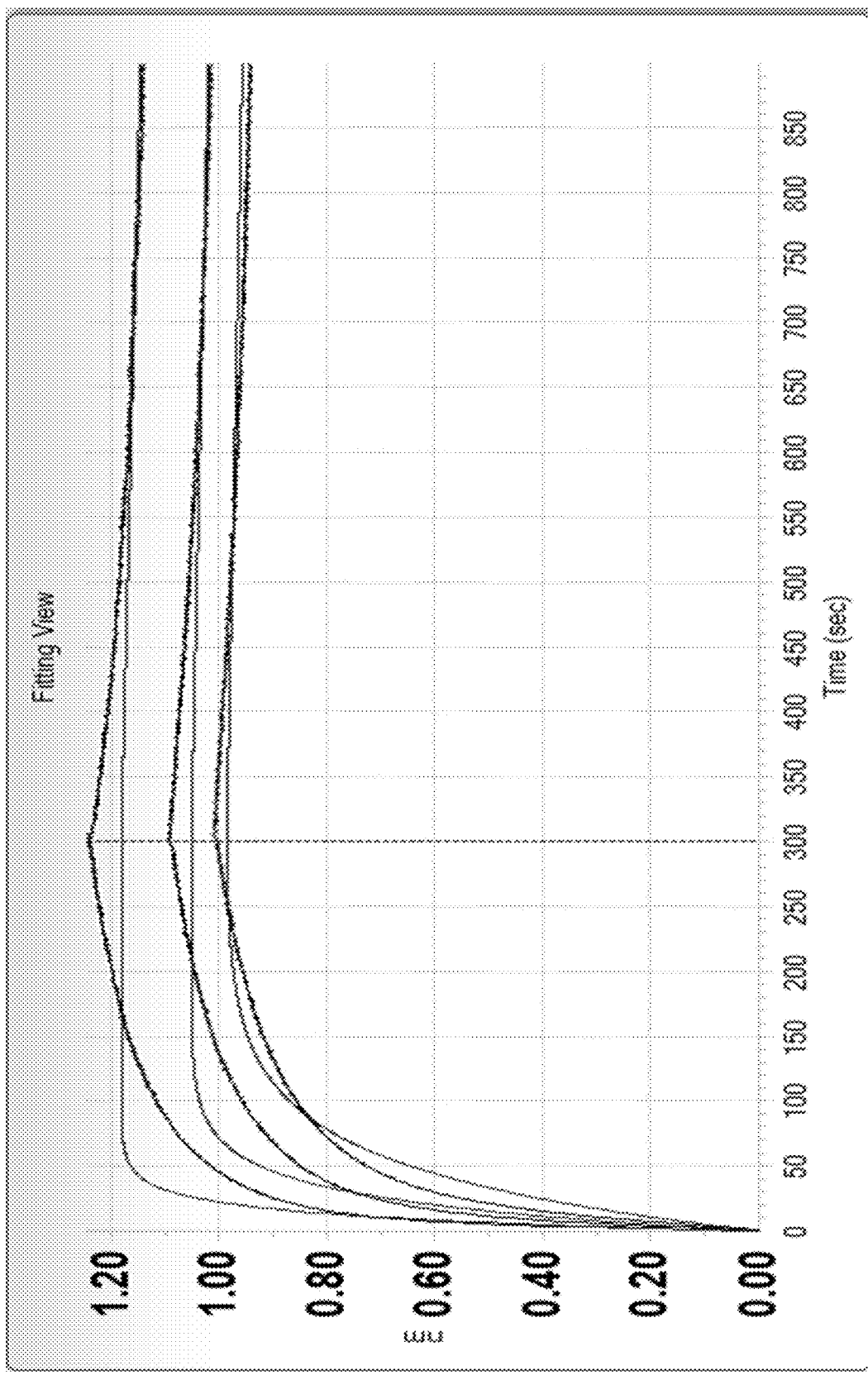
Figure 9F:
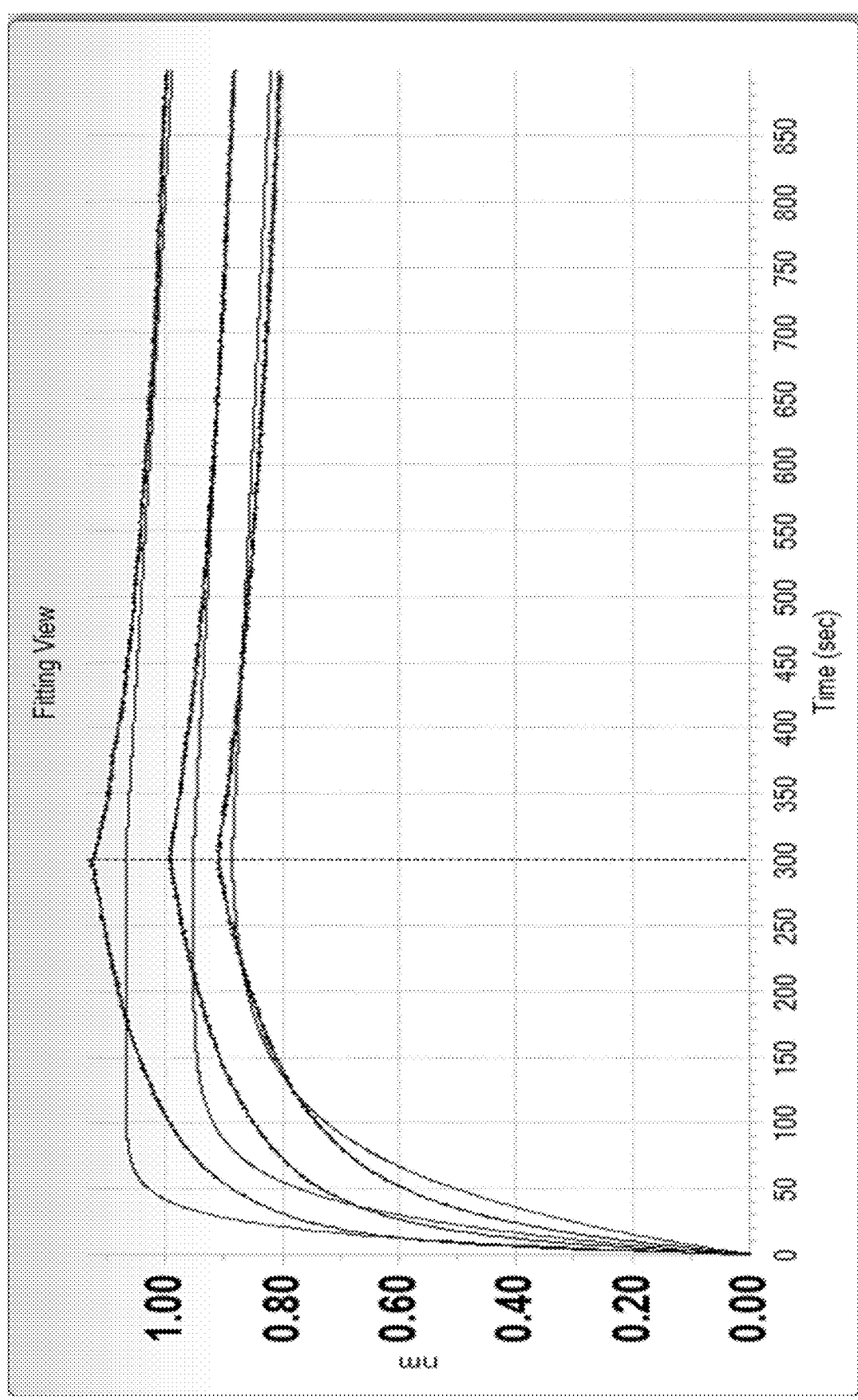
Figure 9G:
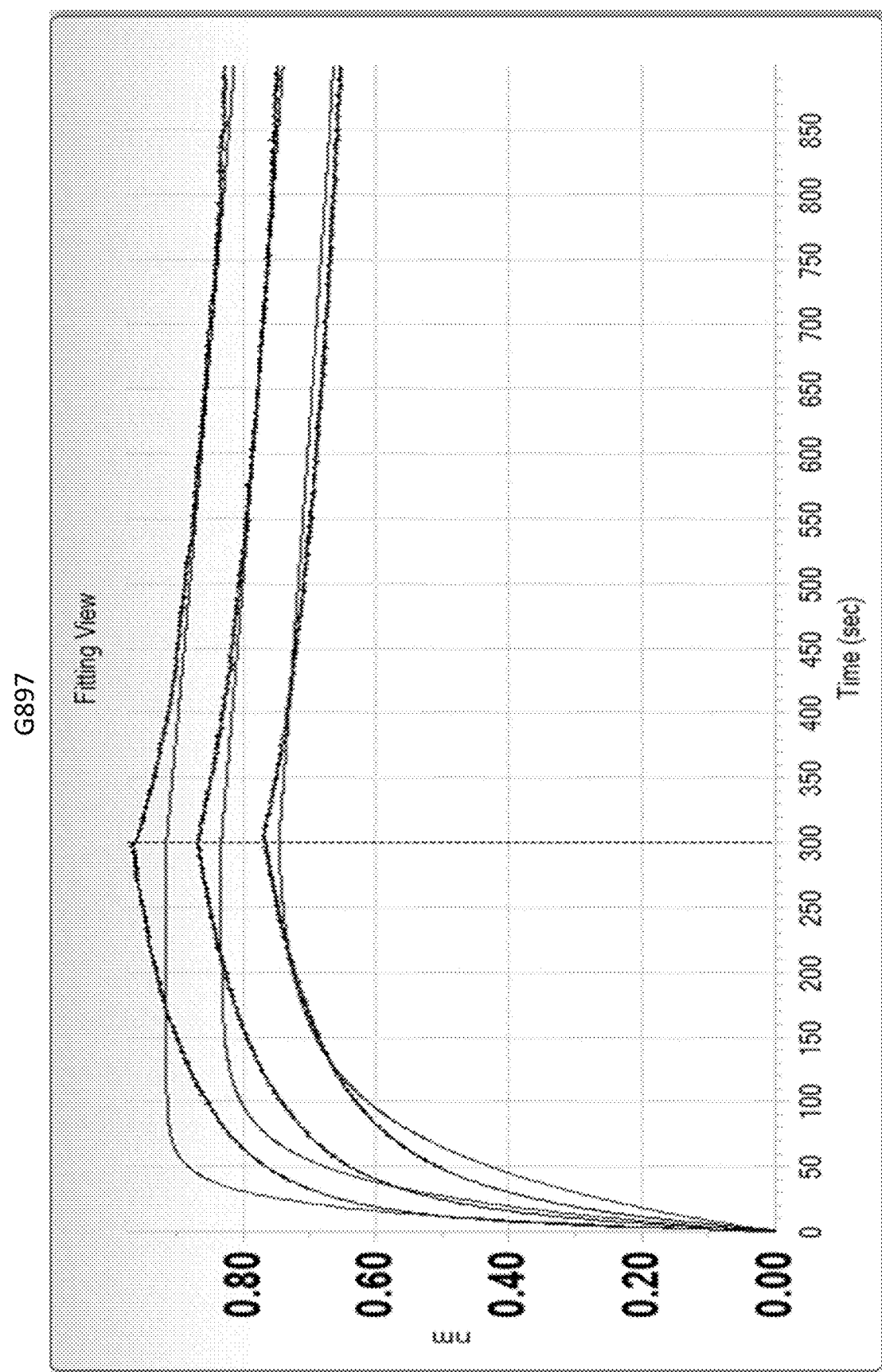
Figure 9H:
Figure 9I:
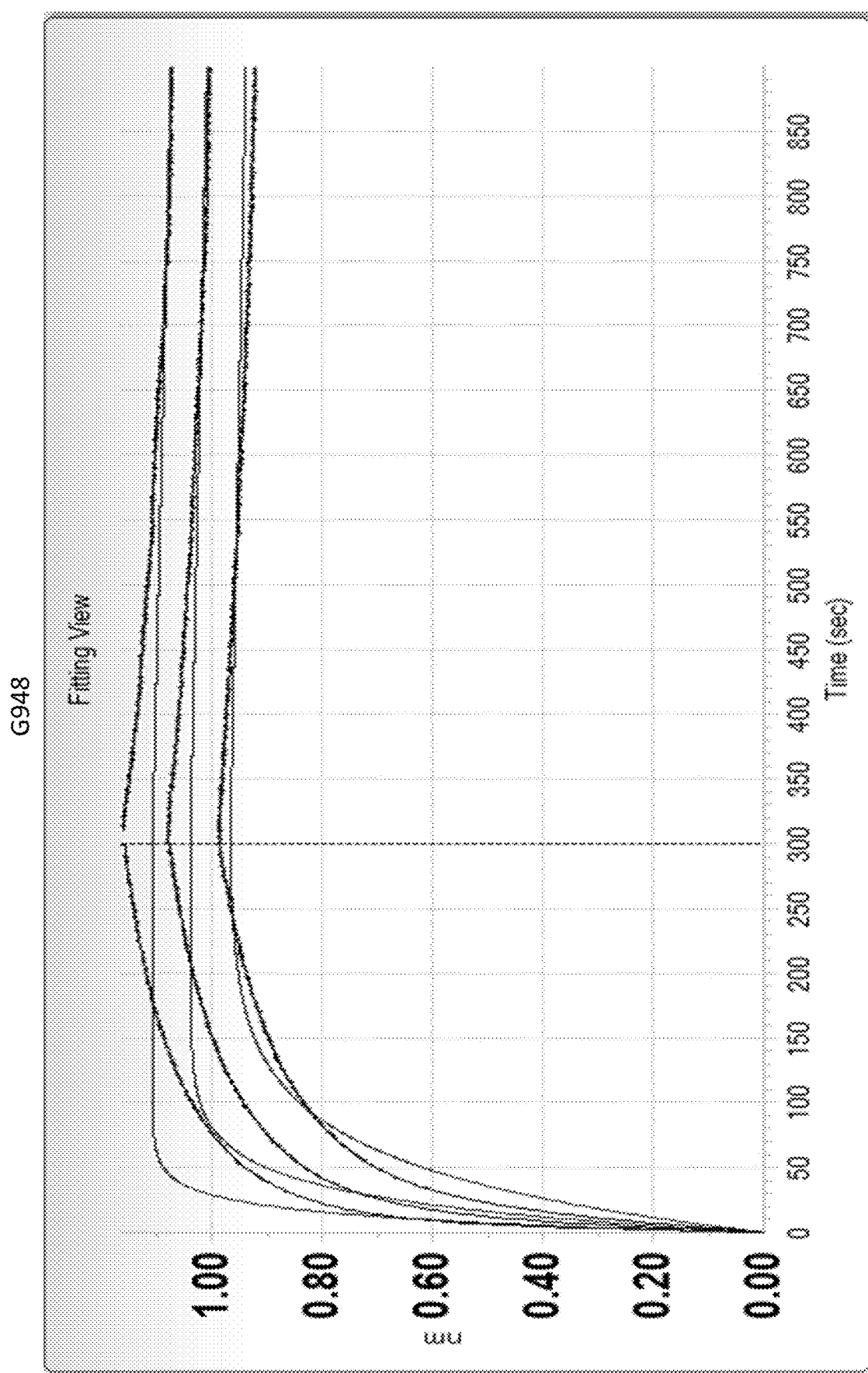
Figure 9J:
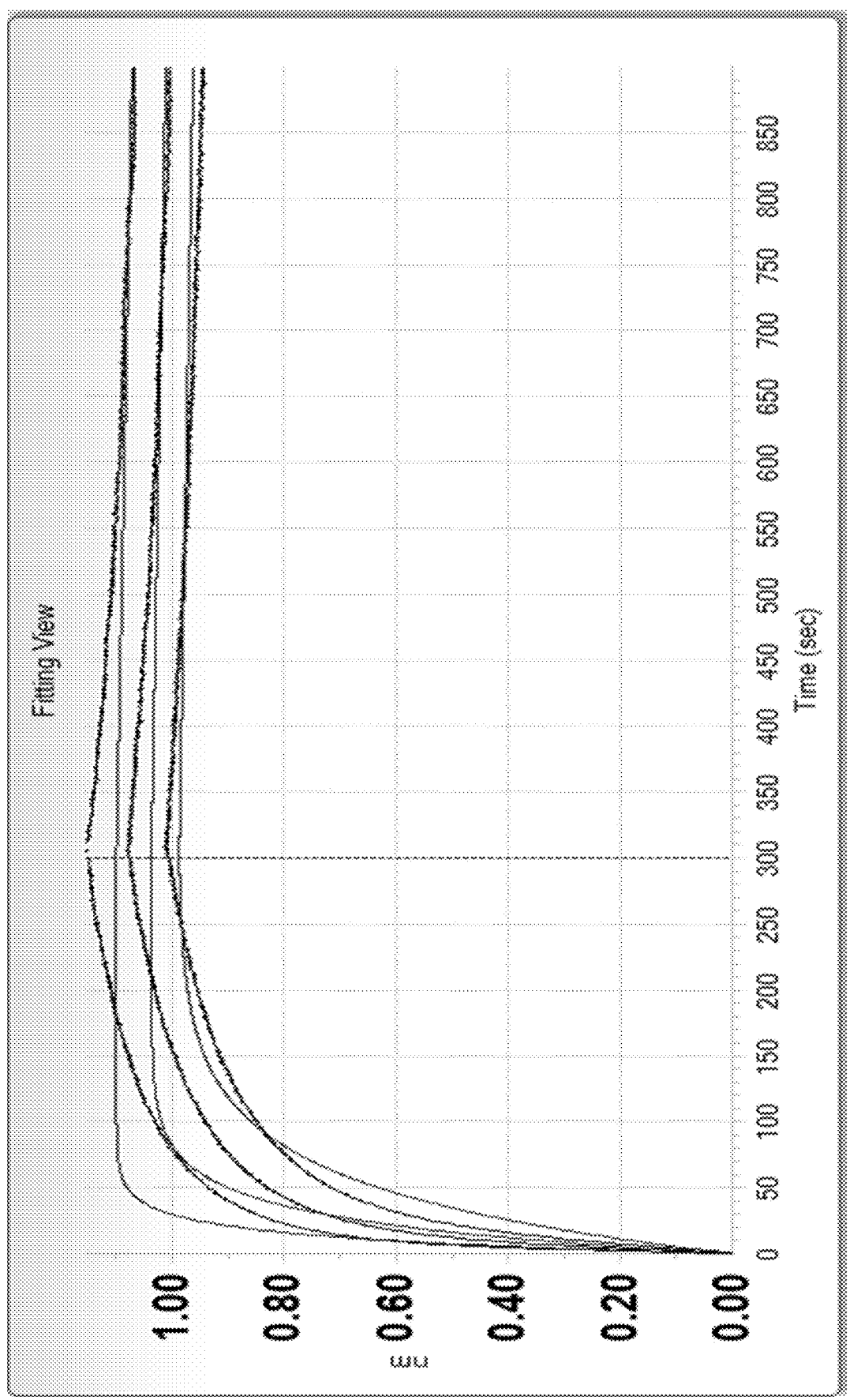
Figure 9K:
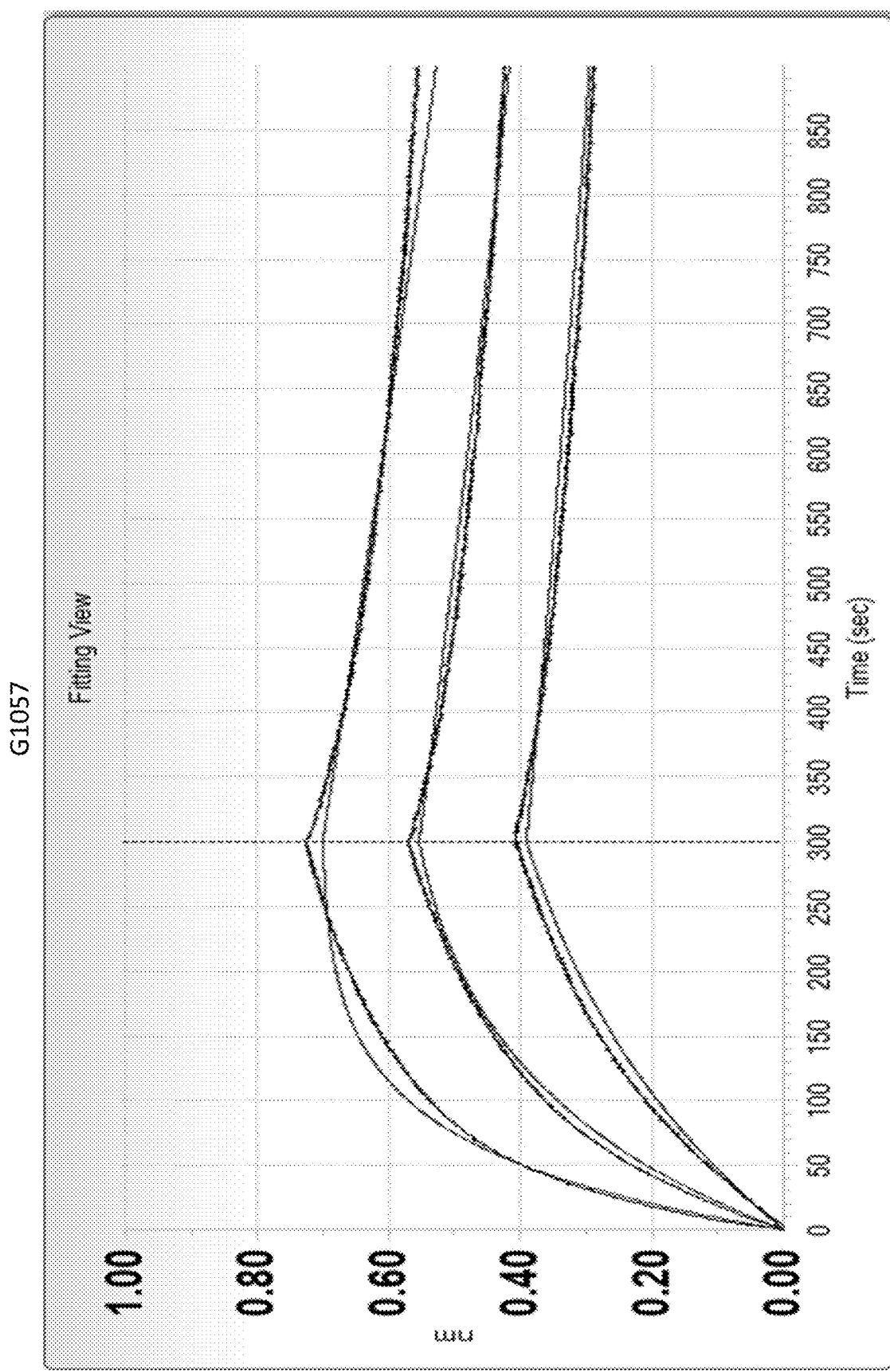
Figure 9L:
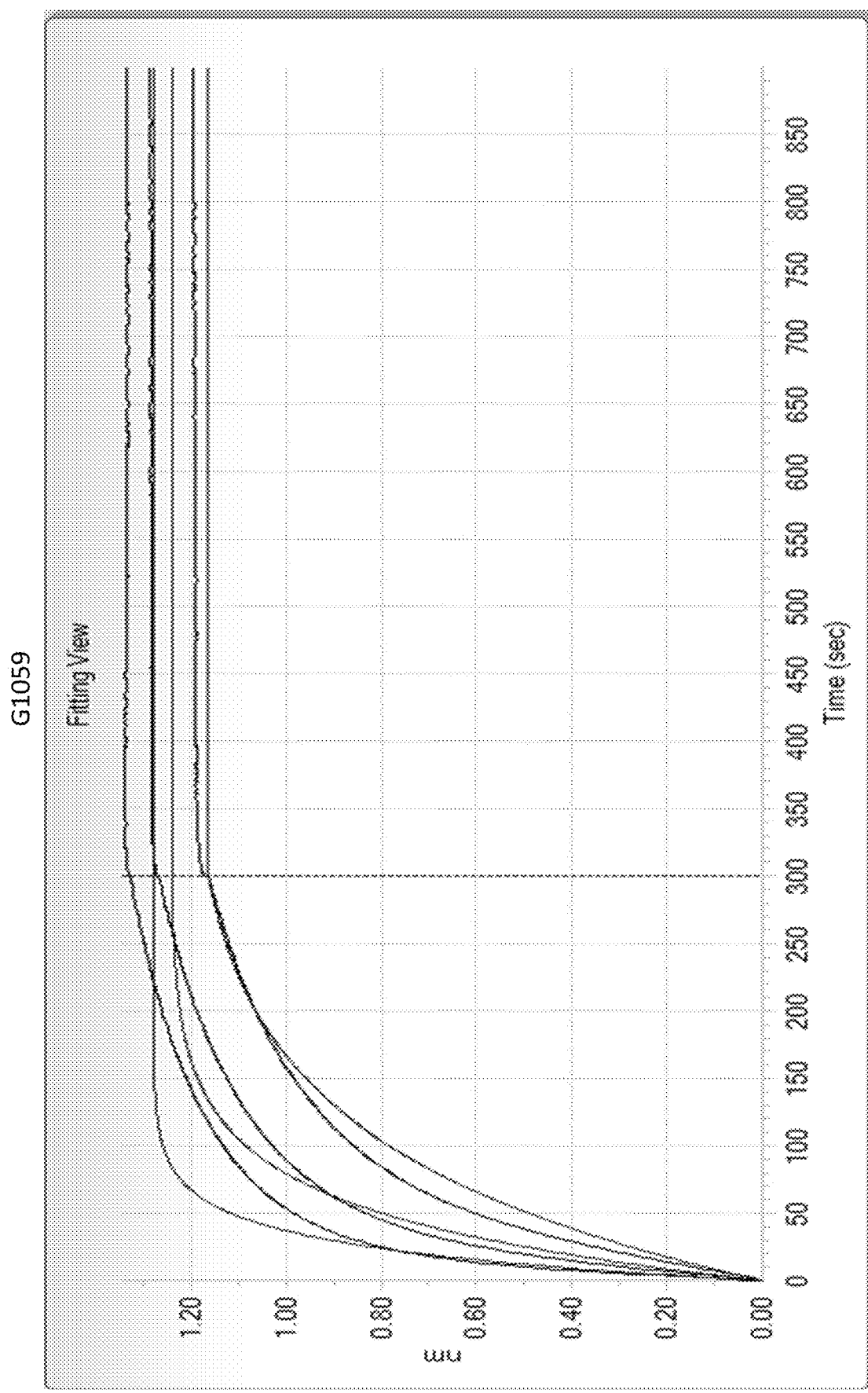
Figure 9M:
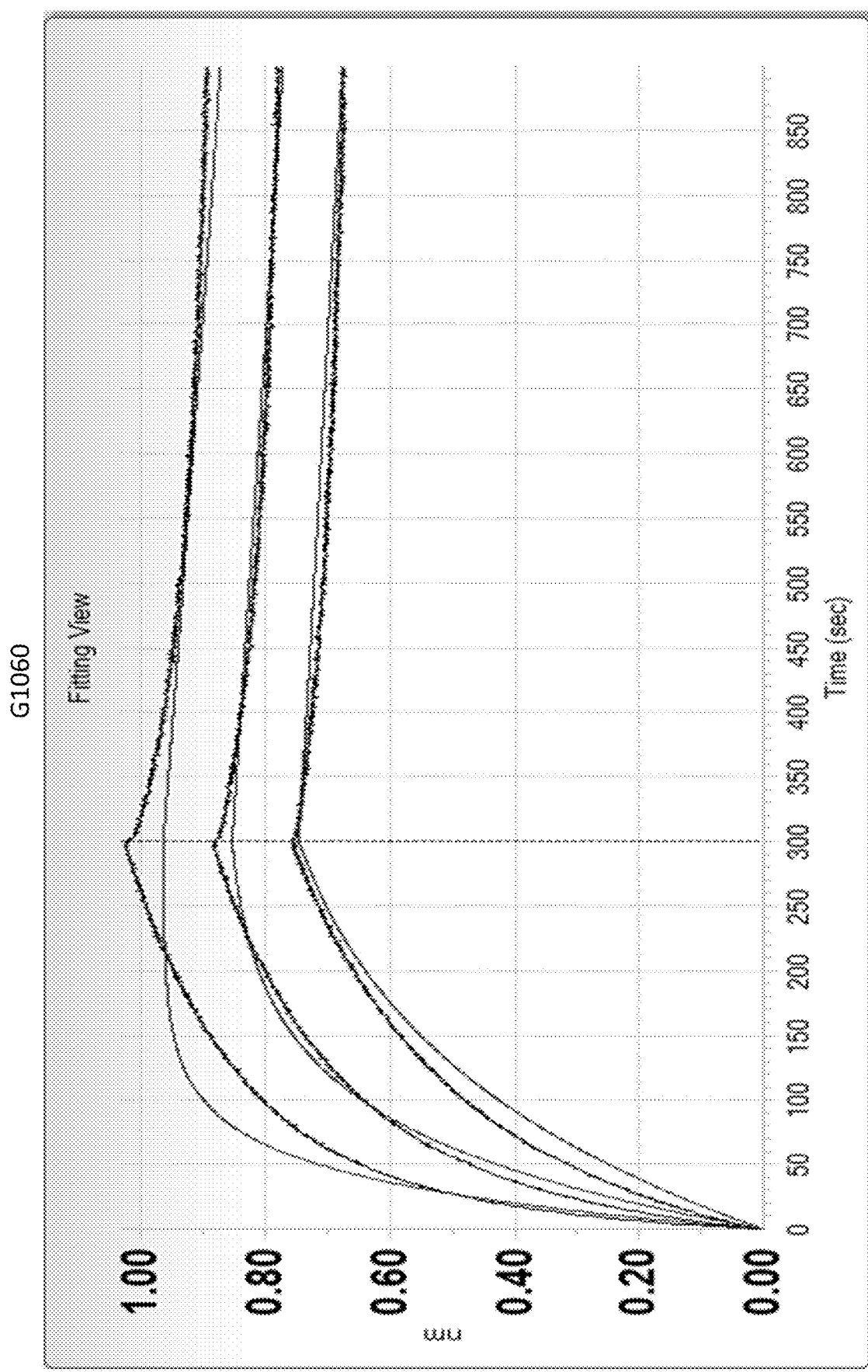
Figure 9N:
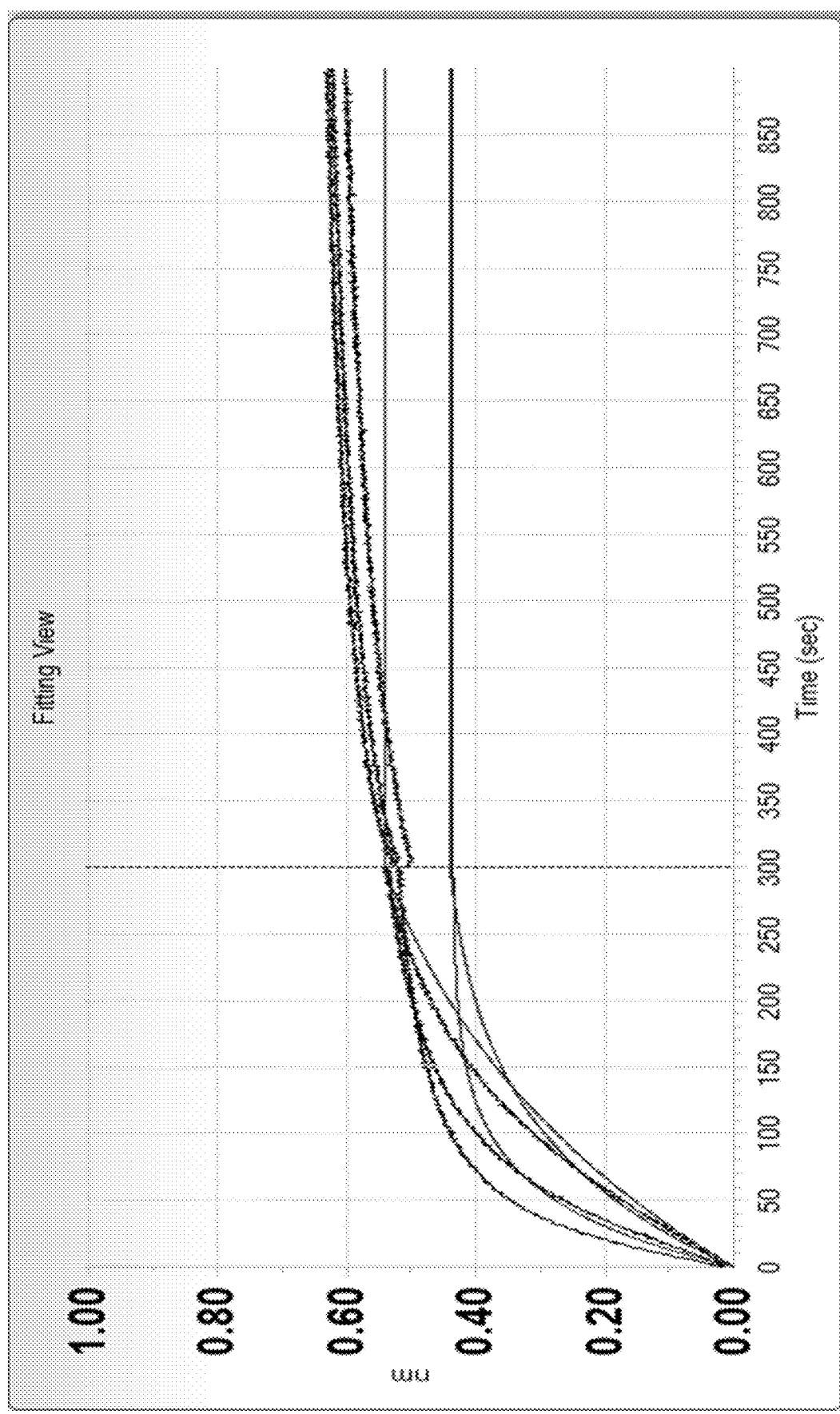

FcγRIIIa binding activity of each of G856, G857, G858, G859, G895, G896, G897, G899, G948, G949, G1057, G1059, G1060, and G1062 was assessed. The results of the study are provided below in Table 11 and in FIGS. 9A-9C. The results of the study showed that the functional activities of the cysteine-optimized multimerized stradomers were retained roughly in proportion to the multimerization with the exception of G1062, for which the model fit was poor.

TABLE 11

On/Off rates and calculated Kd, estimated error rate, $R_{max}$ values and $R^2/X^2$ values

| | Kd | $K_{on}$ | $K_{on}+/-$ | $K_{dis}$ | $K_{dis}+/-$ | $R_{max}$ | $X^2$ | $R^2$ |
|---|---|---|---|---|---|---|---|---|
| | | | IgG2 Hinge Mutants | | | | | |
| G856 | 4.75E−11 | 1.71E+05 | 2.00E+03 | 8.11E−06 | 5.50E−06 | 1.072 | 1.174 | 0.950 |
| G857 | 6.51E−10 | 1.49E+05 | 1.76E+03 | 9.67E−05 | 5.80E−06 | 0.924 | 0.879 | 0.954 |
| G858 | 2.87E−09 | 2.07E+05 | 3.97E+03 | 5.94E−04 | 9.54E−06 | 0.692 | 0.955 | 0.920 |
| G859 | 2.06E−11 | 1.88E+05 | 2.82E+03 | 3.89E−06 | 6.78E−06 | 1.155 | 1.748 | 0.912 |

TABLE 11-continued

On/Off rates and calculated Kd, estimated error rate, $R_{max}$ values and $R^2/X^2$ values

| | Kd | $K_{on}$ | $K_{on}+/-$ | $K_{dis}$ | $K_{dis}+/-$ | $R_{max}$ | $X^2$ | $R^2$ |
|---|---|---|---|---|---|---|---|---|
| IgG1 Hinge Mutants | | | | | | | | |
| G895 | 1.75E−11 | 2.01E+05 | 3.33E+03 | 3.51E−06 | 7.26E−06 | 1.247 | 2.303 | 0.908 |
| G896 | 5.23E−11 | 1.74E+05 | 2.38E+03 | 9.09E−06 | 6.34E−06 | 1.135 | 1.682 | 0.940 |
| G897 | 2.27E−10 | 1.76E+05 | 2.48E+03 | 3.99E−05 | 6.57E−06 | 0.836 | 1.348 | 0.935 |
| G899 | 3.33E−10 | 1.36E+05 | 1.81E+03 | 4.52E−05 | 6.60E−06 | 0.894 | 1.106 | 0.946 |
| G948 | 4.19E−11 | 1.99E+05 | 3.20E+03 | 8.33E−06 | 7.15E−06 | 1.182 | 2.149 | 0.901 |
| G949 | 3.81E−11 | 2.02E+05 | 3.36E+03 | 7.70E−06 | 7.35E−06 | 1.167 | 2.237 | 0.887 |
| IgG1 CH2/CH3 Mutants | | | | | | | | |
| G1057 | 5.31E−09 | 4.86E+04 | 3.62E+02 | 2.58E−04 | 4.03E−06 | 0.782 | 0.178 | 0.994 |
| G1059 | 8.48E−16 | 1.24E+05 | 1.74E+03 | 1.05E−10 | 6.97E−06 | 1.280 | 1.885 | 0.942 |
| G1060 | 2.09E−09 | 7.68E+04 | 7.89E+02 | 1.60E−04 | 5.47E−06 | 0.889 | 0.685 | 0.979 |
| G1062 | 1.49E−14 | 5.62E+04 | 4.06E+03 | 8.38E−10 | 3.20E−05 | 0.441 | 3.322 | 0.429 |

Example 5. Multimer Stress Test

The present inventors have previously demonstrated that GL-2045 when isolated through fractionation and then put in pH of 8.5 forms non-specific aggregates, presumably a result of the free sulfhydryl groups.

The isolated homodimers of compounds disclosed herein, each comprising fewer free cysteines compared with GL-2045, are isolated through fractionation and then put in pH 8.5. Samples are taken at Week 2, 4, 8, and 12, then assessed for aggregates by SDS-PAGE, SEC-MALS, dynamic light scattering and/or MS. The results of this study will that in comparison to GL-2045, when the cysteine-optimized compounds disclosed herein are subjected to this procedure, fewer non-specific aggregates will form as a result of fewer free sulfhydryl groups.

Example 6. Stability Test

The present inventors have previously demonstrated that GL-2045 when exposed to increased temperature or to extended time will develop higher order bands and non-specific aggregate bands indicative of instability, presumably a result of the free sulfhydryl groups.

The isolated homodimers of compounds disclosed herein, each comprising fewer free cysteines compared with GL-2045, are isolated through fractionation and then incubated at 37 C. Samples are taken at 2, 4, 8, and 12 weeks, then assessed for aggregates by SDS-PAGE, SEC-MALS, dynamic light scattering and/or MS at each time point. The results of the study will show that in comparison to GL-2045, when the cysteine optimized compounds disclosed herein are subjected to this procedure, fewer higher order bands and non-specific aggregates will form as a result of fewer free sulfhydryl groups.

The invention claimed is:

1. A cysteine-optimized multimerizing stradomer unit comprising at least two stradomer unit monomers,
wherein the at least two stradomer unit monomers each comprises from amino to carboxy terminus, an IgG1 Fc domain monomer comprising an IgG1 hinge, IgG1 CH2, and IgG1 CH3 domain and an IgG2 hinge multimerization domain monomer;
and wherein one or both of the at least two stradomer unit monomers comprise at least one serine mutation at a cysteine residue in the IgG1 Fc domain monomer or the IgG2 hinge multimerization domain monomer at position 5, 11, 14, 152, 210, 243, or a combination thereof, of SEQ ID NO: 10.

2. The cysteine-optimized multimerizing stradomer unit of claim 1, wherein the at least one serine mutation is at a cysteine residue located in the IgG1 hinge monomer of the stradomer unit monomer.

3. The cysteine-optimized multimerizing stradomer unit of claim 2, wherein one or both of the at least two stradomer unit monomers comprise at least two serine mutations at amino acid positions selected from positions 5, 11, and 14 of SEQ ID NO: 10.

4. The cysteine-optimized multimerizing stradomer unit of claim 1, wherein the at least one serine mutation is at a cysteine residue located in the IgG2 hinge domain monomer of the stradomer unit monomer.

5. The cysteine-optimized multimerizing stradomer unit of claim 4, wherein one or both of the at least two multimerizing stradomer unit monomers comprises a serine mutation at amino acid position 243 of SEQ ID NO: 10.

6. The cysteine-optimized multimerizing stradomer unit of claim 1, wherein the at least one serine mutation is at a cysteine residue located in the IgG1 CH2 or IgG1 CH3 domain monomer of each of said at least two stradomer unit monomers.

7. The cysteine-optimized multimerizing stradomer unit of claim 6, wherein one or both of the at least two stradomer unit monomers comprises a serine mutations at amino acid positions 152 and 210 of SEQ ID NO: 10.

8. The cysteine-optimized multimerizing stradomer unit of claim 1, wherein each of the stradomer unit monomers comprises a serine mutation at amino acid positions 5, 11, 14, 243, or a combination thereof, of SEQ ID NO: 10 and wherein the at least two stradomer monomers do not comprise a point mutation at any of positions 236, 237, or 240 of SEQ ID NO: 10.

9. The cysteine-optimized multimerizing stradomer unit of claim 1, wherein the amino acid sequence of one or both of the stradomer unit monomers is independently selected from the group consisting of SEQ ID NOs: 27-42.

10. The cysteine-optimized multimerizing stradomer unit of claim 1, wherein the number of cysteines present in the amino acid sequence of the stradomer is 10, 9, 8, 7, or fewer.

11. The cysteine-optimized multimerizing stradomer unit of claim 1, wherein the stradomer unit exhibits the same multimerization relative to a stradomer comprising SEQ ID NO: 10.

12. The cysteine-optimized multimerizing stradomer unit of claim 11, wherein the amino acid sequence of one or both of the stradomer unit monomers is independently selected from the group consisting of SEQ ID NOs: 28-29, 34-37, 40, and 42.

13. The cysteine-optimized multimerizing stradomer unit of claim 1, wherein the stradomer unit exhibits increased multimerization relative to a stradomer comprising SEQ ID NO: 10.

14. The cysteine-optimized multimerizing stradomer unit of claim 13, wherein the amino acid sequence of one or both of the stradomer unit monomers is SEQ ID NO: 27.

\* \* \* \* \*